United States Patent
Polo et al.

(10) Patent No.: US 9,255,126 B2
(45) Date of Patent: *Feb. 9, 2016

(54) CHIMERIC ALPHAVIRUS REPLICON PARTICLES

(75) Inventors: John M. Polo, Rancho Santa Fe, CA (US); Silvia Perri, Castro Valley, CA (US); Kent Thudium, Oakland, CA (US); Zequn Tang, San Ramon, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 359 days.

This patent is subject to a terminal disclaimer.

(21) Appl. No.: 12/538,432

(22) Filed: Aug. 10, 2009

(65) Prior Publication Data

US 2009/0304745 A1    Dec. 10, 2009

Related U.S. Application Data

(60) Division of application No. 11/397,669, filed on Apr. 3, 2006, now Pat. No. 7,572,453, which is a continuation of application No. 10/310,734, filed on Dec. 4, 2002, now abandoned, which is a continuation-in-part of application No. 10/123,101, filed on Apr. 11, 2002, now Pat. No. 7,531,180.

(60) Provisional application No. 60/295,451, filed on May 31, 2001.

(51) Int. Cl.
| | |
|---|---|
| *A61K 39/193* | (2006.01) |
| *A61K 39/12* | (2006.01) |
| *C12N 7/01* | (2006.01) |
| *C12N 15/86* | (2006.01) |
| *C12N 15/40* | (2006.01) |
| *C07K 14/005* | (2006.01) |
| *C12N 7/00* | (2006.01) |
| *A61K 39/00* | (2006.01) |

(52) U.S. Cl.
CPC .............. *C07K 14/005* (2013.01); *A61K 39/12* (2013.01); *C12N 7/00* (2013.01); *C12N 15/86* (2013.01); *A61K 2039/5256* (2013.01); *A61K 2039/5258* (2013.01); *C07K 2319/00* (2013.01); *C12N 2740/16222* (2013.01); *C12N 2770/36122* (2013.01); *C12N 2770/36134* (2013.01); *C12N 2770/36143* (2013.01); *C12N 2770/36145* (2013.01); *C12N 2770/36162* (2013.01); *C12N 2810/10* (2013.01)

(58) Field of Classification Search
None
See application file for complete search history.

(56) References Cited

U.S. PATENT DOCUMENTS

| | | | | |
|---|---|---|---|---|
| 5,185,440 | A * | 2/1993 | Davis et al. | 536/23.72 |
| 5,789,245 | A | 8/1998 | Dubensky, Jr. et al. | |
| 5,843,723 | A | 12/1998 | Dubensky, Jr. et al. | |
| 6,015,686 | A | 1/2000 | Dubensky, Jr. et al. | |
| 6,015,694 | A | 1/2000 | Dubensky, Jr. et al. | |
| 6,184,024 | B1 | 2/2001 | Lai et al. | |
| 6,261,570 | B1 * | 7/2001 | Parker et al. | 424/205.1 |
| 7,531,180 | B2 * | 5/2009 | Polo et al. | 424/199.1 |
| 7,572,453 | B2 * | 8/2009 | Polo et al. | 424/199.1 |

FOREIGN PATENT DOCUMENTS

| | | |
|---|---|---|
| WO | 9507994 | 3/1995 |
| WO | 9738087 | 10/1997 |
| WO | 9837911 | 9/1998 |
| WO | 9853077 | 11/1998 |
| WO | 9918226 | 4/1999 |

OTHER PUBLICATIONS

Oberste et al (Virology 219: 314-320, 1996).*
Pushko et al (Virology 239:389-401, 1997).*
Driver et al (Idrugs 1: 678-685, 1998).*
Biosafety in Microbiological and Biomedical Laboratories 5th Edition. U.S. Department of Health and Human Services, Public Health Service, Centers for Disease Control and Prevention, National Institutes of Health. HHS Publication No. (CDC) 21-1112, Revised Dec. 2009. pp. 233-267.*
Vihinen et al (Journal of Biological Chemistry 276:5745-5752, 2001).*
Davis et al (Virology 171:189-204, 1989.*
Zhou et al (Vaccine 12:1554-1514, 1994).*
Tubulekas et al (Journal of Virology 72:2825-2831, 1998).*
Tuittila et al (Journal of Virology 74:4579-4589, 2000).*
Genbank NP_690588, 2012.*
Genbank NP_740706, 2012.*
Genbank AAD14550, 1999.*
Genbank POLN_GETV, 2015.*
Berglund et al., "Enhancing immune responses using suicidal DNA vaccines," Nat. Biotech 16:562-565 (1998).
Berglund et al., "Immunization with recombinant Semliki forest virus induces protection against influenza challenge in mice," Vaccine 17:497-507 (1999).
Davis et al., "In vitro synthesis of infectious Venezuelan equine encephalitis virus RNA from a cDNA clone: analysis of a viable deletion mutant," Virology, 171:189-204 (1989).
Davis et al., "Vaccination of macaques against pathogenic simian immunodeficiency virus with Venezuelan equine encephalitis virus replicon particles," J. Virology. 74:371-378 (2000).

(Continued)

*Primary Examiner* — Benjamin P Blumel
*Assistant Examiner* — Rachel Gill
(74) *Attorney, Agent, or Firm* — Laurence Shumway; Helen Lee

(57) ABSTRACT

Chimeric alphavirus particles and alphavirus replicon RNAs are provided including methods of making and using same. The alphavirus replicon RNAs comprise deletions in one or more nonstructural proteins. Methods of making, using, and therapeutic preparations containing the chimeric alphavirus particle are disclosed.

20 Claims, 15 Drawing Sheets

(56) References Cited

OTHER PUBLICATIONS

Dubensky et al, "Sindbis virus DNA-based expression vectors: utility for in vitro and in vivo gene transfer," J. Virology. 70:508-519 (1996).
Fields et al., "Alphaviruses," Virology (Third Edition) pp. 843-848 (1996).
Frolov et al., "Packaging signals in alpha virus," J. Virology 71(1):248-258 (1997).
Frolov et al., "Sindbis virus replicons and Sindbis virus: assembly of chimeras and of particles deficient in virus RNA," J. Virology 71(4):2819-2829 (1997).
Gardner et al., "Infection of human dendritic cells by a Sindbis virus replicon vector is determined by a single amino acid substitution in the E2 glycoprotein," J. Virology, 74(24):11849-11857 (2000).
Guirakhoo et al., "Construction, safety and immunogenicity in non-human primates of a chimeric yellow fever-dengue virus tetravalent vaccine," J. Virology 75(16):7290-7304 (2001).
Kim et al, "Adaptive mutations in Sindbis virus E2 and Ross River virus E1 that allow efficient budding of chimeric viruses," J. Virology 74(6):2663-2670 (2000).
Kuhn et al., "Chimeric Sindbis-Ross River viruses to study interactions between alphavirus nonstructural and structural regions," J. Virology 70(11):7900-7909 (1996).
Lee et al., "Identification of a protein binding site on the surface of the alphavirus nucleocapsid and its implication in virus assembly," Structure 4:531-541 (1996).
Liljestrom, "A new generation of animal cell expression vectors based on the Semliki Forest virus replicon," Bio/Technology 9:1356-1361 (1991).
Lopez, Susana et al., "Nucleocapsid-glycoprotein interactions required for assembly of alphavirus," J. Virology 68(3): 1316-1323 (1994).
Monath et al., "Chimeric yellow fever virus 17D-Japanese encephalitis virus vaccine: dose-response effectiveness and extended safety testing in Rhesus monkeys," J. Virology 74(4):1742-1751 (2000).
Owen et al., "Identification of a region in the Sindbis virus nucleocapsid protein that is involved in the specificity of RNA encapsidation," J. Virology, 70(5):2757-2763 (1996).
Polo et al., "Stable alphavirus packaging cell lines for sindbis virus and Semliki Forest virus-derived vectors," PNAS 96:4598-4603 (1999).
Powers et al., "The use of chimeric Venezuelan equine encephalitis viruses as an approach for the molecular identification of natural virulence determinants," J. Virology 74(9):4258-4263 (2000).
Pushko et al., "Replicon-helper systems from attenuated Venezuelan equine encephalitis virus: expression of heterologous genes in vitro and immunization against heterologous pathogens in vivo," Virology 239:389-401 (1997).

Schlesinger et al., "Alphavirus vectors for gene expression and vaccines," Curr. Opin. Biotechnol. 10:434-439 (1999).
Schoepp et al., "Recombinant chimeric western and eastern equine encephalitis viruses as potential vaccine candidates," Virology 302:299-309 (2002).
Smerdou et al., "Alphavirus vectors: from protein production to gene therapy," Gene Therapy and Regulation, 1 (1):33-63 (2000).
Smyth et al., "Efficient multiplication of a Semliki Forest virus chimera containing Sindbis virus spikes," J. Virology 71 (1):818-823 (1997).
Strauss et al, "The alphaviruses: gene expression, replication, and evolution," Microbiological Reviews 58(3):491-562 (1994).
Van Der Most et al., "Chimeric yellow fever/dengue virus as a candidate dengue vaccine: quantitation of the dengue virus-specific CD8 T-cell response," J. virology 74(17):8094-8101 (2000).
Weiss et al., "Interactions between Sindbis virus RNAs and a 68 amino acid derivative of the viral capsid protein further defines the capsid binding site," Nucleic Acids Research, 22(5):780-786 (1994).
White et al., "Deletion analysis of a defective interfering Semliki Forest virus RNA genome defines a region in the nsP2 sequence that is required for efficient packaging of the genome into virus particles," J. Virology, 72(5):4320-4326 (1998).
Xiong et al., "Sindbis virus: an efficient, broad host range vector for gene expression in animal cells," Science 243:1188-1191 (1989).
Yao et al., "Interactions between PE2, E1 and 6K required for assembly of alphaviruses studied with chimeric viruses," J. Virology 70(11):7910-7920 (1996).
Cheng et al, "Nucleocapsid and glycoprotein organization in an enveloped virus," Cell. Feb. 24, 1995;80(4):621-30.
Barth et al., "Alphavirus assembly and entry: role of the cytoplasmic tail of the E1 spike subunit," J. Virol. Dec. 1992;66 (12)1560-4.
Hariharan et al., "DNA immunization against herpes simplex virus: enhanced efficacy using a Sindbis virus-based vector," J Virol. Feb. 1998;72(2):950-8.
Kowalski et al., "Evaluation of neurovirulence and biodistribution of Venezuelan equine encephalitis replicon particles expressing herpes simplex virus type 2 glycoprotein D," Vaccine. Mar. 8, 2007;25(12):2296-305. Epub Dec. 12, 2006.
Kinney et al., "The full-length nucleotide sequences of the virulent Trinidad donkey strain of Venezuelan equine encephalitis virus and its attenuated vaccine derivative, strain TC-83," Virology. May 1989;170(1):19-30.
Takkinen, "Complete nucleotide sequence of the nonstructural protein genes of Semliki Forest virus," Nucleic Acids Res. Jul. 25, 1986;14(14):5667-82.
Strauss et al., "Complete nucleotide sequence of the genomic RNA of Sindbis virus," Virology. Feb. 1984;133 (1):92-110.

* cited by examiner

VEE FRAGMENT #2 (Hpa[659]-BciVI[1344]; ΔNSP1)

```
VEE 2-1
656 CTAGAGTTA ACGGCTCGTA ACATAGGCCT ATGCAGCTCT GACGTTATGG
TCAAT TGCCGAGCAT TGTATCCGGA TACGTCGAGA CTGCAATACC
VEE 2-26 VEE 2-25
```

VEE 2-2
706 AGCGGTCACG TAGAGGGATG TCCATTCTTA GAAAGAAGTA TTTGAAACCA
TCGCCAGTGC ATCTCCCTAC AGGTAAGAAT CTTTCTTCAT AAACTTTGGT
VEE 2-24

VEE 2-3
756 TCCAACAATG TTCTATTCTC TGTTGGCTCG ACCATCTACC ACGAGAAGAG
AGGTTGTTAC AAGATAAGAG ACAACCGAGC TGGTAGATGG TGCTCTTCTC
VEE 2-23

VEE 2-4
806 GGACTTACTG AGGAGCTGGC ACCTGCCGTC TGTATTTCAC TTACGTGGCA
CCTGAATGAC TCCTCGACCG TGGACGGCAG ACATAAAGTG AATGCACCGT

VEE 2-5
856 AGCAAAATTA CACATGTCGG TGTGAGACTA TAGTTAGTTG CGACGGGTAC
TCGTTTTAAT GTGTACAGCC ACACTCTGAT ATCAATCAAC GCTGCCCATG
VEE 2-22

906 GTCGTTAAAA GAATAGCTAT CAGTCCAGGC CTGTATGGGA AGCCTTCAGG
CAGCAATTTT CTTATCGATA GTCAGGTCCG GACATACCCT TCGGAAGTCC
VEE 2-21

VEE 2-6
956 CTATGCTGCT ACGATGCACC GCGAGGGATT CTTGTGCTGC AAAGTGACAG
GATACGACGA TGCTACGTGG CGCTCCCTAA GAACACGACG TTTCACTGTC
VEE 2-20

VEE 2-7
1006 ACACATTGAA CGGGGAGAGG GTCTCTTTTC CCGTGTGCAC GTATGTGCCA
TGTGTAACTT GCCCCTCTCC CAGAGAAAAG GGCACACGTG CATACACGGT
VEE 2-19

VEE 2-8
1056 GCTACATTGT GTGACCAAAT GACTGGCATA CTGGCAACAG ATGTCAGTGC
CGATGTAACA CACTGGTTTA CTGACCGTAT GACCGTTGTC TACAGTCACG
VEE 2-18

FIG. 2A

```
1106  GGACGACGCG CAAAAACTGC TGGTTGGGCT CAACCAGCGT ATAGTCGTCA
      CCTGCTGCGC GTTTTTGACG ACCAACCCGA GTTGGTCGCA TATCAGCAGT

1156  ACGGTCGCAC CCAGAGAAAC ACCAATACCA TGAAAAATTA CCTTTTGCCC
      TGCCAGCGTG GGTCTCTTTG TGGTTATGGT ACTTTTTAAT GGAAAACGGG

1206  GTAGTGGCCC AGGCATTTGC TAGGTGGGCA AGGAATATA AGGAAGATCA
      CATCACCGGG TCCGTAAACG ATCCACCCGT TCCTTATAT TCCTTCTAGT

1256  AGAAGATGAA AGGCCACTAG GACTACGAGA TAGACAGTTA GTCATGGGGT
      TCTTCTACTT TCCGGTGATC CTGATGCTCT ATCTGTCAAT CAGTACCCCA

1306  GTTGTTGGGC TTTTAGAAGG CACAAGATAA CATCTATTTA TAAGCGCCCG
      CAACAACCCG AAAATCTTCC GTGTTCTATT GTAGATAAAT ATTCGCGGGC

1356  GATACA
      CTATGTGCGC
```

FIG. 2B

Hybrid capsid protein for the efficient production of chimeric SIN/VEE alphavirus particles CapsidRNA binding.apr
RNA binding domain

```
                    1              10              20              30              40              50              60              78
SINDC      (1)            -KQAPKQPPKPKPKP KKQ KQPAKP           -- KPGKRQRMALKLEADRSFDVKNEDGDVIGHALAMEGK
SIN HR     (1)            -KQAPKQPPKPKPKP KKQ KQPAKP           -- KPGKRQRMALKLEADRLFDVKNEDGDVIGHALAMEGK
TRD        (1)            -SQKQKGG GKKKQGKKKKNQGKKKKAKTGPPNPKAQ GNKKK   KPGKRQRMVMKLESDKTFPIM LEGKINGYACVVGGK
6119       (1)            -APKQKG G GKKKQGKKKKNQGKKKKAKTGPPNPKAQ GNKKK   NKPGKRQRMVMKLESDKTFPIM LEGKINGYACVVGGK
MAC10      (1)            -PQKPKRGSQGKR KKKNQGKKKKAKTGPPNQKAQ GNKKK   NKKPGKRQRMVMKLESDKTFPIM LEGKINGYACVVGGK
Consensus  (1)             QKPK  G  QGKKKKNQGKKKKAKTGPPN  KAQ  GNKKK    KPGKRQRMVMKLES KTFPIM LEGKIN YA CVVGGK
```

S113  S116  S127  S129

Section 78

Replicon RNA: 5'—[SIN nonstructural proteins]—[G.O.I.]—3'

Hybrid capsid DH: 5'—[S/V capsid]—3'

Glycoprotein DH: 5'—[VEE Glycoproteins]—3'

FIG. 4

Hybrid E2 glycoprotein for the efficient production of chimeric SIN/VEE alphavirus particles E2tails.apr

```
                    membrane | cytoplasm
                    ←────────┼────────→
                  1      *      10         20        36
SINDCE2t     (1) CACKARRE CLTPYALAPNAVI PTSLAIL CCVRSANA
SUNHRE2t     (1) CACKARRE CLTPYALAPNAVI PTSLAIL CCVRSANA
TRDE2t       (1) LFCKSRVA CLTPYRLTPNARIPF CLAVLCC ARTARA
6119E2t      (1) LFCKSRVS CLTPYRLTPNARMPL CLAVLCC ARTARA
MAC10E2t     (1) LFCKSRVL CLTPYQLTPNARMPL CLAVF CC ARTARA
Consensus    (1) LFCKSRVS CLITPY  LTPNARIP  CLAVLCC ARTARA
                      ↑
```

[Diagram: 5' SIN nonstructural proteins — G.O.I. — 3'; SIN capsid 3'; VEE gly-SE2 tail 3'; with E2 tail substitution showing E1, E2, nucleocapsid, cytoplasm]

Chimera 1A: SIN packaging signal insertion at nsP4/ truncated junction region promoter

```
     MscI
1    TGGCCATGAC CACCCTGGCC TCCTCCGTGA AGAGCTTTTC CTATCTTCGC
     ACCGGTACTG GTGGGACCGG AGGAGGCACT TCTCGAAAAG GATAGAAGCG

END nsP4 - VEE nt. 7527
51   GGCGCGCCCA TCACCTTGTA TGGATAAGGG ATCACGGGAG AAACCGTGGG
     CCGCGCGGGT AGTGGAACAT ACCTATTCCC TAGTGCCCTC TTTGGCACCC

101  ATACGCGGTT ACACACAATA GCGAGGGCTT CTTGCTATGC AAAGTTACTG
     TATGCGCCAA TGTGTGTTAT CGCTCCCGAA GAACGATACG TTTCAATGAC

151  ACACAGTAAA AGGAGAACGG GTATCGTTCC CTGTGTGCAC GTACATCCCG
     TGTGTCATTT TCCTCTTGCC CATAGCAAGG GACACACGTG CATGTAGGGC

VEE nt. 7454
201  GCCACCATAC CATGACTACT CTAGCTAGCA GTGTTAAATC ATTCAGCTAC
     CGGTGGTATG GTACTGATGA GATCGATCGT CACAATTTAG TAAGTCGATG

26s RNA
251  CTGAGAGGGG CCCCTATAAC TCTCTACGGC TAACCTGAAT GGACTACGAC
     GACTCTCCCC GGGGATATTG AGAGATGCCG ATTGGACTTA CCTGATGCTG

AscI
301  ATAGTCTAGT CCGCCAAGCC TCAGCGG
     TATCAGATCA GGCGGTTCGG AGTCGCCGCGC
```

3' end nsp4/-80 to +14 subgenomic promoter with altered codon usage, unaltered AA sequence Sindbis Virus Packaging Signal Seq. (SIN nt. 945-1076)

-80 to +14 (or -98 to +14) subgenomic promoter with native codon usage

FIG. 7

Chimera 1B: SIN packaging signal insertion at nsP4/non-truncated junction region promoter

```
    MscI
1   TGGCCATGAC CACCCTGGCC TCCTCCGTGA AGAGCTTTTC CTATCTTCGC
    ACCGGTACTG GTGGGACCGG AGGAGGCACT TCTCGAAAAG GATAGAAGCG

VEE nt. 7527
51  GGCGCGCCCA TCACCTTGTA TGGATAAGGG ATCACGGGAG AAACCGTGGG
    CCGCGCGGGT AGTGGAACAT ACCTATTCCC TAGTGCCCTC TTTGGCACCC

101 ATACGCGGTT ACACACAATA GCGAGGGCTT CTTGCTATGC AAAGTTACTG
    TATGCGCCAA TGTGTGTTAT CGCTCCCGAA GAACGATACG TTTCAATGAC

151 ACACAGTAAA AGGAGAACGG GTATCGTTCC CTGTGTGCAC GTACATCCCG
    TGTGTCATTT TCCTCTTGCC CATAGCAAGG GACACACGTG CATGTAGGGC

VEE nt. 7435
201 GCCACCATAA CTTCCATCAT AGTTATGGCC ATGACTACTC TAGCTAGCAG
    CGGTGGTATT GAAGGTAGTA TCAATACCGG TACTGATGAG ATCGATCGTC

251 TGTTAAATCA TTCAGCTACC TGAGAGGGGC CCCTATAACT CTCTACGGCT
    ACAATTTAGT AAGTCGATGG ACTCTCCCCG GGGATATTGA GAGATGCCGA

26S →                              AscI
301 AACCTGAATG GACTACGACA TAGTCTAGTC CGCCAAGCCT CAGCGG
    TTGGACTTAC CTGATGCTGT ATCAGATCAG GCGGTTCGGA GTCGCC
```

-80 TO +114
subgenomic promoter
with altered codon usage

Sindbis Virus
Packaging Signal Seq.
(SIN nt. 945-1076)

-98 TO +14
subgenomic promoter
with native codon usage

Protein alignment of partial polymerase sequences for three different alphaviruses and BMV

```
                                                         SEQ ID NO:
SIN(361)  KQGDPVLETDIASFDKSQDDSMALTGLMILEDLGVDQPLLDLIEC       79
VEE(361)  QPGDQVLETDIASFDKSEDDSMALTALMILEDLGVDAELTLIEA       80
SFV(362)  HPGDPVLETDIASFDKSQDDSIALTALMILEDLGVDQYLLDLIEA       81
BMV(456)  LNNRYFLEADLSKFDKSQGELHLEFQREILLALGFPAPLTNWWSD      82
                          *
```

Numbering indicated based on first amino acid shown

FIG. 14

CHIMERIC ALPHAVIRUS REPLICON PARTICLES

CROSS-REFERENCE TO RELATED APPLICATIONS

This application is a division of Ser. No. 11/397,669, filed Apr. 3, 2006, pending, which is a continuation of Ser. No. 10/310,734, filed Dec. 4, 2002, now abandoned, which is a continuation-in-part of Ser. No. 10/123,101, filed Apr. 11, 2002, now U.S. Pat. No. 7,531,180, which claims the benefit of U.S. Provisional Application No. 60/295,451, filed May 31, 2001. Each application is hereby incorporated by reference in its entirety.

This application incorporates by reference the contents of a 60 Kb file created on Jun. 16, 2011 and named "51602USDIVrevisedseqlist.txt," which is the sequence listing for this application.

GOVERNMENT SUPPORT

The invention was supported, in whole or in part, by NIH HIVDDT Grant No. N01-A1-05396 from the National Institutes of Health. The Government may have certain rights in the invention.

TECHNICAL FIELD

The present invention relates generally to chimeric alphavirus particles. More specifically, the present invention relates to the preparation of chimeric alphaviruses having RNA derived from at least one alphavirus and one or more structural elements (capsid and/or envelope) derived from at least two different alphaviruses The chimeric alphaviruses of the present invention are useful in the ex vivo and in vivo administration of heterologous genes and also have therapeutic or prophylactic applications.

BACKGROUND OF THE INVENTION

Alphaviruses comprise a set of genetically, structurally, and serologically related arthropod-borne viruses of the Togaviridae family. Twenty-six known viruses and virus subtypes have been classified within the alphavirus genus, including, Sindbis virus, Semliki Forest virus, Ross River virus, and Venezuelan equine encephalitis virus. Sindbis virus is the prototype member of the Alphavirus genus of the Togaviridae family. Its replication strategy has been well characterized in a variety of cultured cells and serves as a model for other alphaviruses. Briefly, the genome of Sindbis (like other alphaviruses) is an approximately 12 kb single-stranded positive-sense RNA molecule that is capped, polyadenylated, and contained within a virus-encoded capsid protein shell. The nucleocapsid is further surrounded by a host-derived lipid envelope, into which two viral-specific glycoproteins, E1 and E2, are inserted and anchored by a cytoplasmic tail to the nucleocapsid. Certain alphaviruses (e.g., SFV) also maintain an additional protein, E3, which is a cleavage product of the E2 precursor protein, PE2.

After virus particle adsorption to target cells, penetration, and uncoating of the nucleocapsid to release viral genomic RNA into the cytoplasm, the replicative process occurs via four alphaviral nonstructural proteins (nsPs), translated from the 5' two-thirds of the viral genome. Synthesis of a full-length negative strand RNA, in turn, provides template for the synthesis of additional positive strand genomic RNA and an abundantly expressed 26S subgenomic RNA, initiated internally at the junction region promoter. The alphavirus structural proteins are translated from the subgenomic 26S RNA, which represents the 3' one-third of the genome, and like the nsPs, are processed post-translationally into the individual proteins.

Several members of the alphavirus genus are being developed as "replicon" expression vectors for use as vaccines and therapeutics. Replicon vectors may be utilized in several formats, including DNA, RNA, and recombinant replicon particles. Such replicon vectors have been derived from alphaviruses that include, for example, SIN (Xiong et al. (1989) *Science* 243:1188-119i; Dubensky et al. (1996) *J. Virol.* 70:508-519; Hariharan et al. (1998) *J. Virol.* 72:950-958; Polo et al. (1999) *Proc. Natl. Acad. Sci. USA* 96:4598-4603), Semliki Forest virus (Liljestrom (1991) *Bio/Technology* 9:1356-1361; Berglund et al. (1998) *Nat. Biotech.* 16:562-565), and VEE (Pushko et al. (1997) *Virology* 239:389401). A wide body of literature has now demonstrated efficacy of alphavirus replicon vectors for applications such as vaccines (see for example, Dubensky et al., ibid; Berglund et al., ibid; Hariharan et al., ibid, Pushko et al., ibid, Polo et al., ibid; Davis et al. (2000) *J. Virol.* 74:371-378; Schlesinger & Dubensky (1999) *Curr. Opin. Biotechnol.* 10:434-439; Berglund et al. (1999) *Vaccine* 17:497-507). Generally, speaking, a "replicon" particle refers to a virus particle containing a self-replicating nucleic acid. The replicon particle itself is generally considered replication incompetent or "defective," that is no progeny replicon particles will result when a cell is infected with a replicon particle. Through the years, several synonymous terms including recombinant viral particle, recombinant alphavirus particle, alphavirus replicon particle and replicon particle have emerged that are used to describe replicon particles. However, as used herein, these terms all refer to a virion-like unit containing a virus-derived RNA vector replicon, specifically, an alphavirus RNA vector replicon. Moreover, these terms may be referred to collectively as vectors, vector constructs or gene delivery vectors.

Currently, several alphaviruses are being developed as gene delivery systems for vaccine and other therapeutic applications. Although generally quite similar in overall characteristics (e.g., structure, replication), individual alphaviruses may exhibit some particular property (e.g., receptor binding, interferon sensitivity, and disease profile) that is unique. To exploit the most desirable properties from each virus a chimeric replicon particle approach has been developed. Specifically, a chimeric alphavirus replicon particle may have RNA derived from one virus and one or more structural components derived from a different virus. The viral components are generally derived from closely related viruses; however, chimeric virus particles made from divergent virus families are possible.

It was previously demonstrated that chimeric alphavirus replicon particles can be generated, wherein the RNA vector is derived from a first alphavirus and the structural "coat" proteins (e.g., envelope glycoproteins) are derived from a second alphavirus (see, for example U.S. Pat. No. 6,376,236; see also, U.S. Pat. Nos. 5,789,245; 5,842,723; and 6,015,694; as well as WO 95/07994, WO 97/38087 and WO 99/18226). However, although previously-described strategies were successful for making several alphavirus chimeras, such chimeric particles are not always produced in commercially viable yields, perhaps due to less efficient interactions between the viral RNA and structural proteins, resulting in decreased productivity.

Thus, there remains a need for compositions comprising and methods of making and using chimeric replicon particles and replicons, for example for use as gene delivery vehicles having altered cell and tissue tropism and/or structural protein surface antigenicity.

SUMMARY OF THE INVENTION

The present invention includes compositions comprising chimeric alphaviruses and alphavirus replicon particles and methods of making and using these particles.

In one aspect, the present invention provides chimeric alphavirus particles, comprising RNA derived from one or more alphaviruses; and structural proteins wherein at least one of said structural proteins is derived from two or more alphaviruses. In certain embodiments, the RNA is derived from a first alphavirus and the structural proteins comprise (a) a hybrid capsid protein having (i) an RNA binding domain derived from said first alphavirus and (ii) an envelope glycoprotein interaction domain derived from a second alphavirus; and (b) an envelope glycoprotein from said second alphavirus. In other embodiments, the RNA is derived from a first alphavirus and the structural proteins comprise (a) a capsid protein derived from first alphavirus; and (b) an envelope glycoprotein having (i) a cytoplasmic tail portion and (ii) a remaining portion, wherein the cytoplasmic tail portion is derived from said first alphavirus and the remaining portion derived from a second alphavirus. The nucleic acid can be derived from a first virus that is contained within a viral capsid derived from the same virus but having envelope glycoprotein components from a second virus. In still, further embodiments, the chimeric particles comprise hybrid capsid proteins and hybrid envelope proteins. Furthermore, the hybrid proteins typically contain at least one functional domain derived from a first alphavirus while the remaining portion of the protein is derived from one or more additional alphaviruses (e.g., envelope glycoprotein components derived from the first virus, the second virus or a combination of two or more viruses). The remaining portion can include 25% to 100% (or any value therebetween) of sequences derived from different alphaviruses. The RNA contained within a chimeric alphavirus particle of the present invention may include one or more of the following: an RNA comprising an alphavirus replicon vector for expression of heterologous sequences and/or an RNA comprising the genome of one or more alphaviruses (e.g. for use as an attenuated live virus vaccine).

Thus, the modified (or chimeric) alphavirus particles (e.g., replicon particles) of the present invention include, but are not limited to, particles comprising a nucleic acid derived from one or more alphaviruses that is contained within at least one structural element (capsid and/or envelope protein) derived from two or more alphaviruses (e.g., provided by defective helpers or other structural protein gene expression cassettes). For example, the chimeric particles comprise RNA from a first alphavirus, a hybrid capsid protein with an RNA binding domain from the first alphavirus and an envelope glycoprotein interaction domain from a second alphavirus, and an envelope glycoprotein from the second alphavirus. In other embodiments, the particles of the present invention comprise RNA from a first alphavirus, a capsid protein the first alphavirus and an envelope glycoprotein that has a cytoplasmic tail from the first alphavirus with the remaining portion of the envelope glycoprotein derived from a second alphavirus. In still another embodiment, the chimeric alphavirus particles comprise RNA from a first alphavirus, the RNA having a packaging signal derived from a second alphavirus inserted, for example, in a nonstructural protein gene region that is deleted, and a capsid protein and envelope glycoprotein from the second alphavirus.

In another aspect, the invention includes chimeric alphavirus particles comprising (a) RNA encoding one or more nonstructural proteins derived from a first alphavirus and a packaging signal derived from a second alphavirus different from said first alphavirus (e.g., a packaging signal inserted into a site selected from the group consisting of the junction of nsP3 with nsP4, following the open reading frame of nsP4 and a deletion in a nonstructural protein gene); (b) a capsid protein derived from said second alphavirus; and (c) an envelope protein derived from an alphavirus different from said first alphavirus. In certain embodiments, the envelope protein is derived from the second alphavirus.

In any of the chimeric replicon particles described herein, the RNA can comprises, in 5' to 3' order (i) a 5' sequence required for nonstructural protein-mediated amplification, (ii) a nucleotide sequence encoding alphavirus nonstructural proteins, (iii) a means for expressing a heterologous nucleic acid (e.g., a viral junction region promoter), (iv) the heterologous nucleic acid sequence (e.g., an immunogen), (v) a 3' sequence required for nonstructural protein-mediated amplification, and (vi) a polyadenylate tract. In certain embodiments, the heterologous nucleic acid sequence replaces an alphavirus structural protein gene. Further, in any of the embodiments described herein, the chimeras are comprised of sequences derived from Sindbis virus (SIN) and Venezuelan equine encephalitis virus (VEE), for example where the first alphavirus is VEE and the second alphavirus is SIN or where the first alphavirus is VEE and second is SIN.

In other aspects, the invention includes an alphavirus replicon RNA comprising a 5' sequence required for nonstructural protein-mediated amplification, sequences encoding biologically active alphavirus nonstructural proteins, an alphavirus subgenomic promoter, a non-alphavirus heterologous sequence, and a 3' sequence required for nonstructural protein-mediated amplification, wherein the sequence encoding at least one of said nonstructural proteins is derived from a Biosafety Level 3 (BSL-3) alphavirus and wherein the sequences of said replicon RNA exhibit sequence identity to at least one third but no more than two-thirds of a genome of a BSL-3 alphavirus. In certain embodiments, cDNA copies of these replicons are included as nucleic acid vector sequences in a Eukaryotic Layered Vector Initiation System (ELVIS) vector, for example an ELVIS vector comprising a 5' promoter which is capable of initiating within a eukaryotic cell the synthesis of RNA from cDNA, and the nucleic acid vector sequence which is capable of directing its own replication and of expressing a heterologous sequence. The BSL-3 alphavirus can be, for example, Venezuelan equine encephalitis virus (VEE).

In any of the chimeric particles and replicons described herein, the RNA can further comprise a heterologous nucleic acid sequences, for example, a therapeutic agent or an immunogen (antigen). The heterologous nucleic acid sequence can replace one, more than one, or all of the structural protein coding sequences. Further the heterologous nucleotide sequence can encode, for example, a polypeptide antigen derived from a pathogen (e.g., an infectious agent such as a virus, bacteria, fungus or parasite). In preferred embodiments, the antigen is derived from a virus such as human immunodeficiency virus (HIV) (e.g. gag, gp120, gp140, gp160 pol, rev, tat, and nef), a hepatitis C virus (HCV) (e.g., C, E1, E2, NS3, NS4 and NS5), an influenza virus (e.g., HA, NA, NP, M), a paramyxovirus such as parainfluenza virus or respiratory syncytial virus or measles virus (e.g., NP, M, F, HN, H), a herpes virus (e.g., glycoprotein B, glycoprotein D), a Filovirus such as Marburg or Ebola virus (e.g. NP, GP), a bunyavirus such as Hantaan virus or Rift Valley fever virus (e.g., G1, G2, N), or a flavivirus such as tick-borne encephalitis virus or West Nile virus (e.g., C, prM, E, NS1, NS3, NS5). In any of compositions or methods described herein, the RNA can further comprise a packaging signal from a second alphavirus inserted within a deleted non-essential region of a nonstructural protein 3 gene (nsP3 gene).

In another aspect, methods of preparing (producing) alphaviral replicon particles are provided. In certain embodiments, the particles are prepared by introducing any of the replicon and defective helper RNAs described herein into a suitable host cell under conditions that permit formation of the particles. In any of the methods described herein, the defective helper RNAs can include chimeric and/or hybrid structural proteins (or sequences encoding these chimeric/hybrid proteins) as described herein. For example, in certain embodiments, the method comprises introducing into a host cell: (a) an alphavirus replicon RNA derived from one or more alphaviruses, further containing one or more heterologous sequence(s); and (b) at least one separate defective helper RNA(s) encoding structural protein(s) absent from the replicon RNA, wherein at least one of said structural proteins is derived from two or more alphaviruses, wherein alphavirus replicon particles are produced. The replicon RNA can be derived from one or more alphaviruses and the structural proteins can include one or more hybrid proteins, for example, a hybrid capsid protein having an RNA binding domain derived from a first alphavirus and an envelope glycoprotein interaction domain derived from a second alphavirus; and/or a hybrid envelope protein having a cytoplasmic tail portion and a remaining portion, wherein the cytoplasmic tail portion is derived from a first alphavirus and the remaining portion of said envelope glycoprotein derived from one or more alphaviruses different than the first.

In yet another aspect, the invention provides a method for producing alphavirus replicon particles, comprising introducing into a host cell (a) an alphavirus replicon RNA encoding one or more nonstructural proteins from a first alphavirus, a packaging signal derived from a second alphavirus, (e.g., inserted into a site selected from the group consisting of the junction of nsP3 with nsP4, following the nsP4 open reading frame and and a deleted region of a nonstructural protein gene) and one or more heterologous sequence(s); and (b) at least one separate defective helper RNA(s) encoding structural protein(s) absent from the replicon RNA, wherein at least one of said structural proteins is a capsid protein derived from said second alphavirus, and at least one of said structural proteins is an envelope protein derived from an alphavirus different from said first alphavirus.

IP yet another aspect, the invention includes alphavirus packaging cell lines comprising one or more structural protein expression cassettes comprising sequences encoding one or more structural proteins, wherein at least one of said structural proteins is derived from two or more alphaviruses. In certain embodiments, one or more structural protein expression cassettes comprise cDNA copies of a defective helper RNA and, optionally, an alphavirus subgenomic promoter. Further, in any of these embodiments, the defective helper RNA can direct expression of the structural protein(s).

In yet another aspect, methods of producing viral replicon particles using packaging cell lines are provided. Typically, the methods comprise introducing, into any of the alphavirus packaging cell lines described herein, any of the alphavirus replicon RNAs described herein, wherein an alphavirus particle comprising one or more heterologous RNA sequence(s) is produced. Thus, in certain embodiments, the RNA will include a packaging signal insertion derived from a different alphavirus, inserted for example into a region of nonstructural protein gene deletion. In other embodiments, the packaging cell comprises three separate RNA molecules, for example, a first defective helper RNA molecule encodes for viral capsid structural protein(s), a second defective helper RNA molecule encodes for one or more viral envelope structural glycoprotein(s) and a third replicon RNA vector which comprises genes encoding for required nonstructural replicase proteins and a heterologous gene of interest substituted for viral structural proteins, wherein at least one of the RNA molecules includes sequences derived from two or more alphaviruses. Modifications can be made to any one or more of the separate nucleic acid molecules introduced into the cell (e.g., packaging cell) for the purpose of generating chimeric alphavirus replicon particles. For example, a first defective helper RNA can be prepared having a gene that encodes for a hybrid capsid protein as described herein. In one embodiment, the hybrid capsid protein has an RNA binding domain derived from a first alphavirus and a glycoprotein interaction domain from a second alphavirus. A second defective helper RNA may have a gene or genes that encodes for an envelope glycoprotein(s) from a second alphavirus, while the replicon vector RNA is derived from a first alphavirus. In other embodiments, an RNA replicon vector construct is derived from a first alphavirus having a packaging signal from a second alphavirus, inserted for example, in a nonstructural protein gene region that is deleted. The first and second defective helper RNAs have genes that encode for capsid protein or envelope proteins from the second alphavirus. In other embodiments, a chimeric alphavirus replicon particle is made using a first defective helper RNA encoding a capsid protein (derived from a first alphavirus that is the same as the replicon vector source virus) and a second defective helper RNA having a gene that encodes for a hybrid envelope glycoprotein having a cytoplasmic tail fragment from the same alphavirus as the capsid protein of the first helper RNA and a surface-exposed "ectodomain" of the glycoprotein derived from a second alphavirus. The tail fragment interacts with the capsid protein and a chimeric replicon particle having RNA and a capsid derived from a first virus, and an envelope derived primarily from a second virus results.

In another aspect, the invention provides a method for producing alphavirus replicon particles, comprising introducing into a permissible cell, (a) any of the alphavirus replicon RNAs described herein comprising control elements and polypeptide-encoding sequences encoding (i) biologically active alphavirus nonstructural proteins and (ii) a heterologous protein, and (b) one or more defective helper RNA(s) comprising control elements and polypeptide-encoding sequences encoding at least one alphavirus structural protein, wherein the control elements can comprise, in 5' to 3' order, a 5' sequence required for nonstructural protein-mediated amplification, a means for expressing the polypeptide-encoding sequences, and a 3' sequence required for nonstructural protein-mediated amplification, and further wherein one or more of said RNA replicon control elements are different than said defective helper RNA control elements; and incubating said cell under suitable conditions for a time sufficient to permit production of replicon particles. In certain embodiments, the replicon RNA and said defective helper RNA(s) further comprise a subgenomic 5'-NTR. In other embodiments, the subgenomic 5'-NTR of the replicon RNA is different that the subgenomic 5'-NTR of the defective helper RNA; the 5' sequence required for nonstructural protein-mediated amplification of the replicon RNA is different than the 5' sequence required for nonstructural protein-mediated amplification of the defective helper RNA; the 3' sequence required for nonstructural protein-mediated amplification of the replicon RNA is different than the 3' sequence required for nonstructural protein-mediated amplification of the defective helper RNA; and/or the means for expressing said polypeptide-encoding sequences of the replicon RNA is different than the means for expressing said polypeptide-encoding sequences of the defective helper RNA.

In still further aspects, methods are provided for stimulating an immune response within a warm-blooded animal, comprising the step of administering to a warm-blooded animal a preparation of alphavirus replicon particles according to the present invention expressing one or more antigens derived from at least one pathogenic agent. In certain embodiments, the antigen is derived from a tumor cell. In other embodiments, the antigen is derived from an infectious agent (e.g., virus, bacteria, fungus or parasite). In preferred embodiments, the antigen is derived from a human immunodeficiency virus (HIV) (e.g. gag, gp120, gp140, gp160 pol, rev, tat, and nef), a hepatitis C virus (HCV) (e.g., C, E1, E2, NS3, NS4 and NS5), an influenza virus (e.g., HA, NA, NP, M), a paramyxovirus such as parainfluenza virus or respiratory syncytial virus or measles virus (e.g., NP, M, F, HN, H), a herpes virus (e.g., glycoprotein B, glycoprotein D), a Filovirus such as Marburg or Ebola virus (e.g., NP, GP), a bunyavirus such as Hantaan virus or Rift Valley fever virus (e.g., G1, G2, N), or a flavivirus such as tick-borne encephalitis virus or West Nile virus (e.g., C, prM, E, NS1, NS3, NS5). Any of the methods described herein can further comprise the step of administering a lymphokine, chemokine and/or cytokine (e.g., IL-2, IL-10, IL-12, gamma interferon, GM-CSF, M-CSF, SLC, MIP3α, and MIP3β). The lymphokine, chemokine and/or cytokine can be administered as a polypeptide or can be encoded by a polynucleotide (e.g. on the same or a different replicon that encodes the antigen(s)). Alternatively, a replicon particle of the present invention encoding a lymphokine, chemokine and/or cytokine may be used as a to stimulate an immune response.

In yet other aspects, methods are provided for stimulating an immune response within a warm-blooded animal (e.g., an alphavirus-specific immune response), comprising the step of administering to a warn-blooded animal a composition comprising chimeric alphavirus particles described herein, for example alphavirus particles containing an alphavirus genome RNA that is either unmodified (e.g. naturally occurring) or modified (e.g., insertion of a heterologous packaging signal into a region of nonstructural protein deletion).

Thus, in any of the compositions and methods described herein, sequences and/or structural proteins are derived from at least two alphaviruses, for example Venezuelan equine encephalitis virus (VEE) and Sindbis virus (SIN).

In other aspects, methods are provided to produce alphavirus replicon particles and reduce the probability of generating replication-competent virus (e.g. wild-type virus) during production of said particles, comprising introducing into a permissible cell an alphavirus replicon RNA and one or more defective helper RNA(s) encoding at least one alphavirus structural protein, and incubating said cell under suitable conditions for a time sufficient to permit production of replicon particles, wherein said replicon RNA comprises a 5' sequence required for nonstructural protein-mediated amplification, sequences which, when expressed, code for biologically active alphavirus nonstructural proteins, a means to express one or more heterologous sequences, a heterologous sequence that is a protein-encoding gene, said gene being the 3' proximal gene within the replicon, a 3' sequence required for nonstructural protein-mediated amplification, a polyadenylate tract, and optionally a subgenomic 5'-NTR; and wherein said defective helper RNA comprises a 5' sequence required for nonstructural protein-mediated amplification, a means to express one or more alphavirus structural proteins, a sequence encoding one or more alphavirus structural proteins, the sequence encoding the 3' proximal gene within the defective helper, a 3' sequence required for nonstructural protein-mediated amplification, a polyadenylate tract, and optionally a subgenomic 5'-NTR; and wherein said replicon RNA differs from at least one defective helper RNA in at least one element selected from the group consisting of a 5' sequence required for nonstructural protein-mediated amplification, a means for expressing a 3' proximal gene, a subgenomic 5' NTR, and a 3' sequence required for nonstructural protein-mediated amplification.

In another aspect, provided herein is an alphavirus replicon RNA encoding nonstructural proteins from at least one alphavirus and one or more heterologous sequence(s) (e.g., a sequence encoding a therapeutic agent, an immunogen, etc.), wherein said replicon encodes a modified nsP4 polypeptide and wherein said replicon does not comprise sequences encoding alphavirus structural proteins. One or more amino acids may be modified (e.g., deleted, added and/or replaced) at one or more residues of the nsP4 polypeptide. In certain embodiments, the modification(s) is(are) in a conserved region of nsP4, for example in the region corresponding to amino acid residues 363 to 404, numbered relative to SIN (or any region or amino acids therein including but not limited to one or more of the amino acids in the region corresponding to amino acid residues 387 to 394, numbered relative to SIN). Any of the particles described herein may comprise, in 5' to 3' order (i) a 5' sequence required for nonstructural protein-mediated amplification, (ii) a nucleotide sequence encoding alphavirus nonstructural proteins, (iii) a means for expressing a heterologous nucleic acid, (iv) the heterologous nucleic acid sequence, (v) a 3' sequence required for nonstructural protein-mediated amplification, and (vi) a polyadenylate tract, wherein said heterologous nucleic acid sequence replaces an alphavirus structural protein gene.

In yet another aspect, the invention includes an alphavirus particle comprising any of the alphavirus replicon RNAs described herein. In any of the alphavirus replicons and/or particles containing these replicons, some or all of the sequences can be derived from Venezuelan equine encephalitis virus (VEE), Sindbis (SIN), Semliki Forest virus (SFV) or combinations of these and other alphaviruses.

In yet another aspect, provided herein is a method for producing alphavirus replicon particles, comprising introducing into a host cell (a) an alphavirus replicon RNA as described herein (e.g., an alphavirus replicon RNA encoding nonstructural proteins from at least one alphavirus and one or more heterologous sequence(s), wherein said replicon encodes a modified nsP4 polypeptide and wherein said replicon does not comprise sequences encoding alphavirus structural proteins); and (b) at least one separate defective helper RNA(s) encoding alphavirus structural protein(s) absent from the replicon RNA, wherein alphavirus replicon particles are produced.

In yet another aspect, described herein is a method of generating an immune response in a mammal by administering an alphavirus replicon as described herein to the mammal, thereby generating an immune response.

These and other aspects and embodiments of the invention will become evident upon reference to the following detailed description, attached figures and various references set forth herein that describe in more detail certain procedures or compositions (e.g., plasmids, sequences, etc.).

BRIEF DESCRIPTION OF THE FIGURES

FIG. 2 depicts the oligonucleotide-based synthesis of VEE nsP fragment 2. (SEQ ID NO 51 and SEQ ID NO 52).

FIG. 4 depicts hybrid capsid protein for the efficient production of chimeric Sindbis virus (SIN)/VEE alphavirus particles (SEQ ID NOS: 83 to 88).

FIG. 5 depicts hybrid E2 glycoprotein for the efficient production of chimeric SIN/VEE alphavirus particles (SEQ ID NOS: 89 to 94).

FIG. 6 depicts VEE replicons with heterologous SIN packaging signal for efficient packaging using SIN structural proteins.

FIG. 7 depicts SIN packaging signal insertion at nsP4/truncated junction region promoter (SEQ ID NOS: 95 and 96) (as used in Chimera 1A made in accordance with the teachings of the present invention).

FIG. 8 depicts SIN packaging signal insertion at nsP4/non-truncated junction region promoter (SEQ ID NO: 97) (as used in Chimera 1B made in accordance with the teachings of the present invention).

FIG. 14 depicts an alignment of the amino acid sequences of a portion of polymerases of several viruses, including alphaviruses (SIN, VEE and SFV) and a plant virus (BMV) (SEQ ID NOS: 79 to 82). The amino acid number shown in parentheses refers to the first amino acid shown in FIG. 14, numbered relative to the wild-type amino acid sequence of the virus shown.

DETAILED DESCRIPTION OF THE INVENTION

Figure 1:
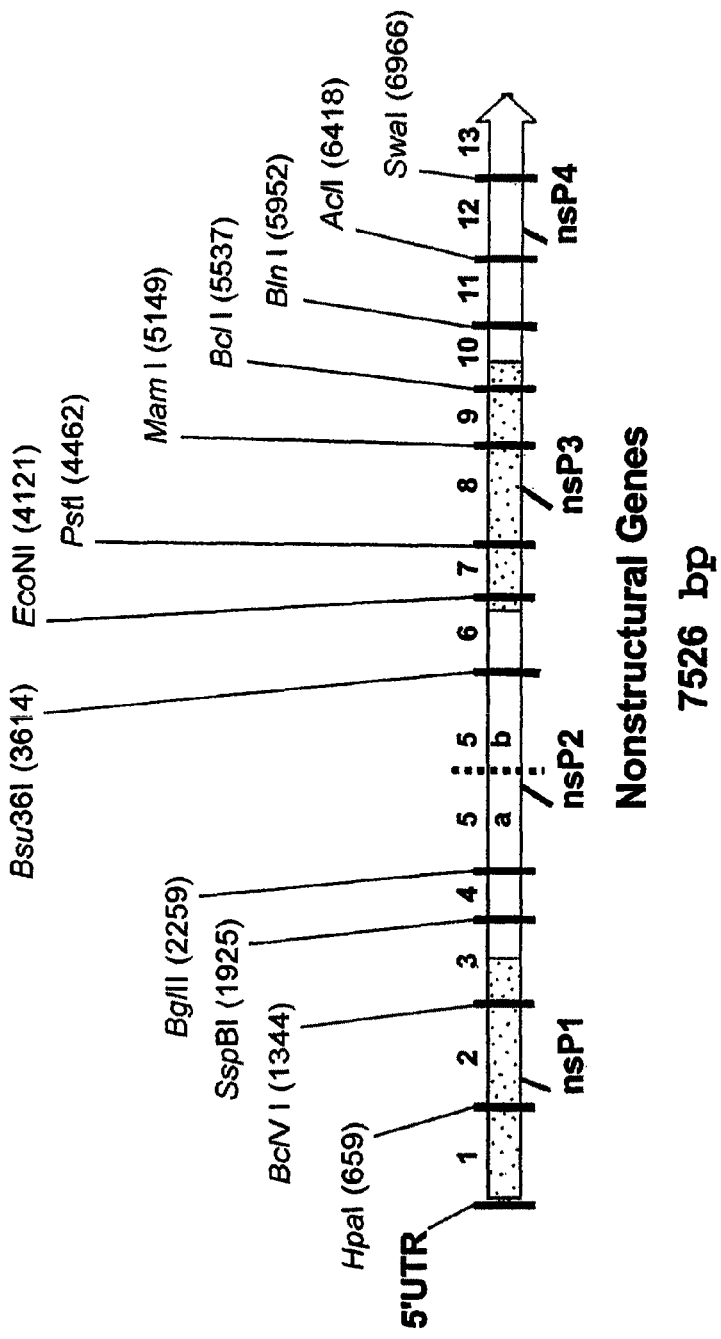
FIG. 1 depicts Venezuelan equine encephalitis virus (VEE) gene synthesis fragments and restriction sites used for assembly of a VEE replicon.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S. ed., CRC Press, 1997); *Short Protocols in Molecular Biology*, 4th ed. (Ausubel et al. eds., 1999, John Wiley & Sons); *Molecular Biology Techniques: An Intensive Laboratory Course* (Ream et al., eds., 1998, Academic Press); *PCR (Introduction to Biotechniques Series)*, 2nd ed. (Newton & Graham eds., 1997, Springer Verlag); Peters and Dalrymple, *Fields Virology*, 2nd ed., Fields et al. (eds.) (B.N. Raven Press, New York, N.Y.).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "a particle" includes a mixture of two or more such particles.

Prior to setting forth the invention definitions of certain terms that will be used hereinafter are set forth.

A "nucleic acid" molecule can include, but is not limited to, prokaryotic sequences, eukaryotic mRNA or other RNA, cDNA from eukaryotic mRNA or other RNA, genomic DNA sequences from eukaryotic (e.g., mammalian) DNA, and even synthetic DNA sequences. The term also captures sequences that include any of the known base analogs of DNA and RNA and includes modifications such as deletions, additions and substitutions (generally conservative in nature), to the native sequence. These modifications may be deliberate, as through site-directed mutagenesis, or may be accidental. Modifications of polynucleotides may have any number of effects including, for example, facilitating expression of the polypeptide product in a host cell.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein that includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts that produce the proteins or errors due to PCR amplification. Furthermore, modifications may be made that have one or more of the following effects: reducing toxicity; facilitating cell processing (e.g., secretion, antigen presentation, etc.); and facilitating presentation to B-cells and/or T-cells. The terms "polypeptide," and "protein" are used interchangeably herein to denote any polymer of amino acid residues. The terms encompass peptides, oligopeptides, dimers, multimers, and the like. Such polypeptides can be derived from natural sources or can be synthesized or recombinantly produced. The terms also include postexpression modifications of the polypeptide, for example, glycosylation, acetylation, phosphorylation, etc.

A polypeptide as defined herein is generally made up of the 20 natural amino acids Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y) and Val (V) and may also include any of the several known amino acid analogs, both naturally occurring and synthesized analogs, such as but not limited to homoisoleucine, asaleucine, 2-(methylenecyclopropyl)glycine, S-methylcysteine, S-(prop-1-enyl)cysteine, homoserine, ornithine, norleucine, norvaline, homoarginine, 3-(3-carboxyphenyl)alanine, cyclohexylalanine, mimosine, pipecolic acid, 4-methylglutamic acid, canavanine, 2,3-diaminopropionic acid, and the like. Further examples of polypeptide agents that will find use in the present invention are set forth below.

By "wild type" polypeptide, polypeptide agent or polypeptide drug, is meant a naturally occurring polypeptide sequence (and, optionally, its corresponding secondary structure). An "isolated" or "purified" protein or polypeptide is a protein that is separate and discrete from a whole organism with which the protein is normally associated in nature. It is apparent that the term denotes proteins of various levels of purity. Typically, a composition containing a purified protein will be one in which at least about 35%, preferably at least about 40-50%, more preferably, at least about 75-85%, and most preferably at least about 90% or more, of the total protein in the composition will be the protein in question.

By "nsP4 polypeptide" is meant a molecule derived from a non-structural protein 4 region of a virus polyprotein. nsP4 polypeptides are generally expressed as part of an alphavirus nonstructural polyprotein that is subsequently cleaved post-translationally. Alphaviral nsP4 polypeptides typically exhibit polymerase activity within an alphavirus replicase complex. The nsP4 sequence has been published for a variety of alphaviruses (e.g., Strauss et al., 1984, Virology 133:92-110; Takkinen 1986, Nucleic Acids Res. 14:5667-5682; Kinney et al., 1989, Virology, 170:19-30). The polypeptide sequence of nsP4 is generally of similar length among alphaviruses (e.g., 607 amino acids for VEE, 610 amino acids for SIN, 614 amino acids for SFV) and the overall sequence is generally well conserved among the alphaviruses, based on alignment of published sequences (Kinney, ibid). Specific amino acids sequences contemplated for modification according to the present invention can be found for example in any region, particularly regions exhibiting high sequence homology. Non-limiting examples of such regions correspond to SIN nsP4 amino acids 1-17, 59-76, 101-111, 120-153, 157-177, 180-240, 255-360, 362-412, 414-417, 419-454, 459-510, 512-535 and 539-549, numbered relative to a wild-type SIN (e.g., Strauss et al. (1984) *Virology* 133:92-110). FIG. 14 depicts an alignment of regions of nsP4 from SIN, VEE, and SFV, as well as BMV2a, encompassing SIN amino acids 361-405. Furthermore, an "nsP4 polypeptide" as defined herein is not limited to a polypeptide having the exact sequence described herein. Indeed, alphaviral genomes are often in flux and contain several variable domains that exhibit relatively high degrees of variability between species and isolated. It is readily apparent that the terms encompass nsP4 polypeptides from any of the identified alphaviruses, as well as newly identified isolates, and subtypes of these isolates. Descriptions of structural features are typically given herein with reference to a Sindbis virus, for example the SIN sequence described in Strauss et al. (1984) *Virology* 133:92-110. One of ordinary skill in the art in view of the teachings of the present disclosure and the art can determine corresponding regions in other alphaviruses (e.g., VEE, SFV, WEE, etc) (see, e.g., Virology, 3rd Edition (W. K. Joklik ed. 1988); *Fundamental Virology,* 2nd Edition (B. N. Fields and D. M. Knipe, eds. 1991); *Virology,* 3rd Edition (Fields, B N, D M Knipe, P M Howley, Editors, 1996, Lippincott-Raven, Philadelphia, Pa.; for a description of these and other related viruses and Weaver et al. (1993) *Virology* 197:375-390 and Weaver et al. (1994) *Virology* 202:1083 for a comparison of various alphavirus nucleotide sequences), using for example, sequence comparison programs (e.g., BLAST and others described herein) or identification and alignment of structural features (e.g., a program such as the "ALB" program described herein that can identify polymerase regions). The actual amino acid sequences of the modified nsP4 sequences can be based on any alphavirus.

Additionally, the term "nsP4 polypeptide" encompasses proteins or sequences encoding these proteins that include additional modifications to the native sequence, such as additional internal deletions; additions and substitutions. These modifications may be deliberate, as through site-directed mutagenesis, or may be accidental, such as through naturally occurring mutational events. Thus, a "modified nsP4 polypeptide" is an nsP4 polypeptide that has been manipulated to delete or replace one, more than one or all of the amino acid residues in the polymerase region of the polypeptide. Similarly, the term "modified nsP4-encoding sequence" refers to a polynucleotide sequence that encodes a modified nsP4 polypeptide. Generally, modified nsP4 polypeptides as described herein, typically result in the reduction or elimination of inter-strand transfer. Further, it is to be understood that other modifications of nsP4 are also encompassed by the present invention.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman (*Advances in Applied Mathematics* 2:482-489 (1981)). This algorithm can be extended to use with peptide sequences using the scoring matrix developed by Dayhoff (*Atlas of Protein Sequences and Structure*, M. O. Dayhoff ed., 5 suppl. 3:353-358, National Biomedical Research Foundation, Washington, D.C., USA), and normalized by Gribskov (*Nucl. Acids Res.* 14(6):6745-6763 (1986)). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10-12 nucleotides and up to 5000 nucleotides, and even more preferably 15-20 nucleotides, up to the number of nucleotides present in the full-length sequences described herein (e.g., see the Sequence Listing and claims), including all integer values falling within the above-described ranges.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook et al., *Molecular Cloning: A Laboratory Manual*, Second Edition, 1989 (Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, 1985 (Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al. *Molecular Cloning: A Laboratory Manual*, Second Edition (1989) (Cold Spring Harbor, N.Y.).

The term "derived from" is used to identify the alphaviral source of molecule (e.g., polynucleotide, polypeptide). A first polynucleotide is "derived from" second polynucleotide if it has the same or substantially the same basepair sequence as a region of the second polynucleotide, its cDNA, complements thereof, or if it displays sequence identity as described above. Thus, an alphavirus sequence or polynucleotide is "derived from" a particular alphavirus (e.g., species) if it has (i) the same or substantially the same sequence as the alphavirus sequence or (ii) displays sequence identity to polypeptides of that alphavirus as described above.

A first polypeptide is "derived from" a second polypeptide if it is (i) encoded by a first polynucleotide derived from a second polynucleotide, or (ii) displays sequence identity to the second polypeptides as described above. Thus, an alphavirus polypeptide (protein) is "derived from" a particular alphavirus if it is (i) encoded by an open reading frame of a polynucleotide of that alphavirus (alphaviral polynucleotide), or (ii) displays sequence identity, as described above, to polypeptides of that alphavirus.

Both polynucleotide and polypeptide molecules can be physically derived from the alphavirus or produced recombinantly or synthetically, for example, based on known sequences.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), translation termination sequences, 5' sequence required for nonstructural protein-mediated amplification, 3' sequence required for nonstructural protein-mediated amplification, and means to express one or more heterologous sequences (e.g., subgenomic junction region promoter), see e.g., McCaughan et al. (1995) *Proc. Natl. Acad. Sci. USA* 92:5431-5435; Kochetov et al. (1998) *FEBS Letts.* 440:351-355.

"Alphavirus RNA replicon vector", "RNA replicon vector", "replicon vector" or "replicon" refers to an RNA molecule that is capable of directing its own amplification or self-replication in vivo, within a target cell. To direct its own amplification, the RNA molecule should encode the polymerase(s) necessary to catalyze RNA amplification (e.g., alphavirus nonstructural proteins nsP1, nsP2, nsP3, nsP4) and also contain cis RNA sequences required for replication which are recognized and utilized by the encoded polymerase(s). An alphavirus RNA vector replicon should contain the following ordered elements: 5' viral or cellular sequences required for nonstructural protein-mediated amplification (may also be referred to as 5' CSE, or 5' cis replication sequence, or 5' viral sequences required in cis for replication, or 5' sequence which is capable of initiating transcription of an alphavirus), sequences which, when expressed, code for biologically active alphavirus nonstructural proteins (e.g., nsP1, nsP2, nsP3, nsP4), and 3' viral or cellular sequences required for nonstructural protein-mediated amplification (may also be referred as 3' CSE, or 3' viral sequences required in cis for replication, or an alphavirus RNA polymerase recognition sequence). The alphavirus RNA vector replicon also should contain a means to express one or more heterologous sequence(s), such as for example, an IRES or a viral (e.g., alphaviral) subgenomic promoter (e.g., junction region promoter) which may, in certain embodiments, be modified in order to increase or reduce viral transcription of the subgenomic fragment, or to decrease homology with defective helper or structural protein expression cassettes, and one or more heterologous sequence(s) to be expressed. A replicon can also contain additional sequences, for example, one or more heterologous sequence(s) encoding one or more polypeptides (e.g., a protein-encoding gene or a 3' proximal gene) and/or a polyadenylate tract.

"Recombinant alphavirus particle", "alphavirus replicon particle" and "replicon particle" refer to a virion-like unit containing an alphavirus RNA vector replicon. Generally, the recombinant alphavirus particle comprises one or more alphavirus structural proteins, a lipid envelope and an RNA vector replicon. Preferably, the recombinant alphavirus particle contains a nucleocapsid structure that is contained within a host cell-derived lipid bilayer, such as a plasma membrane, in which one or more alphaviral envelope glycoproteins (e.g., E2, E1) are embedded. The particle may also contain other components (e.g., targeting elements such as biotin, other viral structural proteins or portions thereof, hybrid envelopes, or other receptor binding ligands), which direct the tropism of the particle from which the alphavirus was derived. Generally, the interaction between alphavirus RNA and structural protein(s) necessary to efficiently form a replicon particle or nucleocapsid may be an RNA-protein interaction between a capsid protein and a packaging signal (or packaging sequence) contained within the RNA.

"Alphavirus packaging cell line" refers to a cell which contains one or more alphavirus structural protein expression cassettes and which produces recombinant alphavirus particles (replicon particles) after introduction of an alphavirus RNA vector replicon, eukaryotic layered vector initiation system, or recombinant alphavirus particle. The parental cell may be of mammalian or non-mammalian origin. Within preferred embodiments, the packaging cell line is stably transformed with the structural protein expression cassette(s).

"Defective helper RNA" refers to an RNA molecule that is capable of being amplified and expressing one or more alphavirus structural proteins within a eukaryotic cell, when that cell also contains functional alphavirus nonstructural "replicase" proteins. The alphavirus nonstructural proteins may be expressed within the cell by an alphavirus RNA replicon vector or other means. To permit amplification and structural protein expression, mediated by alphavirus nonstructural proteins, the defective helper RNA molecule should contain 5'-end and 3'-end RNA sequences required for amplification, which are recognized and utilized by the nonstructural proteins, as well as a means to express one or more alphavirus structural proteins. Thus, an alphavirus defective helper RNA should contain the following ordered elements: 5' viral or cellular sequences required for RNA amplification by alphavirus nonstructural proteins (also referred to elsewhere as 5' CSE, or 5' cis replication sequence, or 5' viral sequences required in cis for replication, or 5' sequence which is capable of initiating transcription of an alphavirus), a means to express one or more alphavirus structural proteins, gene sequence(s) which, when expressed, codes for one or more alphavirus structural proteins (e.g., C, E2, E1), 3' viral or cellular sequences required for amplification by alphavirus nonstructural proteins (also referred to as 3' CSE, or 3' viral sequences required in cis for replication, or an alphavirus RNA polymerase recognition sequence), and a preferably a polyadenylate tract. Generally, the defective helper RNA should not itself encode or express in their entirety all four alphavirus nonstructural proteins (nsP1, nsP2, nsP3, nsP4), but may encode or express a subset of these proteins or portions thereof, or contain sequence(s) derived from one or more nonstructural protein genes, but which by the nature of their inclusion in the defective helper do not express nonstructural protein(s) or portions thereof. As a means to express alphavirus structural protein(s), the defective helper RNA may contain a viral (e.g., alphaviral) subgenomic promoter which may, in certain embodiments, be modified to modulate transcription of the subgenomic fragment, or to decrease homology with replicon RNA, or alternatively some other means to effect expression of the alphavirus structural protein (e.g., internal ribosome entry site, ribosomal readthrough element). Preferably an alphavirus structural protein gene is the 3' proximal gene within the defective helper. In addition, it is also preferable that the defective helper RNA does not contain sequences that facilitate RNA-protein interactions with alphavirus structural protein(s) and packaging into nucleocapsids, virion-like particles or alphavirus replicon particles. A defective helper RNA is one specific embodiment of an alphavirus structural protein expression cassette.

"Eukaryotic Layered Vector Initiation System" refers to an assembly that is capable of directing the expression of a sequence or gene of interest. The eukaryotic layered vector initiation system should contain a 5' promoter that is capable of initiating in vivo (i.e. within a eukaryotic cell) the synthesis of RNA from cDNA, and a nucleic acid vector sequence (e.g., viral vector) that is capable of directing its own replication in a eukaryotic cell and also expressing a heterologous sequence. Preferably, the nucleic acid vector sequence is an alphavirus-derived sequence and is comprised of 5' viral or cellular sequences required for nonstructural protein-mediated amplification (also referred to as 5' CSE, or 5' cis replication sequence, or 5' viral sequences required in cis for replication, or 5' sequence which is capable of initiating transcription of an alphavirus), as well as sequences which, when expressed, code for biologically active alphavirus nonstructural proteins (e.g., nsP1, nsP2, nsP3, nsP4), and 3' viral or cellular sequences required for nonstructural protein-mediated amplification (also referred to as 3' CSE, or 3' viral sequences required in cis for replication, or an alphavirus RNA polymerase recognition sequence). In addition, the vector sequence may include a means to express heterologous sequence(s), such as for example, a viral (e.g., alphaviral) subgenomic promoter (e.g., junction region promoter) which may, in certain embodiments, be modified in order to prevent, increase, or reduce viral transcription of the subgenomic fragment, or to decrease homology with defective helper or structural protein expression cassettes, and one or more heterologous sequence(s) to be expressed. Preferably the heterologous sequence(s) comprises a protein-encoding gene and said gene is the 3' proximal gene within the vector sequence. The eukaryotic layered vector initiation system may also contain a polyadenylation sequence, splice recognition sequences, a catalytic ribozyme processing sequence, a nuclear export signal, and a transcription termination sequence. In certain embodiments, in vivo synthesis of the vector nucleic acid sequence from cDNA may be regulated by the use of an inducible promoter or subgenomic expression may be inducible through the use of translational regulators or modified nonstructural proteins.

As used herein, the terms “chimeric alphavirus particle” and “chimeric alphavirus replicon particle” refer to a chimera or chimeric particle such as a virus, or virus-like particle, specifically modified or engineered to contain a nucleic acid derived from a alphavirus other than the alphavirus from which either the capsid and/or envelope glycoprotein was derived (e.g., from a different virus). In such a particle, the nucleic acid derived from an alphavirus is an RNA molecule comprising one of any number of different lengths, including, but not limited to genome-length (encoding nonstructural and structural proteins) and replicon-length (deleted of one or more structural proteins). For example, and not intended as a limitation, chimeric replicon particles made in accordance with the teachings of the present invention include Sindbis virus (SIN) replicon RNA within a capsid having a Sindbis virus RNA binding domain and a Venezuelan equine encephalitis virus (VEE) envelope glycoprotein interaction domain, surrounded by a VEE glycoprotein envelope and a VEE replicon RNA having a deletion in nsP3, a SIN packaging signal inserted into the deletion in nsP3 and capsid and envelope proteins derived from SIN.

The term “3' Proximal Gene” refers to a nucleotide sequence encoding a protein, which is contained within a replicon vector, Eukaryotic Layered Vector Initiation System, defective helper RNA or structural protein expression cassette, and located within a specific position relative to another element. The position of this 3' proximal gene should be determined with respect to the 3' sequence required for nonstructural protein-mediated amplification (defined above), wherein the 3' proximal gene is the protein-encoding sequence 5' (upstream) of, and immediately preceding this element. The 3' proximal gene generally is a heterologous sequence (e.g., antigen-encoding gene) when referring to a replicon vector or Eukaryotic Layered Vector Initiation System, or alternatively, generally is a structural protein gene (e.g., alphavirus C, E2, E1) when referring to a defective helper RNA or structural protein expression cassette.

The term “5' viral or cellular sequences required for nonstructural protein-mediated amplification” or “5' sequences required for nonstructural protein-mediated amplification” refers to a functional element that provides a recognition site at which the virus or virus-derived vector synthesizes positive strand RNA. Thus, it is the complement of the actual sequence contained within the virus or vector, which corresponds to the 3' end of the of the minus-strand RNA copy, which is bound by the nonstructural protein replicase complex, and possibly additional host cell factors, from which transcription of the positive-strand RNA is initiated. A wide variety of sequences may be utilized for this function. For example, the sequence may include the alphavirus 5'-end nontranslated region (NTR) and other adjacent sequences, such as for example sequences through nucleotides 210, 250, 300, 350, 400, or 450. Alternatively, non-alphavirus or other sequences may be utilized as this element, while maintaining similar functional capacity, for examples in the case of SIN, nucleotides 10-75 for tRNA Asparagine (Schlesinger et al., U.S. Pat. No. 5,091, 309). The term is used interchangeably with the terms 5' CSE, or 5' viral sequences required in cis for replication, or 5' sequence that is capable of initiating transcription of an alphavirus.

The term “viral subgenomic promoter” refers to a sequence of virus origin that, together with required viral and cellular polymerase(s) and other factors, permits transcription of an RNA molecule of less than genome length. For an alphavirus (alphaviral) subgenomic promoter or alphavirus (alphaviral) subgenomic junction region promoter, this sequence is derived generally from the region between the nonstructural and structural protein open reading frames (ORFs) and normally controls transcription of the subgenomic mRNA. Typically, the alphavirus subgenomic promoter consists of a core sequence that provides most promoter-associated activity, as well as flanking regions (e.g., extended or native promoter) that further enhance the promoter-associated activity. For example, in the case of the alphavirus prototype, Sindbis virus, the normal subgenomic junction region promoter typically begins at approximately nucleotide number 7579 and continues through at least nucleotide number 7612 (and possibly beyond). At a minimum, nucleotides 7579 to 7602 are believed to serve as the core sequence necessary for transcription of the subgenomic fragment.

The terms “3' viral or cellular sequences required for nonstructural protein-mediated amplification” or “3' sequences required for nonstructural protein-mediated amplification” are used interchangeably with the terms 3° CSE, or 3' cis replication sequences, or 3' viral sequences required in cis for replication, or an alphavirus RNA polymerase recognition sequence. This sequence is a functional element that provides a recognition site at which the virus or virus-derived vector begins replication (amplification) by synthesis of the negative RNA strand. A wide variety of sequences may be utilized for this function. For example, the sequence may include a complete alphavirus 3'-end non-translated region (NTR), such as for example, with SIN, which would include nucleotides 11,647 to 11,703, or a truncated region of the 3' NTR, which still maintains function as a recognition sequence (e.g., nucleotides 11,684 to 11,703). Other examples of sequences that may be utilized in this context include, but are not limited to, non-alphavirus or other sequences that maintain a similar functional capacity to permit initiation of negative strand RNA synthesis (e.g., sequences described in George et al. (2000) *J. Virol.* 74:9776-9785).

An “antigen” refers to a molecule containing one or more epitopes (either linear, conformational or both) that will stimulate a host's immune system to make a humoral and/or cellular antigen-specific response. The term is used interchangeably with the term "immunogen." Normally, an epitope will include between about 3-15, generally about 5-15 amino acids. A B-cell epitope is normally about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes as well as tumor antigens, including extracellular domains of cell surface receptors and intracellular portions that may contain T-cell epitopes. Antibodies such as anti-idiotype antibodies, or fragments thereof, and synthetic peptide mimotopes, which can mimic an antigen or antigenic determinant, are also captured under the definition of antigen as used herein. Singularly, an oligonucleotide or polynucleotide that expresses an antigen or antigenic determinant in vivo, such as in gene therapy and DNA immunization applications, is also included in the definition of antigen herein.

Epitopes of a given protein can be identified using any number of epitope mapping techniques, well known in the art. See, e.g., *Epitope Mapping Protocols in Methods in Molecular Biology*, Vol. 66 (Glenn E. Morris, Ed., 1996) (Humana Press, Totowa, N.J.). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Nat'l Acad Sci. USA* 81:39984002; Geysen et al. (1986) *Molec. Immunol* 23:709-715, all incorporated herein by reference in their entireties.

Similarly, conformational epitopes are readily identified by determining spatial conformation of amino acids such as by, e.g., x-ray crystallography and nuclear magnetic resonance. See, e.g., *Epitope Mapping Protocols*, supra.

For purposes of the present invention, antigens can be derived from tumors and/or any of several known viruses, bacteria, parasites and fungi, as described more fully below. The term also intends any of the various tumor antigens or any other antigen to which an immune response is desired. Furthermore, for purposes of the present invention, an "antigen" refers to a protein that includes modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts that produce the antigens.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. In addition, a chemokine response may be induced by various white blood or endothelial cells in response to an administered antigen.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al. *J. Immunol.* (1993) 151:4189-4199; Doe et al. (1994) *Eur. J. Immunol.* 24:2369-2376. Recent methods of measuring cell-mediated immune response include measurement of intracellular cytokines or cytokine secretion by T-cell populations (e.g., by ELISPOT technique), or by measurement of epitope specific T-cells (e.g., by the tetramer technique) (reviewed by McMichael, A. J., and O'Callaghan, C. A. (1998) *J. Exp. Med.* 187(9):1367-1371; Mcheyzer-Williams, M. G. et al. (1996) *Immunol. Rev.* 150:5-21; Lalvani, A. et al. (1997) *J. Exp. Med.* 186:859-865).

Thus, an immunological response as used herein may be one that stimulates CTLs, and/or the production or activation of helper T-cells. The production of chemokines and/or cytokines may also be stimulated. The antigen of interest may also elicit an antibody-mediated immune response. Hence, an immunological response may include one or more of the following effects: the production of antibodies (e.g. IgA or IgG) by B-cells; and/or the activation of suppressor, cytotoxic, or helper T-cells and/or (* T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule (or nucleotide sequence encoding an antigenic molecule) where administration of the composition to a subject results in the development in the subject of a humoral and/or a cellular and/or mucosal immune response to the antigenic molecule of interest. The immunogenic composition can be introduced directly into a recipient subject, such as by injection, inhalation, oral, intranasal or any other parenteral or mucosal (e.g., intra-rectally or intra-vaginally) route of administration.

By "subunit vaccine" is meant a vaccine composition that includes one or more selected antigens but not all antigens, derived from or homologous to, an antigen from a pathogen of interest such as from a virus, bacterium, parasite or fungus. Such a composition is substantially free of intact pathogen cells or pathogenic particles, or the lysate of such cells or particles. Thus, a "subunit vaccine" can be prepared from at least partially purified (preferably substantially purified) immunogenic polypeptides from the pathogen, or analogs thereof. The method of obtaining an antigen included in the subunit vaccine can thus include standard purification techniques, recombinant production, or synthetic production.

1.0. Introduction

Several members of the alphavirus genus are being developed as gene delivery systems for vaccine and other therapeutic applications (Schlesinger and Dubensky (1999) *Curr. Opin. Biotechnol.* 10:434439). The typical "replicon" configuration of alphavirus vector constructs, as described in more detail above and in U.S. Pat. Nos. 5,789,245; 5,843,723; 5,814,482; and 6,015,694; and WO 00/61772, comprises a 5' sequence which initiates transcription of alphavirus RNA, a nucleotide sequence encoding alphavirus nonstructural proteins, a viral subgenomic junction region promoter which directs the expression of an adjacent heterologous nucleic acid sequence, an RNA polymerase recognition sequence and preferably a polyadenylate tract. Other terminology to define the same elements is also known in the art.

Often, for in vivo vaccine and therapeutic applications, the alphavirus RNA replicon vector or replicon RNA is first packaged into a virus-like particle, comprising the alphavirus structural proteins (e.g., capsid protein and envelope glycoproteins). Because of their configuration, vector replicons do not express these alphavirus structural proteins necessary for packaging into recombinant alphavirus replicon particles. Thus, to generate replicon particles, the structural proteins must be provided in trans. Packaging may be accomplished by a variety of methods, including transient approaches such as co-transfection of in vitro transcribed replicon and defective helper RNA(s) (Liljestrom (1991) *Bio/Technology* 9:1356-1361; Bredenbeek et al. (1993) *J. Virol.* 67:6439-6446; Frolov et al. (1997) *J. Virol.* 71:2819-2829; Pushko et al. (1997) *Virology* 239:389-401; U.S. Pat. Nos. 5,789,245 and 5,842,723) or plasmid DNA-based replicon and defective helper constructs (Dubensky et al. (1996) *J. Virol.* 70:508-519), as well as introduction of alphavirus replicons into stable packaging cell lines (PCL) (Polo et al. (1999) *Proc. Natl. Acad. Sci. USA* 96:4598-4603; U.S. Pat. Nos. 5,789,245; 5,842,723; 6,015,694; WO 9738087 and WO 9918226).

The trans packaging methodologies permit the modification of one or more structural protein genes (for example, to incorporate sequences of alphavirus variants such as attenuated mutants U.S. Pat. Nos. 5,789,245; 5,842,723; 6,015,694), followed by the subsequent incorporation of the modified structural protein into the final replicon particles. In addition, such packaging permits the overall modification of alphavirus replicon particles by packaging of a vector construct or RNA replicon from a first alphavirus using structural proteins from a second alphavirus different from that of the vector construct (WO 95/07994; Polo et al. (1999), ibid; Gardner et al. (2000) *J. Virol.* 74:11849-11857). This approach provides a mechanism to exploit desirable properties from multiple alphaviruses in a single replicon particle. For example, while all alphaviruses are generally quite similar in their overall mechanisms of replication and virion structure, the various members of the alphavirus genus can exhibit some unique differences in their biological properties in vivo (e.g., tropism for lymphoid cells, interferon sensitivity, disease profile). Furthermore, a number of alphaviruses are classified as Biosafety Level 3 (BSL-3) organisms, which is an issue for particle production (e.g., manufacturing) facilities and possible human use, while others are classified as Biosafety Level 2 (BL-2). Alphavirus replicon particle chimeras provide a mechanism to include particular properties of a BSL-3 level alphavirus in a replicon particle derived from a BL-2 level virus. For example, elements from the BSL-3 lymphotropic Venezuelan equine encephalitis virus (VEE) may be incorporated into a non-naturally lymphotropic BL-2 virus (e.g., Sindbis virus).

However, to date, there has been limited success in efficiently and routinely produce commercially acceptable high titer preparations of chimeric alphavirus particles. Such chimeric alphavirus particles are desirable for several reasons including specified tropisms or tissue specificity, altered surface antigenicity and altered recognition by the host. In this regard, an animal's immune system generally recognizes viral surface antigens, such as the envelope glycoproteins, and directs specific cellular and humoral responses against them long before internal viral antigens such as capsid proteins are exposed to the immune system. Consequently, if a replicon particle recipient has pre-existing antibodies directed against the vector's surface antigens (a sensitized host) the replicon particle may be attacked and destroyed before it could deliver its therapeutic payload to the target tissue. Given that many of the most successful replicon particles are derived from naturally occurring, infectious viruses, it is likely that at least some potential replicon particle recipients have been previously exposed to, and developed immune responses against, surface antigens that are common between the replicon particle and the natural infectious virus. The likelihood of an adverse immune response is also increased upon multiple administrations. Therefore, in order reduce or eliminate this possibility, subsequent gene delivery replicon particles can be made using chimeric replicon particles so the recipient is not required to see the same structural proteins multiple times.

Described herein are chimeric alphavirus particles that exhibit efficient structural interactions. Thus, the present invention provides compositions and methods for constructing and obtaining recombinant chimeric alphavirus particles with significantly increased efficiencies of packaging/production, for example using SIN/VEE chimeras.

Advantages of the present invention include, but are not limited to, (i) providing chimeric alphavirus particles at commercially viable levels; (ii) the ability to reduce the likelihood of undesirable events occurring, for example, recombination and/or structural gene packaging; (iii) providing gene delivery vehicles with specific tissue and cell tropisms (e.g., antigen delivery to an antigen-presenting cell such as a dendritic cell).

The teachings provided herein allow one of skill in the art to construct chimeric alphavirus particles derived from a wide variety of different alphaviruses, particularly when sequences of such alphaviruses have already been published. Eukaryotic Layered Vector Initiation Systems (ELVIS) can also be designed using these chimeric compositions. By optimizing the levels of packaging as disclosed herein, chimeric alphavirus particles (e.g., replicon particles) may be produced for use in various applications including in vaccine and therapeutic applications.

2.0.0. Alphavirus Replicons and Particles

As noted above, chimeric particles as described herein typically include one or more polynucleotide sequences (e.g. RNA). When found in particles, these polynucleotides are surrounded by (and interact with) one or more structural proteins. Non-limiting examples of polynucleotide sequences and structural proteins that can be used in the practice of the invention are described herein.

2.1.0. Nucleotide Components

The particles, vectors and replicons described herein typically include a variety of nucleic acid sequences, both coding and non-coding sequences. It will be apparent that the chimeric compositions described herein generally comprise less than a complete alphavirus genome (e.g., contain less than all of the coding and/or non-coding sequences contained in a genome of an alphavirus).

Further, it should be noted that, for the illustration herein of various elements useful in the present invention, alphavirus sequences from a heterologous virus are considered as being derived from an alphavirus different from the alphavirus that is the source of nonstructural proteins used in the replicon to be packaged, regardless of whether the element being utilized is in the replicon or defective helper RNA (e.g., during particle production, when both are present).

2.1.1. Non-Coding Polynucleotide Components

The chimeric particles and replicons described herein typically contain sequences that code for polypeptides (e.g., structural or non-structural) as well as non-coding sequences, such as control elements. Non-limiting examples of non-coding sequences include 5' sequences required for nonstructural protein-mediated amplification, a means for expressing a 3' proximal gene, subgenomic mRNA 5'-end nontranslated region (subgenomic 5' NTR), and 3' sequences required for nonstructural protein-mediated amplification (U.S. Pat. Nos. 5,843,723; 6,015,694; 5,814,482; WO 97/38087; WO 00/61772). It will be apparent from the teachings herein that one, more than one or all of the sequences described herein can be included in the particles, vectors and/or replicons described herein and, in addition, that one or more of these sequences can be modified or otherwise manipulated according to the teachings herein.

Thus, the polynucleotides described herein typically include a 5' sequence required for nonstructural protein-mediated amplification. Non-limiting examples of suitable 5' sequences include control elements such as native alphavirus 5'-end from homologous virus, native alphavirus 5'-end from heterologous virus, non-native DI alphavirus 5'-end from homologous virus, non-native DI alphavirus 5'-end from heterologous virus, non-alphavirus derived viral sequence (e.g., togavirus, plant virus), cellular RNA derived sequence (e.g., tRNA element) (e.g., Monroe et al. (1983) *Proc. Natl. Acad. Sci. USA* 80:3279-3283), mutations/deletions of any of the above sequences to reduce homology (See, e.g., Niesters et al. (1990) *J. Virol.* 64:41624168; Niesters et al. (1990) *J. Virol.* 64:1639-1647), and/or minimal 5' sequence in helpers (to approx. 200, 250, 300, 350, 400 nucleotides).

The polynucleotide sequences also generally include a means for expressing a 3' proximal gene (e.g., a heterologous sequence, polypeptide encoding sequence). Non-limiting examples of such means include control elements such as promoters and the like, for example, a native alphavirus subgenomic promoter from homologous virus, a native alphavirus subgenomic promoter from heterologous virus, a core alphavirus subgenomic promoter (homologous or heterologous), minimal sequences upstream or downstream from core subgenomic promoter, mutations/deletions/additions of core or native subgenomic promoter, a non-alphavirus derived compatible subgenomic promoter (e.g. plant virus), an internal ribosome entry site (IRES), and/or a ribosomal readthrough element (e.g., BiP).

Suitable subgenomic mRNA 5'-end nontranslated regions (subgenomic 5' NTR) include, but are not limited to, a native alphavirus subgenomic 5'NTR from homologous virus, a native alphavirus subgenomic 5'NTR from heterologous virus, a non-alphavirus derived viral 5'NTR (e.g., plant virus), a cellular gene derived 5'NTR (e.g., β-globin), and/or sequences containing mutations, deletions, and/or additions to native alphavirus subgenomic 5'NTR.

Non-limiting examples of suitable 3' sequences required for nonstructural protein-mediated amplification include control elements such as a native alphavirus 3'-end from homologous virus, a native alphavirus 3'-end from heterologous virus, a non-native DI alphavirus 3'-end from homologous virus, a non-native DI alphavirus 3'-end from heterologous virus, a non-alphavirus derived viral sequence (e.g., togavirus, plant virus), a cellular RNA derived sequence, sequences containing mutations, deletions, or additions of above sequences to reduce homology (See, e.g., Kuhn et al. (1990) *J. Virol.* 64:1465-1476), minimal sequence in helpers to approx. (20, 30, 50, 100, 200 nucleotides) and/or sequences from cell-repaired 3' alphavirus CSE. A polyadenylation sequence can also be incorporated, for example, within 3'-end sequences. (See, e.g., George et al. (2000) *J. Virol.* 74:9776-9785).

2.1.2. Coding Sequences

The compositions described herein may also include one or more sequences coding for various alphavirus polypeptides, for example one or more of the non-structural (nsP1, nsP2, nsP3, nsP4) or structural (e.g., caspid, envelope) alphavirus polypeptides.

As described in Strauss et al. (1984), supra, a wild-type SIN genome is 11,703 nucleotides in length, exclusive of the 5' cap and the 3'-terminal poly(A) tract. After the 5'-terminal cap there are 59 nucleotides of 5' nontranslated nucleic acid followed by a reading frame of 7539 nucleotides that encodes the nonstructural polypeptides and which is open except for a single opal termination codon. Following 48 untranslated bases located in the junction region that separates the nonstructural and structural protein coding sequences, there is an open reading frame 3735 nucleotides long that encodes the structural proteins. Finally, the 3' untranslated region is 322 nucleotides long. The nonstructural proteins are translated from the genomic RNA as two polyprotein precursors. The first includes nsP1, nsP2 and nsP3 is 1896 amino acids in length and terminates at an opal codon at position 1897. The fourth nonstructural protein, nsP4, is produced when readthrough of the opal codon produces a second polyprotein precursor of length 2513 amino acids, which is then cleaved post-translationally.

The approximately boundaries that define the nonstructural protein genes from the genomes of three representative and commonly used alphaviruses, SIN, SFV and VEE as follows.

|  | SIN[1] | SFV[2] | VEE[3] |
| --- | --- | --- | --- |
| nsP1 (approx. nucleotide boundaries) | 60-1679 | 86-1696 | 45-1649 |
| nsP1 (approx. amino acid boundaries) | 1-540 | 1-537 | 1-535 |
| nsP2 (approx. nucleotide boundaries) | 1680-4100 | 1697-4090 | 1650-4031 |
| nsP2 (approx. amino acid boundaries) | 541-1347 | 538-1335 | 536-1329 |
| nsP3 (approx. nucleotide boundaries) | 4101-5747 | 4191-5536 | 4032-5681 |
| nsP3 (approx. amino acid boundaries) | 1348-1896 | 1336-1817 | 1330-1879 |
| nsP4 (approx. nucleotide boundaries) | 5769-7598 | 5537-7378 | 5703-7523 |

[1] Strauss et al. (1984) Virology 133: 92-110
[2] Takkinen (1986) Nucleic Acids Res. 14: 5667-5682
[3] Kinney et al. (1989) Virology 170: 19

A wild-type alphavirus genome also includes sequences encoding structural proteins. In SIN, the structural proteins are translated from a subgenomic message which begins at nucleotide 7598, is 4106 nucleotides in length (exclusive of the poly(A) tract), and is coterminal with the 3' end of the genomic RNA. Like the non-structural proteins, the structural proteins are also translated as a polyprotein precursor that is cleaved to produce a nucleocapsid protein and two integral membrane glycoproteins as well as two small peptides not present in the mature virion. Thus, the replicons, particles and vectors of the present invention can include sequences derived from one or more coding sequences of one or more alphaviruses.

In addition to providing for sequences derived from coding regions of alphaviruses, the present invention also provides for alphavirus replicon vectors containing sequences encoding modified alphavirus proteins, for example modified nonstructural proteins to reduce or eliminate their propensity for inter-strand transfer (e.g., recombination) between replicon and defective helper RNA, or between two defective helper RNAs, during positive-strand RNA synthesis, negative-strand RNA synthesis, or both. In the context of the production of alphavirus replicon particles, inter-strand transfer or recombination may lead to undesirable contamination with replication-competent virus in the preparation. Thus, it is desirable to limit or eliminate inter-strand transfer, for example using molecules described herein.

Modifications to alphavirus coding sequences may include, but are not limited to nucleotide mutations, deletions, additions, or sequence substitutions, in whole or in part, such as for example using a hybrid nonstructural protein comprising sequences from one alphavirus and another virus (e.g., alphavirus, togavirus, plant virus).

Thus, a variety of sequence modifications are contemplated within the present invention. For example, in certain embodiments, there are one or more deletions in sequences encoding nonstructural protein gene(s). Such deletions may be in nonstructural protein (nsP) 1, 2, 3, or 4, as well as combinations of deletions from more than one nsP gene. For example, and not intended by way of limitation, a deletion may encompass at least the nucleotide sequences encoding VEE nsP1 amino acid residues 101-120, 450-470, 460-480, 470-490, or 480-500, numbered relative to the sequence in Kinney et al., (1989) Virology 170:19-30, as well as smaller regions included within any of the above.

Figure 13:
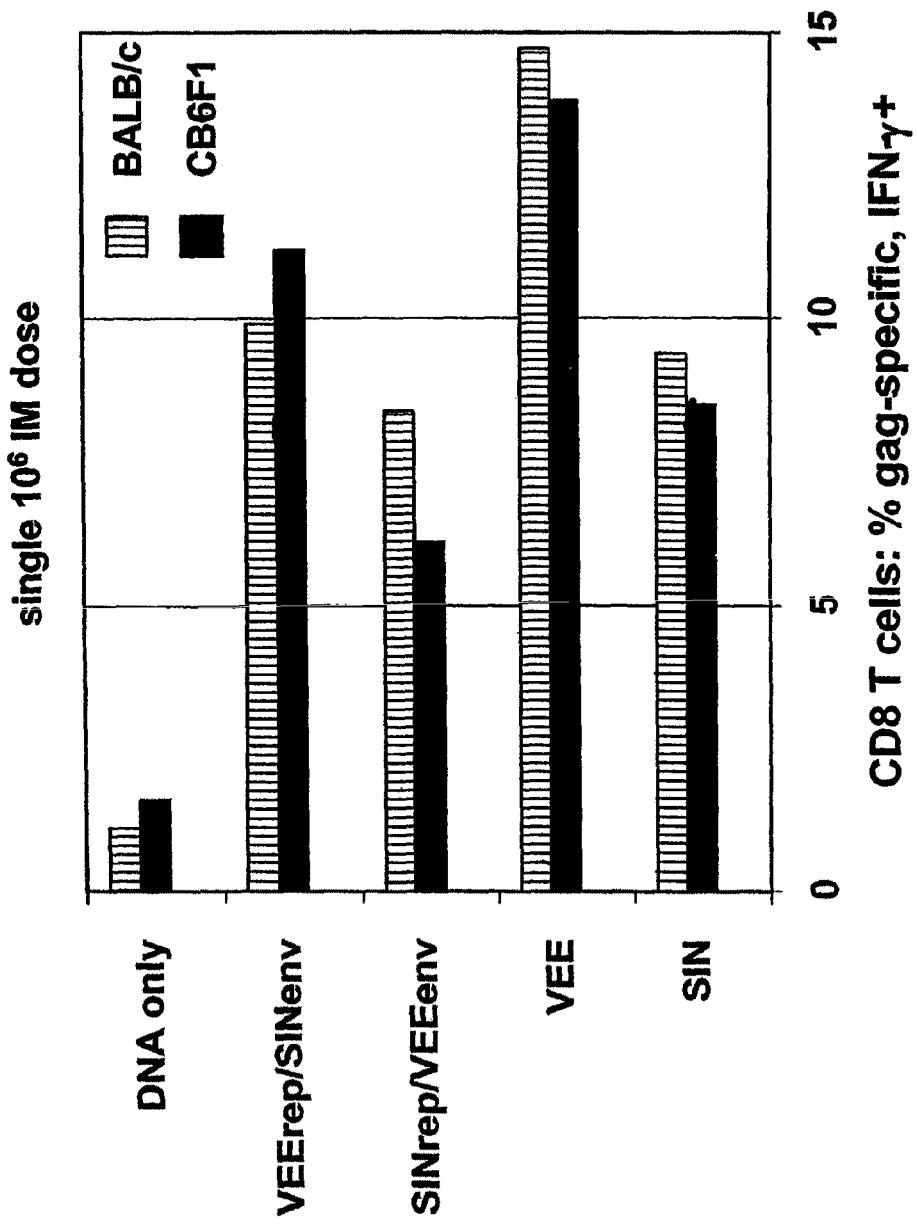
FIG. 13 is a graph depicting immunogenicity of alphavirus replicon particle chimeras expressing an HIV antigen. In particular, the graph depicts HIV p55gag-specific CD8+ T cell responses in mice primed with alphavirus replicon encoding HIV gag sequences and boosted with alphavirus replicon particles.

In another embodiment, a deletion may encompass at least the sequences encoding VEE nsP2 amino acid residues 9-29, 613-633, 650-670, or 740-760, as well as smaller regions included within any of the above. In another embodiment, a deletion may encompass at least the sequences encoding VEE nsP3 amino acid residues 340-370, 350-380, 360-390, 370-400, 380-410, 390-420, 400-430, 410-440, 420-450, 430-460, 440-470, 450-480, 460-490, 470-500, 480-510, 490-520, 500-530, or 488-522, as well as smaller regions included within any of the above. In another embodiment, the deletion may encompass at least the sequences encoding VEE nsP4 amino acid residues 8-28, or 552-570, as well as smaller regions included within any of the above. It should be noted that although the above amino acid ranges are illustrated using VEE as an example, similar types of deletions may be utilized in other alphaviruses. For example, in other embodiments, the modified non-structural proteins include a modification (e.g., deletion(s), addition(s) and/or substitution(s)) at a highly conserved location within an nsP4 of an alphavirus replicon. By way of non-limiting example and as shown in FIG. 13, the polymerase regions comprising nsP4 amino acids 368-400 of Sindbis virus (SIN), 375-407 of Semliki Forest virus (SFV), and 383-415 of Venezuelan equine encephalitis virus (VEE), as well as amino acids 462-494 of the 2a protein of the plant brome mosaic virus (BMV), have a high degree of sequence conservation and may serve as the target region for modification according to the present invention. (See, FIG. 14). Further, modifications to the adjacent amino acid sequence 1, 2 or 3 amino acids upstream or downstream from this region also are contemplated for alphavirus replicons.

Generally, while amino acid numbering is somewhat different between alphaviruses, primarily due to slight differences in polyprotein lengths, alignments amongst or between sequences from different alphaviruses provides a means to identify similar regions in other alphaviruses (see representative alignment in Kinney et al. (1989) Virology 170:19-30). Preferably, the nonstructural protein gene deletions of the present invention are confined to a region or stretch of amino acids considered as non-conserved among multiple alphaviruses. In addition, conserved regions also may be subject to deletion.

2.2. Alphavirus Structural Proteins

The structural proteins surrounding (and in some cases, interacting with) the alphavirus replicon or vector polynucleotide component(s) can include both capsid and envelope proteins. In most instances, the polynucleotide component(s) are surrounded by the capsid protein(s), which form nucleocapsids. In turn, the nucleocapsid protein is surrounded by a lipid envelope containing the envelope protein(s). It should be understood although it is preferred to have both capsid and envelope proteins, both are not required.

Alphavirus capsid proteins and envelope proteins are described generally in Strauss et al. (1994) Microbiol. Rev. 58:491-562. The capsid protein is the N-terminal protein of the alphavirus structural polyprotein, and following processing from the polyprotein, interacts with alphavirus RNA and other capsid protein monomers to form nucleocapsid structures.

Alphavirus envelope glycoproteins (e.g., E2, E1) protrude from the enveloped particle as surface "spikes", which are functionally involved in receptor binding and entry into the target cell.

One or both of these structural proteins (or regions thereof) may include one or more modifications as compared to wild-type. "Hybrid" structural proteins (e.g. proteins containing sequences derived from two or more alphaviruses) also find use in the practice of the present invention. Hybrid proteins can include one or more regions derived from different alphaviruses. These regions can be contiguous or non-contiguous. Preferably, a particular region of the structural protein (e.g., a functional regions such as the cytoplasmic tail portion of the envelope protein or the RNA binding domain of the capsid protein) is derived from a first alphavirus. Any amount of the "remaining" sequences of the protein (e.g., any sequences outside the designated region) can be derived from one or more alphaviruses that are different than the first. It is preferred that between about 25% to 100% (or any percentage value therebetween) of the "remaining" portion be derived from a different alphavirus, more preferably between about 35% and 100% (or any percentage value therebetween), even more preferably between about 50% and 100% (or any percentage value therebetween). The sequences derived from the one or more different alphaviruses in the hybrid can be contiguous or non-contiguous, in other words, sequences derived from one alphavirus can be separated by sequences derived from one or more different alphaviruses.

2.3. Modified Biosafety Level-3 Alphavirus Replicon

The compositions and methods described herein also allow for the modification of replicon vectors or Eukaryotic Layered Vector Initiation Systems derived from a BSL-3 alphavirus (e.g., VEE), such that they may be utilized at a lower classification level (e.g., BSL-2 or BSL-1) by reducing the nucleotide sequence derived from the parental BSL-3 alphavirus to more than one-third but less than two-thirds genome-length.

Thus, chimeric replicon vectors, particles or ELVIS can be used that include an alphavirus replicon RNA (or cDNA) sequence comprising a 5' sequence required for nonstructural protein-mediated amplification, sequences encoding biologically active alphavirus nonstructural proteins, an alphavirus subgenomic promoter, a non-alphavirus heterologous sequence, a 3' sequence required for nonstructural protein-mediated amplification, and optionally a polyadenylate tract, wherein the sequence encoding at least one of said nonstructural proteins is derived from a BSL-3 virus, but wherein the replicon RNA contains sequences derived from said Biosafety Level 3 alphavirus that in total comprise less than two-thirds genome-length of the parental Biosafety Level 3 alphavirus from which the sequence(s) is(are) derived.

Thus, the replicon sequences as described herein exhibit no more than 66.67% sequence identity to a BSL-3 alphavirus across the entire sequence. In other words, there may be many individual regions of sequence identity as compared to a BSL-3 genome, but the overall homology or percent identity to the entire genome-length of a BSL-3 is no more than 66.67% and nor less than 33.33%. Preferably, the replicon sequences derived from said Biosafety Level 3 alphavirus comprise between 40% and two-thirds genome-length of the parental Biosafety Level 3 alphavirus. More preferably, the replicon sequences derived from said Biosafety Level 3 alphavirus comprise between 50% and two-thirds genome-length of the parental Biosafety Level 3 alphavirus. Even more preferably, the replicon sequences derived from said Biosafety Level 3 alphavirus comprise between 55% and two-thirds genome-length of the parental Biosafety Level 3 alphavirus. Most preferably, the replicon sequences derived from said Biosafety Level 3 alphavirus comprise between 60% and two-thirds genome-length of the parental Biosafety Level 3 alphavirus.

As used herein, the definitions of Biosafety Level (e.g., Biosafety Level 2, 3, 4) are considered to be those of HHS Publication "Biosafety in Microbiological and Biomedical Laboratories", from the U.S. Department of Health and Human Services (Public Health Service, Centers for Disease Control and Prevention, National Institutes of Health), excerpts of which pertain to such classifications are incorporated below.

Biosafety Level 1 practices, safety equipment, and facility design and construction are appropriate for undergraduate and secondary educational training and teaching laboratories, and for other laboratories in which work is done with defined and characterized strains of viable microorganisms not known to consistently cause disease in healthy adult humans. *Bacillus subtilis, Naegleia grubri*, infectious canine hepatitis virus, and exempt organisms under the NIH Recombinant DNA Guidelines are representative of microorganisms meeting these criteria. Many agents not ordinarily associated with disease processes in humans are, however, opportunistic pathogens and may cause infection in the young, the aged, and immunodeficient or immunosuppressed individuals. Vaccine strains that have undergone multiple in vivo passages should not be considered a virulent simply because they are vaccine strains. Biosafety Level 1 represents a basic level of containment that relies on standard microbiological practices with no special primary or secondary barriers recommended, other than a sink for handwashing.

Biosafety Level 2 practices, equipment, and facility design and construction are applicable to clinical, diagnostic, teaching, and other laboratories in which work is done with the broad spectrum of indigenous moderate-risk agents that are present in the community and associated with human disease of varying severity. With good microbiological techniques, these agents can be used safely in activities conducted on the open bench, provided the potential for producing splashes or aerosols is low. Hepatitis B virus, HIV, the salmonellae, and *Toxoplasma* spp. are representative of microorganisms assigned to this containment level. Biosafety Level 2 is appropriate when work is done with any human-derived blood, body fluids, tissues, or primary human cell lines where the presence of an infectious agent may be unknown. (Laboratory personnel working with human-derived materials should refer to the OSHA *Bloodborne Pathogen Standard* 2, for specific required precautions). Primary hazards to personnel working with these agents relate to accidental percutaneous or mucous membrane exposures, or ingestion of infectious materials. Extreme caution should be taken with contaminated needles or sharp instruments. Even though organisms routinely manipulated at Biosafety Level 2 are not known to be transmissible by the aerosol route, procedures with aerosol or high splash potential that may increase the risk of such personnel exposure must be conducted in primary containment equipment, or in devices such as a BSC or safety centrifuge cups. Other primary barriers should be used as appropriate, such as splash shields, face protection, gowns, and gloves. Secondary barriers such as handwashing sinks and waste decontamination facilities must be available to reduce potential environmental contamination.

Biosafety Level 3 practices, safety equipment, and facility design and construction are applicable to clinical, diagnostic, teaching, research, or production facilities in which work is done with indigenous or exotic agents with a potential for respiratory transmission, and which may cause serious and potentially lethal infection. *Mycobacterium tuberculosis*, St. Louis encephalitis virus, and *Coxiella burnetii* are representative of the microorganisms assigned to this level. Primary hazards to personnel working with these agents relate to autoinoculation, ingestion, and exposure to infectious aerosols. At Biosafety Level 3, more emphasis is placed on primary and secondary barriers to protect personnel in contiguous areas, the community, and the environment from exposure to potentially infectious aerosols. For example, all laboratory manipulations should be performed in a BSC or other enclosed equipment, such as a gas-tight aerosol generation chamber. Secondary barriers for this level include controlled access to the laboratory and ventilation requirements that minimize the release of infectious aerosols from the laboratory.

Non-limiting examples of BSL-3 alphaviruses that may be used in the practice of the present invention include Cabassou virus, Kyzylagach virus, Tonate virus, Babanki virus, Venezuelan equine encephalitis virus (excluding TC-83 vaccine strain), Getah virus, Chikungunya virus, Middelburg virus, Sagiyama virus, Everglades virus, Mayaro virus, and Mucambo virus.

Biosafety Level 4 practices, safety equipment, and facility design and construction are applicable for work with dangerous and exotic agents that pose a high individual risk of life-threatening disease, which may be transmitted via the aerosol route and for which there is no available vaccine or therapy. Agents with a close or identical antigenic relationship to Biosafety Level 4 agents also should be handled at this level. When sufficient data are obtained, work with these agents may continue at this level or at a lower level. Viruses such as Marburg or Congo-Crimean hemorrhagic fever are manipulated at Biosafety Level 4. The primary hazards to personnel working with Biosafety Level 4 agents are respiratory exposure to infectious aerosols, mucous membrane or broken skin exposure to infectious droplets, and autoinoculation. All manipulations of potentially infectious diagnostic materials, isolates, and naturally or experimentally infected animals, pose a high risk of exposure and infection to laboratory personnel, the community, and the environment. The laboratory worker's complete isolation from aerosolized infectious materials is accomplished primarily by working in a Class III BSC or in a full-body, air-supplied positive-pressure personnel suit. The Biosafety Level 4 facility itself is generally a separate building or completely isolated zone with complex, specialized ventilation requirements and waste management systems to prevent release of viable agents to the environment.

As utilized within the scope of the present invention, creating a replicon that contains more than one-third but less than two-thirds the original genome-length of sequence from any BSL-3 virus (referred to as the parental virus) may be accomplished in a variety of ways. For example, contiguous or non-contiguous regions of the parental virus can be deleted. Alternatively, contiguous or non-contiguous regions of the parental virus may be utilized. Alternatively, regions of the parental virus can be excised and ligated into a BSL-2 or BSL-1 backbone.

In certain embodiments, the alphavirus 5' and/or 3' ends (sequences required for nonstructural protein-mediated amplification) are reduced to the minimal nucleotide sequence required to maintain sufficient function in the context of a replicon for expression of heterologous sequences, or alternatively replaced by a non-alphavirus sequence capable of performing the same function. In other embodiments, one or more alphavirus nonstructural protein genes may be deleted within specific regions, for example regions that are not well conserved among alphaviruses (e.g., nsP3 non-conserved region) or elsewhere. Alternatively, the alphavirus subgenomic promoter region or subgenomic 5' NTR region may contain deletions. In still further embodiments, one or more structural protein genes may be deleted, as well as combinations of any of the above.

3.0. Methods of Producing Chimeric Replicon Particles

The chimeric alphavirus replicon particles according to the present invention may be produced using a variety of published methods. Such methods include, for example, transient packaging approaches, such as the co-transfection of in vitro transcribed replicon and defective helper RNA(s) (Liljestrom (1991) *Bio/Technology* 9:1356-1361; Bredenbeek et al. (1993) *J. Virol.* 67:6439-6446; Frolov et al. (1997) *J. Virol.* 71:2819-2829; Pushko et al. (1997) *Virology* 239:389-401; U.S. Pat. Nos. 5,789,245 and 5,842,723) or plasmid DNA-based replicon and defective helper constructs (Dubensky et al. (1996) *J. Virol.* 70:508-519), as well as introduction of alphavirus replicons into stable packaging cell lines (PCL) (Polo et al. (1999) *Proc. Natl. Acad. Sci. USA* 96:4598-4603; U.S. Pat. Nos. 5,789,245; 5,842,723; 6,015,694; WO 97/38087, WO 99/18226, WO 00/61772, and WO 00/39318).

In preferred embodiments, stable alphavirus packaging cell lines are utilized for replicon particle production. The PCL may be transfected with in vitro transcribed replicon RNA, transfected with plasmid DNA-based replicon (e.g., ELVIS vector), or infected with a seed stock of replicon particles, and then incubated under conditions and for a time sufficient to produce high titer packaged replicon particles in the culture supernatant. In particularly preferred embodiments, PCL are utilized in a two-step process, wherein as a first step, a seed stock of replicon particles is produced by transfecting the PCL with a plasmid DNA-based replicon. A much larger stock of replicon particles is then produced in the second step, by infecting a fresh culture of the PCL with the seed stock. This infection may be performed using various multiplicities of infection (MOI), including a MOI=0.01, 0.05, 0.1, 0.5, 1.0, 3, 5, or 10. Preferably infection is performed at a low MOI (e.g., less than 1). Replicon particles at titers even >$10^8$ infectious units (IU)/ml can be harvested over time from PCL infected with the seed stock. In addition, the replicon particles can subsequently be passaged in yet larger cultures of naïve PCL by repeated low multiplicity infection, resulting in commercial scale preparations with the same high titer. Importantly, by using PCL of the "split" structural gene configuration, these replicon particle stocks may be produced free from detectable contaminating RCV.

As described above, large-scale production of alphavirus replicon particles may be performed using a bioreactor. Preferably, the bioreactor is an external component bioreactor, which is an integrated modular bioreactor system for the mass culture, growth, and process control of substrate attached cells. The attachment and propagation of cells (e.g., alphavirus packaging cells) occurs in a vessel or chamber with tissue culture treated surfaces, and the cells are with fresh media for increased cell productivity. Monitoring and adjustments are performed for such parameters as gases, temperature, pH, glucose, etc., and crude vector is harvested using a perfusion pump. Typically, the individual components of an External Bioreactor separate external modules that are connected (i.e., via tubing). The external components can be pumps, reservoirs, oxygenators, culture modules, and other non-standard parts. A representative example of an External Component Bioreactor is the CellCube™ system (Corning, Inc).

In addition to using the external component bioreactor described herein, a more traditional Stir Tank Bioreactor may also be used, in certain instances, for alphavirus replicon particle production. In a Stir Tank Bioreactor, the alphavirus packaging cells may be unattached to any matrix (i.e., floating in suspension) or attached to a matrix (e.g., poly disks, micro- or macro carriers, beads). Alternatively, a Hollow Fiber Culture System may be used.

Following harvest, crude culture supernatants containing the chimeric alphavirus replicon particles may be clarified by passing the harvest through a filter (e.g., 0.2 µM, 0.45 µM, 0.65 µM, 0.8 µM pore size). Optionally, the crude supernatants may be subjected to low speed centrifugation prior to filtration to remove large cell debris. Within one embodiment, an endonuclease (e.g., Benzonase, Sigma #E8263) is added to the preparation of alphavirus replicon particles before or after a chromatographic purification step to digest exogenous nucleic acid. Further, the preparation may be concentrated prior to purification using one of any widely known methods (e.g., tangential flow filtration).

Crude or clarified alphavirus replicon particles may be concentrated and purified by chromatographic techniques (e.g., ion exchange chromatography, size exclusion chromatography, hydrophobic interaction chromatography, affinity chromatography). Two or more such purification methods may be performed sequentially. In preferred embodiments, at least one step of ion exchange chromatography is performed and utilizes a ion exchange resin, such as a tentacle ion exchange resin, and at least one step of size exclusion chromatography is performed. Briefly, clarified alphavirus replicon particle filtrates may be loaded onto a column containing a charged ion exchange matrix or resin (e.g., cation or anion exchange). The matrix or resin may consist of a variety of substances, including but not limited to cross-linked agarose, cross linked polystyrene, cross linked styrene, hydrophilic polyether resin, acrylic resin, and methacrylate based resin. The ion exchanger component may comprise, but is not limited to, a cationic exchanger selected from the list consisting of sulphopropyl cation exchanger, a carboxymethyl cation exchanger, a sulfonic acid exchanger, a methyl sulfonate cation exchanger, and an SO3-exchanger. In other embodiments, the ion exchanger component may comprise, but is not limited to, an anionic exchanger selected from the list consisting of DEAE, TMAE, and DMAE. Most preferably, ion exchange chromatography is performed using a tentacle cationic exchanger, wherein the ion exchange resin is a methacrylate-based resin with an SO3-cation exchanger (e.g., Fractogel® EDM SO3-).

The chimeric replicon particles may be bound to the ion exchange resin followed by one or more washes with buffer containing a salt (e.g., 250 mM or less NaCl). Replicon particles then may be eluted from the column in purified for using a buffer with increased salt concentration. In preferred embodiments, the salt concentration is a least 300 mM, 350 mM, 400 mM, 450 mM or 500 mM. Elution may be monitored preferably by a spectrophotometer at 280 nm, but also by replicon titer assay, transfer of expression (TOE) assay, or protein gel analysis with subsequent Coomassie staining or Western blotting.

The higher salt elution buffer subsequently may be exchanged for a more desirable buffer, for example, by dilution in the appropriate aqueous solution or by passing the particle-containing eluate over a molecular exclusion column. Additionally, the use of a molecular size exclusion column may also provide, in certain instances, further purification. For example, in one-embodiment Sephacryl S-500 or S400 (Pharmacia) chromatography may be used as both a buffer exchange as well as to further purify the fractions containing the replicon particles eluted from an ion exchange column. Using this particular resin, the replicon particles generally are eluted in the late void volume and show improvement in the level of purity as some of the contaminants are smaller in molecular weight and are retained on the column longer. However, alternative resins of different compositions as well as size exclusion could also be used that might yield similar or improved results. In these strategies, larger-sized resins such as Sephacryl S-1000 could be incorporated that would allow the replicon particles to enter into the matrix and thus be retained longer, allowing fractionation.

The methods described herein are unlike widely practiced methods in which the defective helper RNAs and the replicon vector contain genes derived from the same virus, thereby allowing the process of replicon particle assembly to proceed naturally and resulting in a replicon particle having a replicon packaged within a viral capsid and envelope protein(s) derived from the same virus that contributed the nonstructural protein genes. Consequently, in such methods, the packaging signal (also known as packaging sequences), the RNA binding domain, the glycoprotein interaction domain and envelope glycoproteins are all from the same virus.

In contrast, the methods described herein involve the successful and efficient production of alphavirus replicon particles from sequences derived from two or more alphaviruses. As described herein, the particles are produced more efficiently and, additionally, have other advantages as well.

Methods are also provided to package alphavirus replicon RNA into replicon particles (produce replicon particles) and reduce the probability of generating replication-competent virus (e.g., wild-type virus) during packaging, comprising introducing into a permissible cell an alphavirus replicon RNA encoding biologically active alphavirus nonstructural proteins and a heterologous polypeptide, together with one or more defective helper RNA(s) encoding at least one alphavirus structural protein, and incubating said cell under suitable conditions for a time sufficient to permit production of replicon particles. In these embodiments, both the replicon RNA and defective helper RNA include control elements, particularly a 5' sequence required for nonstructural protein-mediated amplification, a means to express the polypeptide-encoding sequences (the polypeptide-encoding sequence(s) are also referred to as the 3' proximal gene), for example a promoter that drives expression of (1) the heterologous protein in the replicon and (2) the structural proteins in the defective helper RNA, a 3' sequence required for nonstructural protein-mediated amplification, a polyadenylate tract, and, optionally, a subgenomic 5'-NTR. Further, unlike known methods, one or more of these control elements are different (e.g., the sequence is different) as between the RNA in the replicon and the RNA in the defective helper. For example, in certain embodiments, the 5' sequence required for nonstructural protein-mediated amplification is different as between the replicon and the helper RNA. In other embodiments, the means to express the polypeptide-encoding sequences and/or the 3' sequence required for nonstructural protein-mediated amplification is different as between the replicon and the helper RNA.

One of skill in the art will readily understand that introduction of replicon RNA into permissive cells may be performed by a variety of means, such as for example, transfection or electroporation of RNA (e.g., in vitro transcribed RNA), transcription of RNA within the cell from DNA (e.g., eukaryotic layered vector initiation system), or delivery by viral or virus-like particles (e.g., replicon particles) and introduction of defective helper RNA into permissive cells may also be performed by a variety of means, such as for example, transfection or electroporation of RNA (e.g., in vitro transcribed RNA) or transcription of RNA within the cell from DNA (e.g., structural protein expression cassette).

In addition, modifications to reduce homologous sequences may also be made at the DNA backbone level, such as for example, in a Eukaryotic Layered Vector Initiation System or structural protein expression cassette used for the derivation of packaging cells. Such modifications include, but are not limited to, alternative eukaryotic promoters, polyadenylation sequences, antibiotic resistance markers, bacterial origins of replication and other non-functional backbone sequences.

4.0 Pharmaceutical Compositions

The present invention also provides pharmaceutical compositions comprising any of the alphavirus replicon particles, vectors and/or replicons described herein in combination with a pharmaceutically acceptable carrier, diluent, or recipient. Within certain preferred embodiments, a sufficient amount of formulation buffer is added to the purified replicon particles to form an aqueous suspension. In preferred embodiments, the formulation buffer comprises a saccharide and a buffering component in water, and may also contain one or more amino acids or a high molecular weight structural additive. The formulation buffer is added in sufficient amount to reach a desired final concentration of the constituents and to minimally dilute the replicon particles. The aqueous suspension may then be stored, preferably at −70° C., or immediately dried.

The aqueous suspension can be dried by lyophilization or evaporation at ambient temperature. Briefly, lyophilization involves the steps of cooling the aqueous suspension below the gas transition temperature or below the eutectic point temperature of the aqueous suspension, and removing water from the cooled suspension by sublimation to form a lyophilized replicon particle. Within one embodiment, aliquots of the formulated recombinant virus are placed into an Edwards Refrigerated Chamber (3 shelf RC3S unit) attached to a freeze dryer (Supermodulyo 12K). A multistep freeze drying procedure as described by Phillips et al. (*Cryobiology* 18:414 (1981)) is used to lyophilize the formulated replicon particles, preferably from a temperature of −40° C. to −45° C. The resulting composition contains less than 10% water by weight of the lyophilized replicon particles. Once lyophilized, the replicon particles are stable and may be stored at −20° C. to 25° C., as discussed in more detail below. In the evaporative method, water is removed from the aqueous suspension at ambient temperature by evaporation. Within one embodiment, water is removed by a spray-drying process, wherein the aqueous suspension is delivered into a flow of preheated gas, usually which results in the water rapidly evaporating from droplets of the suspension. Once dehydrated, the recombinant virus is stable and may be stored at −20° C. to 25° C.

The aqueous solutions used for formulation preferably comprise a saccharide, a buffering component, and water. The solution may also include one or more amino acids and a high molecular weight structural additive. This combination of components acts to preserve the activity of the replicon particles upon freezing and also lyophilization or drying through evaporation. Although a preferred saccharide is lactose, other saccharides may be used, such as sucrose, mannitol, glucose, trehalose, inositol, fructose, maltose or galactose. A particularly preferred concentration of lactose is 3%-4% by weight.

The high molecular weight structural additive aids in preventing particle aggregation during freezing and provides structural support in the lyophilized or dried state. Within the context of the present invention, structural additives are considered to be of "high molecular weight" if they are greater than 5000 M.W. A preferred high molecular weight structural additive is human serum albumin. However, other substances may also be used, such as hydroxyethyl-cellulose, hydroxymethyl-cellulose, dextran, cellulose, gelatin, or povidone. A particularly preferred concentration of human serum albumin is 0.1% by weight.

The buffering component acts to buffer the solution by maintaining a relatively constant pH. A variety of buffers may be used, depending on the pH range desired, preferably between 7.0 and 7.8. Suitable buffers include phosphate buffer and citrate buffer. In addition, it is preferable that the aqueous solution contains a neutral salt that is used to adjust the final formulated replicon particles to an appropriate iso-osmotic salt concentration. Suitable neutral salts include sodium chloride, potassium chloride or magnesium chloride. A preferred salt is sodium chloride. The lyophilized or dehydrated replicon particles of the present invention may be reconstituted using a variety of substances, but are preferably reconstituted using water. In certain instances, dilute salt solutions that bring the final formulation to isotonicity may also be used.

5.0 Applications

The chimeric alphavirus particles can be used to deliver a wide variety of nucleotide sequences including, for example, sequences which encode lymphokines or cytokines (e.g., IL-2, IL-12, GM-CSF), prodrug converting enzymes (e.g. HSV-TK, VZV-TK), antigens which stimulate an immune response (e.g., HIV, HCV, tumor antigens), therapeutic molecules such as growth or regulatory factors (e.g., VEGF, FGF, PDGF, BMP), proteins which assist or inhibit an immune response, as well as ribozymes and antisense sequences. The above nucleotide sequences include those referenced previously (e.g., U.S. Pat. No. 6,015,686, WO 9738087 and WO 9918226), and may be obtained from repositories, readily cloned from cellular or other RNA using published sequences, or synthesized, for example, on an Applied Biosystems Inc. DNA synthesizer (e.g., APB DNA synthesizer model 392 (Foster City, Calif.)).

For purposes of the present invention, virtually any polypeptide or polynucleotide can be used. Antigens can be derived from any of several known viruses, bacteria, parasites and fungi, as well as any of the various tumor antigens or any other antigen to which an immune response is desired. Furthermore, for purposes of the present invention, an "antigen" refers to a protein that includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts that produce the antigens.

Antigens may be used alone or in any combination. (See, e.g. WO 02/00249 describing the use of combinations of bacterial antigens). The combinations may include multiple antigens from the same pathogen, multiple antigens from different pathogens or multiple antigens from the same and from different pathogens. Thus, bacterial, viral, tumor and/or other antigens may be included in the same composition or may be administered to the same subject separately. It is generally preferred that combinations of antigens be used to raise an immune response be used in combinations.

Non-limiting examples of bacterial pathogens include diphtheria (See, e.g., Chapter 3 of *Vaccines*, 1998, eds. Plotkin & Mortimer (ISBN 0-7216-1946-0), staphylococcus (e.g., *Staphylococcus aureus* as described in Kuroda et al. (2001) *Lancet* 357:1225-1240), cholera, tuberculosis, *C. tetani*, also known as tetanus (See, e.g. Chapter 4 of *Vaccines*, 1998, eds. Plotkin & Mortimer (ISBN 0-7216-1946-0), Group A and Group B *streptococcus* (including *Streptococcus pneumoniae, Streptococcus agalactiae* and *Streptococcus pyogenes* as described, for example, in Watson et al. (2000) *Pediatr. Infect. Dis. J.* 19:331-332; Rubin et al. (2000) *Pediatr. Clin. North Am.* 47:269-284; Jedrzejas et al. (2001) *Microbiol. Mol. Biol. Rev.* 65:187-207; Schuchat (1999) *Lancet* 353:51-56; GB patent applications 0026333.5; 0028727.6; 015640.7; Dale et al. (1999) *Infect. Dis. Clin. North Am.* 13:227-1243; Ferretti et al. (2001) *Proc. Natl. Acad. Sci. USA* 98:4658-4663), pertussis (see, e.g., Gusttafsson et al. (1996) *N. Engl. J. Med.* 334:349-355; Rappuoli et al. (1991) *TIBTECH* 9:232-238), meningitis, *Moraxella catarrhalis* (See, e.g., McMichael (2000) *Vaccine* 19 Suppl. 1:S 101-107) and other pathogenic states, including, without limitation, *Neisseria meningitides* (A, B, C, Y), *Neisseria gonorrhoeae* (See, e.g., WO 99/24578; WO 99/36544; and WO 99/57280), *Helicobacter pylori* (e.g., CagA, VacA, NAP, HopX, HopY and/or urease as described, for example, WO 93/18150; WO 99/53310; WO 98/04702) and *Haemophilus influenza. Hemophilus* influenza type B (HIB) (See, e.g., Costantino et al. (1999) *Vaccine* 17:1251-1263), *Porphyromonas gingivalis* Ross et al. (2001) *Vaccine* 19:4135-4132) and combinations thereof.

Non-limiting examples of viral pathogens include-meningitis, rhinovirus, influenza (Kawaoka et al. (1990) *Virology* 179:759-767; Webster et al., "Antigenic variation among type A influenza viruses," pp. 127-168, In P. Palese and D. W. Kingsbury (ed.), *Genetics of influenza viruses* (Springer-Verlag, NY), respiratory syncytial virus (RSV), parainfluenza virus (PIV), and the like. Antigens derived from other viruses will also find use in the present invention, such as without limitation, proteins from members of the families Picomaviridae (e.g., polioviruses, etc. as described, for example, in Sutter et al. (2000) *Pediatr. Clin. North Am.* 47:287-308; Zimmerman & Spann (1999) *Am. Fam. Physician* 59:113-118; 125-126); Caliciviridae; Togaviridae (e.g., rubella virus, dengue virus, etc.); the family Flaviviridae, including the genera *flavivirus* (e.g., yellow fever virus, Japanese encephalitis virus, serotypes of Dengue virus, tick borne encephalitis virus, West Nile virus); pestivirus (e.g., classical porcine fever virus, bovine viral diarrhea virus, border disease virus); and hepacivirus (e.g. hepatitis A, B and C as described, for example, in U.S. Pat. Nos. 4,702,909; 5,011,915; 5,698,390; 6,027,729; and 6,297,048); Parvovirsus (e.g., parvovirus B19); Coronaviridae; Reoviridae; Bimaviridae; Rhabodoviridae (e.g., rabies virus, etc. as described for example in Dressen et al. (1997) *Vaccine* 15 Suppl:s2-6; *MMWR Morb Mortal Wkly Rep.* Jan. 16, 1998:47(1):12, 19); Filoviridae; Paramyxoviridae (e.g., mumps virus, measles virus, rubella, respiratory syncytial virus, etc. as described in Chapters 9 to 11 of *Vaccines,* 1998, eds. Plotkin & Mortimer (ISBN 0-7216-1946-0); Orthomyxoviridae (e.g., influenza virus types A, B and C, etc. as described in Chapter 19 of *Vaccines,* 1998, eds. Plotkin & Mortimer (ISBN 0-7216-1946-0)); Bunyaviridae; Arenaviridae; Retroviradae (e.g., HTLV-1; HTLV-11; HIV-1 (also known as HTLV-III, LAV, ARV, HTI,R, etc.)), including but not limited to antigens from the isolates HIVIIIb, HIVSF2, HIVLAV, HIVI-AL, I-IIVMN); HIV-I CM235, HIV-I IJS4; HIV-2; simian immunodeficiency virus (SIV) among others. Additionally, antigens may also be derived from human papilloma virus (HPV) and the tick-borne encephalitis viruses. See, e.g. *Virology,* 3rd Edition (W. K. Joklik ed. 1988); *Fundamental Virology,* 2nd Edition (B. N. Fields and D. M. Knipe, eds, 1991), for a description of these and other viruses.

Antigens from the hepatitis family of viruses, including hepatitis A virus (HAV) (See, e.g., Bell et al. (2000) *Pediatr. Infect. Dis. J.* 19:1187-1188; Iwarson (1995) *APMIS* 103: 321-326), hepatitis B virus (HBV) (see, e.g., Gerlich et al. (1990) *Vaccine* 8 Suppl:S63-68 & 79-80), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., WO 89/04669; WO 90/11089; and WO 90/14436. Also included in the invention are molecular variants of such polypeptides, for example as described in WO 00/39302; WO 00/39304 and WO 00/39303.

Non-limiting examples of tumor antigens include antigens recognized by CD8+ lymphocytes (e.g., melanoma-melanocyte differentiation antigens such as MART-1, gp100, tyrosinase, tyrosinase related protein-1, tyrosinase related protein-2, melanocyte-stimulating hormone receptor; mutated antigens such as beta-catenin, MUM-1, CDK-4, caspase-8, KIA 0205, HLA-A2-R1701; cancer-testes antigens such as MAGE-1, MAGE-2, MAGE-3, MAGE-12, BAGE, GAGE and NY-ESO-1; and non-mutated shared antigens over expressed on cancer such as alpha-fetoprotein, telomerase catalytic protein, G-250, MUC-1, carcinoembryonic antigen, p53, Her-2-neu) as well as antigens recognized by CD4+ lymphocytes (e.g., gp100, MAGE-1, MAGE-3, tyrosinase, NY-ESO-1, triosephosphate isomerase, CDC-27, and LDLR-FUT). See, also, WO 91/02062, U.S. Pat. No. 6,015,567, WO 01/08636, WO 96/30514, U.S. Pat. No. 5,846,538 and U.S. Pat. No. 5,869,445.

In certain embodiments, the tumor antigen(s) may be used. Tumor antigens are derived from mutated or altered cellular components. After alteration, the cellular components no longer perform their regulatory functions, and hence the cell may experience uncontrolled growth. Representative examples of altered cellular components include ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor. These as well as other cellular components are described for example in U.S. Pat. No. 5,693,522 and references cited therein.

The present invention also provides methods for delivering these selected heterologous sequences to a warm-blooded mammal (e.g., a mammal such as a human or other warm-blooded animal such as a horse, cow, pig, sheep, dog, cat, rat or mouse) for use as a vaccine or therapeutic, comprising the step of administering to the mammal replicon particles or eukaryotic layered vector initiation systems as described herein, which are capable of expressing the selected heterologous sequence. Delivery may be by a variety of routes (e.g., intravenously, intramuscularly, intradermally, intraperitoneally, subcutaneously, orally, intraocularly, intranasally, rectally, intratumorally). In addition, the replicon particles may either be administered directly (i.e., in vivo), or to cells that have been removed (ex vivo), and subsequently returned to the warm-blooded mammal.

It should be noted that the selected method for production of chimeric alphavirus replicon particles of the present invention should use techniques known in the art to minimize the possibility of generating contaminating replication-competent virus (RCV). One such strategy is the use of defective helpers or PCL that contain "split" structural protein expression cassettes (see U.S. Pat. Nos. 5,789,245; 6,242,259; 6,329,201). In this context, the alphavirus structural protein genes are segregated into separate expression constructs (e.g., capsid separate from glycoproteins) such that recombination to regenerate a complete complement of structural proteins is highly unlikely. The present invention also provides compositions and methods to further reduce the probability of recombination events during production of alphavirus replicon particles, beyond those conventional methods known in the art. For example, any of the several functional elements (e.g., control elements) commonly shared by replicon and defective helper RNA, or shared between multiple defective helper RNAs (also eukaryotic layered vector initiation systems and structural protein expression cassettes) may be substituted with alternative elements that perform the same function. In this instance, homology between RNA molecules is decreased or eliminated. Alternatively, the likelihood of polymerase template switching between RNA molecules also may be reduced. Representative functional elements commonly shared by replicon and defective helper RNA, or shared between multiple defective helper RNAs, as well as some alternatives for each as contemplated within the present invention are included, but not limited to those described above in Section B above.

The following examples are included to more fully illustrate the present invention. Additionally, these examples provide preferred embodiments of the invention and are not meant to limit the scope thereof.

EXAMPLES

Example 1

Construction of a VEE Derived Replicon Vector

In order to construct VEE derived replicon vectors and defective helper packaging cassettes for use in producing chimeric particles, it was necessary to first synthesize complementary DNA corresponding to the entire VEE genome. Based on previously published sequence from the wild-type Trinidad Donkey strain of VEE (GENBANK, L01442), (hereinafter VEE-TRD) the entire 11,447 genome was synthesized and cloned in multiple fragments using overlapping oligonucleotides. Nonstructural protein gene clones were used for assembly of a replicon vector, while the structural protein gene clones were used for assembly of defective helper packaging cassettes.

The sequences encoding VEE-TRD nonstructural protein genes were analyzed for suitable unique restriction cleavage sites that would subdivide the region into fragments of practical length and which could be conveniently used for final assembly of the complete replicon vector construct. As shown in FIG. 1, a total of 13 intermediate fragments were identified, ranging in length from 334 to 723 nucleotides. This series of fragments was synthesized using overlapping oligonucleotides and techniques commonly employed by those of skill in the art of molecular biology (see below, for example). To the terminal fragments #1 and #13 were appended additional sequences necessary to for final construction of the plasmid that could be used for transcription of RNA replicon expression vectors in vitro and in vivo. Upstream, as part of fragment 1, was placed either a bacteriophage SP6 promoter or eukaryotic CMV promoter to allow for transcription of replicon RNA. Downstream, as part of fragment 13, was replicated the viral 3' UTR, a synthetic A40 polyadenylation tract, and the hepatitis delta virus antigenomic ribozyme for generation of authentically terminated RNAs (Dubensky et al. (1996) *J. Virol.* 70:508-519; Polo, 1999, ibid).

As a detailed example of gene synthesis for one of the fragments, full duplex DNA strands for replicon fragment #2 were generated from overlapping synthetic oligonucleotides as described below and shown in FIG. 2 (adjacent oligonucleotides are shown with or without shading to highlight junctions). First, the full duplex strand was appended with the recognition sequence of convenient restriction enzyme sites suitable for insertion into intermediate cloning vectors. Each fragment was then subdivided into a series of oligonucleotides with an average length of 60 nucleotides each, and overlapping those oligonucleotides from the opposite strand by an average of 20 nucleotides at either end. Synthesis of the initial oligonucleotides was performed by commercial vendors (e.g., Integrated DNA Technologies, Coralville, Iowa; Operon Technologies, Alameda, Calif.). Oligonucleotides for each fragment were re-constituted as per the supplier's recommendation to yield 100 nM solutions of each individual oligo. To assemble the fragment, 100 pmoles of each oligo was mixed in a single reaction tube containing T4 polynucleotide kinase buffer (New England Biolabs, Beverly, Mass.), 1 mM rATP, water, and 10 units of T4 polynucleotide kinase enzyme (New England Biolabs, Beverly, Mass.) in a final reaction volume of 500 μl. The phosphorylation reaction was allowed to proceed for 30 minutes at 37° C., at which time the reaction was supplemented with an additional 10 units of T4 polynucleotide kinase and allowed to continue for an additional 30 minutes. At the conclusion of the reaction, the tube containing the mixture was heated to 95° C. for 5' in a beaker containing a large volume of water to denature the enzyme and any DNA strands that may have already annealed. The beaker was then removed from the heat source and allowed to slowly cool to ambient temperature, in order for the complementary oligonucleotides to anneal into full duplex DNA strands.

Once cooled, 0.2 pmoles of the reacted material was ligated with 100 pmoles of previously prepared shuttle vector DNA and transformed into competent bacteria according to standard methods. Transformants arising from this ligation were analyzed first for the presence of the appropriate terminal replicon enzyme sites, for insert size, and evidence of insert duplication. Several positive transformants were randomly chosen and submitted for sequence confirmation. Any detected sequence errors were corrected by fragment swap between two or more sequenced samples, or by site-directed mutagenesis, and re-confirmed for authenticity.

After all fragments were obtained, final assembly of a replicon vector, similar to those published previously with a variety of alphaviruses (Xiong et al. (1989) *Science* 243:1188-1191; Dubensky et al., 1996, ibid; Liljestrom et al; (1991) *Bio/Technol.* 9:1356-1361; Pushko et al. (1997) *Virology* 239:389401), was performed by piecing each sub-fragment together with its adjoining fragment through ligation at the previously selected terminal fragment cleavage sites. Once assembled, the sequence of the entire synthetic VEE replicon was re-confirmed. The resulting VEE-based alphavirus vector construct from which replicon RNA can be transcribed in vitro was designated pVCR.

In addition to the SP6 promoter-based vector replicon construct, a VEE-based eukaryotic layered vector initiation system (ELVIS, see U.S. Pat. Nos. 5,814,482 and 6,015,686), which utilized a CMV promoter for launching functional RNA replicons from within a eukaryotic cell, also was constructed. Modification of plasmid pVCR for conversion into an ELVIS vector was accomplished as follows. An existing Sindbis virus (SIN) based ELVIS vector, pSINCP, was used as a donor source for the appropriate backbone components including the CMV promoter, Kanamycin resistance gene, and origin of replication. This strategy was possible because both pSINCP and pVCR share identical sequence elements (e.g., synthetic polyA sequence, HDV ribozyme) downstream of the nonstructural gene and viral 3' UTR regions. In pVCR, the HDV ribozyme is flanked by a unique PmeI site, while in pSINCP the ribozyme is flanked by a BclI site. The PmeI/BclI fusion then served as the 5' joining site between pSINCP and pVCR. The 3' joining site was a fortuitous BspEI site present in nsP1 of both SIN and VEE. In order to accomplish the backbone swap, pSINCP was first transformed into a Dam/Dcm-minus host bacteria, SCS110 (Stratagene, La Jolla, Calif.) to obtain DNA cleavable by BclI. A 1203 base pair fragment containing the BGHt on the 5' end and Kan R gene on the 3' end was isolated and blunted by means of T4 DNA polymerase (New England Biolabs, Beverly, Mass.) following standard methods. This fragment was subsequently further digested with Pst I to liberate a 999 bp BclI-PstI fragment that was purified containing the BGHt and the 5' 2/3 of the Kan R gene.

Plasmid pSINCP contains 4 BspEI sites. To make fragment identification more precise, the plasmid was co-digested with NotI, SalI, and Eco47III and the 5173 bp fragment was isolated. This fragment was then further digested with PstI and BspEI and from this a 2730 bp PstI-BspEI fragment was purified which contained the 3' 1/3 of the Kan R gene, plasmid origin of replication, the CMV pol II promoter, and 420 bp of the Sindbis nsP1 gene.

As a source of the 5' and 3' end of the VCR replicon, an early intermediate, pVCR-DH (see below) was utilized. pVCR-DH contains fragment 1, fragment 13, and all of the terminal restriction sites of the intermediate fragments. As such it contains a portion of the VEE-TRD nsP1 gene including the necessary BspEI site and all of the 3' features described above that were necessary for the swap but lacks the core nonstructural region from the 3' end of nsPI through the 5' end of nsP4. pVCR-DH was transformed into SCS110 cells as before and digested with BspEI and PmeI to release a 1302 bp fragment containing nsP1'-nsP4', 3' UTR, A40 tract, and HDV ribozyme.

A three-way ligation of the BclI(blunt)PstI, and PstI-BspEI fragments from pSINCP, and the BspEI-PmeI fragment from pVCR-DH was performed. The resulting intermediate was designated pVCPdhintSP. Plasmid pVCPdhintSP was digested with SacI (cutting 15 bp before the 3' end of the CMV promoter) and BspEI at the junction of the Sindbis and VEE sequences in nsP1. The vector fragment of this digest was de-phosphorylated and ligated with a 326 bp PCR product from pVCR-DH providing the missing 5' terminus of VEE-TRD nsP1. The 5' primer, [AAGCAGAGCTCGTT-TAGTGAACCGTATGGGCGGCGCATG] (SEQ ID NO: 1) juxtaposed the 3' terminal 15 nucleotides of the CMV promoter (up to the transcription start site) to the starting base of the VEE 5' UTR sequence. The 3' primer had the sequence listed [gccctgcgtccagctcatctcgaTCT-GTCCGGATCTTCCGC.] (SEQ ID NO: 2). This intermediate was termed, pVCPdhintf. To complete the construct, pVCPdhintf was digested with NotI and HpaI and the vector fragment was de-phosphorylated and ligated to the HpaI-NotI fragment of pVCR providing the missing core VEE nonstructural sequences missing from the pVCPdhintf intermediate. This final VEE-based ELVIS construct was designated pVCP.

Example 2

Construction of Alphavirus Defective Helper Constructs

Prior to construction of defective helpers (DH) of the present invention for use in generating hybrid structural protein elements and chimeric alphavirus particles, previous existing SIN based defective helper packaging cassettes (Polo et al., 1999, ibid; Gardner et al., 2000 ibid) were first modified. To generate these new SIN cassettes, plasmid SINBV-neo (Perri et al. (2000) *J. Virol.* 74:9802-9807) was digested with ApaI, treated with T4 DNA polymerase to blunt the ApaI generated-ends, and then digested with BglII and BamHI. The 4.5 kb fragment, which contained the plasmid backbone, the SIN subgenomic promoter, SIN 3'-end, synthetic polyA tract, and the HDV antigenomic ribozyme, was gel purified with QIAquick gel extraction kit and ligated to a 714 bp fragment containing an SP6 promoter and SIN tRNA 5'-end, obtained from plasmid 47tRNA BBCrrvdel 13 (Frolov et al. (1997) *J. Virol.* 71:2819-2829) which had been previously digested with SacI, treated with T4 DNA polymerase, digested with BamHI and gel purified. Positive clones were verified by restriction analysis this construct was used as the basis for insertion via the XhoI-NotI sites (removes existing Neo insert), of the alphavirus glycoprotein and capsid sequences described below. The SIN defective helper cassette backbone described herein is referred to as tDH.

VCR-DH Construction

A polylinker region was cloned into the vector backbone of SINCR-GFP (Gardner et al., 2000, ibid) as a first step. The polylinker contained the following restriction sites from 5' to 3': ApaI-MluI-HpaI-BglII-Bsu36I-PstI-BsaBI-AvrII-SwaI-AspI-BbvCI-AscI-NotI-PmeI. To generate the polylinker, the following oligonucleotides were used:

```
PL1F 5'-cacgcgtactactgttaactcatcaagatctactaggcctaa
     ggcaccacctgcaggtagtagatacacatcataatacc-3'
     (SEQ ID NO: 3)

PL2F 5'-tagggcggcgatttaaatgatttagactacgtcagcagccct
     cagcggcgcgcccacccagcggccgcaggatagttt-3'
     (SEQ ID NO: 4)

PL1R 5'-tatgatgtgtatctactacctgcaggtggtgccttaggccta
     gtagatcttgatgagttaacagtagtacgcgtgggcc-3'
     (SEQ ID NO: 5)

PL2R 5'-aaactatcctgcggccgctgggtgggcgcgccgctgagggct
     gctgacgtagtctaaatcatttaaatcgccgccctaggtat-3'
     (SEQ ID NO: 6)
```

Oligonucleotides PL1F and PL1R, and oligonucleotides PL2F and PL2R were mixed in two separate reactions, phosphorylated, denatured, and slowly annealed. The two reactions were then mixed and ligated to the 2.8 kb fragment generated from plasmid SINCR-GFP that had been previously digested with ApaI and PmeI and gel purified using QIAquick gel extraction kit. Clones were screened for the correct orientation using AlwNI and NotI restriction digests. The positive clones were verified by restriction digest with each single enzyme present in the polylinker. This construct was named VCR-backbone. Next, the VEE 3'-end, together with a polyadenylation tract and the HDV ribozyme were inserted into VCR backbone. This fragment was generated using the following overlapping synthetic oligonucleotides.

```
VEE3'-1F
                                      (SEQ ID NO: 7)
5'-ggccgcatacagcagcaattggcaagctgcttacatagaactcgcgg
cgattggcatg-3'

VEE3'-1R
                                      (SEQ ID NO: 8)
5'-ccaatcgccgcgagttctatgtaagcagcttgccaattgctgctgta
tgc-3'

VEE3'-2F
                                      (SEQ ID NO: 9)
5'-ccgccttaaaattttttattttattttttcttttcttttccgaatcgg
attttgttttaat-3'

VEE3'-2R
                                     (SEQ ID NO: 10)
5'-attaaaaacaaaatccgattcggaaaagaaaagaaaaaataaaataa
aaattttaaggcggcatg-3'

VEE3'-3F
                                     (SEQ ID NO: 11)
5'-atttcaaaaaaaaaaaaaaaaaaaaaaaaaaaaaaaaaaaaaaaagg
gtcggcatggcatctccacctcctcgcg-3'

VEE3'-3R
                                     (SEQ ID NO: 12)
5'-gaccgcgaggaggtggagatgccatgccgaccctttttttttttttt
ttttttttttttttttttttttttttgaaat-3'

VEE3'-4F
                                     (SEQ ID NO: 13)
5'-gtccgacctgggcatccgaaggaggacgcacgtccactcggatggct
aagggagagccacgttt-3'

VEE3'-4R
                                     (SEQ ID NO: 14)
5'-aaacgtggctctcccttagccatccgagtggacgtgcgtcctccttc
ggatgcccaggtcg-3'
```

Each pair of forward and reverse oligonucleotides (e.g., VEE1F with VEE1R, VEE2F with VEE2R, etc) were mixed, phosphorylated, denatured, and slowly annealed. Then the 4 pairs of annealed oligonucleotides were mixed together, ligated to each other, digested with enzymes NotI and PmeI, gel purified using a QIAquick gel extraction kit, and ligated to the VCR-backbone that had been previously digested with the same enzymes, gel purified and treated with shrimp alkaline phosphatase. Positive clones for the fragment were verified by sequencing. This construct was called VCR-3'drib.

Next, the 5' end of VEE genome was inserted. This fragment was generated using overlapping oligonucleotides to cover the genome region of VEE strain Trinidad donkey (see GENBANK reference, above) from nucleotide 1 to the restriction site HpaI. The primers with VEE nucleotide 1 also contained an upstream MluI site followed by the SP6 promoter immediately 5' of VEE nucleotide 1. All oligonucleotides were mixed in one reaction, phosphorylated, denatured, slowly annealed, and ligated. After inactivating the ligase, the DNA was digested with the enzymes MluI and HpaI, gel purified using the QIAquick gel extraction kit and ligated to VCR-3'drib that had been previously digested with the same restriction enzymes, gel purified and treated with shrimp alkaline phosphatase. The positive clones for the insert were verified by sequencing. This intermediate construct was called VCR-F1-3'drib.

Finally, the region of VEE containing the subgenomic promoter was cloned into VCR-F1-3'drib. This region (fragment 13, FIG. 1) corresponds to the sequence between restriction site SwaI and nucleotide 7561 of the VEE Trinidad donkey strain genome. The fragment was generated using overlapping oligonucleotides corresponding to the Trinidad Donkey strain sequence, with the exception of the oligonucleotide corresponding to the 3' end of the fragment that was modified to carry an additional restriction sites (BbvCI) to allow later insertion of heterologous sequences under the control of the subgenomic promoter. All oligonucleotides were mixed in one reaction, phosphorylated, denatured, slowly annealed, and ligated. After inactivating the ligase, the DNA was digested with the enzymes SwaI and BbvCI, gel purified using QIAquick gel extraction kit and ligated to VCR backbone that had been previously digested with the same restriction enzymes, gel purified and treated with shrimp alkaline phosphatase. Clones positive for the insert were verified by sequencing and one clone, VF13-14, was subsequently repaired by deleting a small insertion and reconfirming by sequencing. The clone was next digested with SwaI-NotI, the 600 bp fragment was gel purified using the QIAquick gel extraction kit and ligated to VCR-F1-3'drib that had been previously digested with the same restriction enzymes, gel purified and treated with shrimp alkaline phosphatase. The positive clones for the insert were verified and the construct was called VCR-DH.

Construction Of tDH-Vgly, tDH-VE2-120 and tDH-V$_{NTR}$-glydl160

Figure 3:
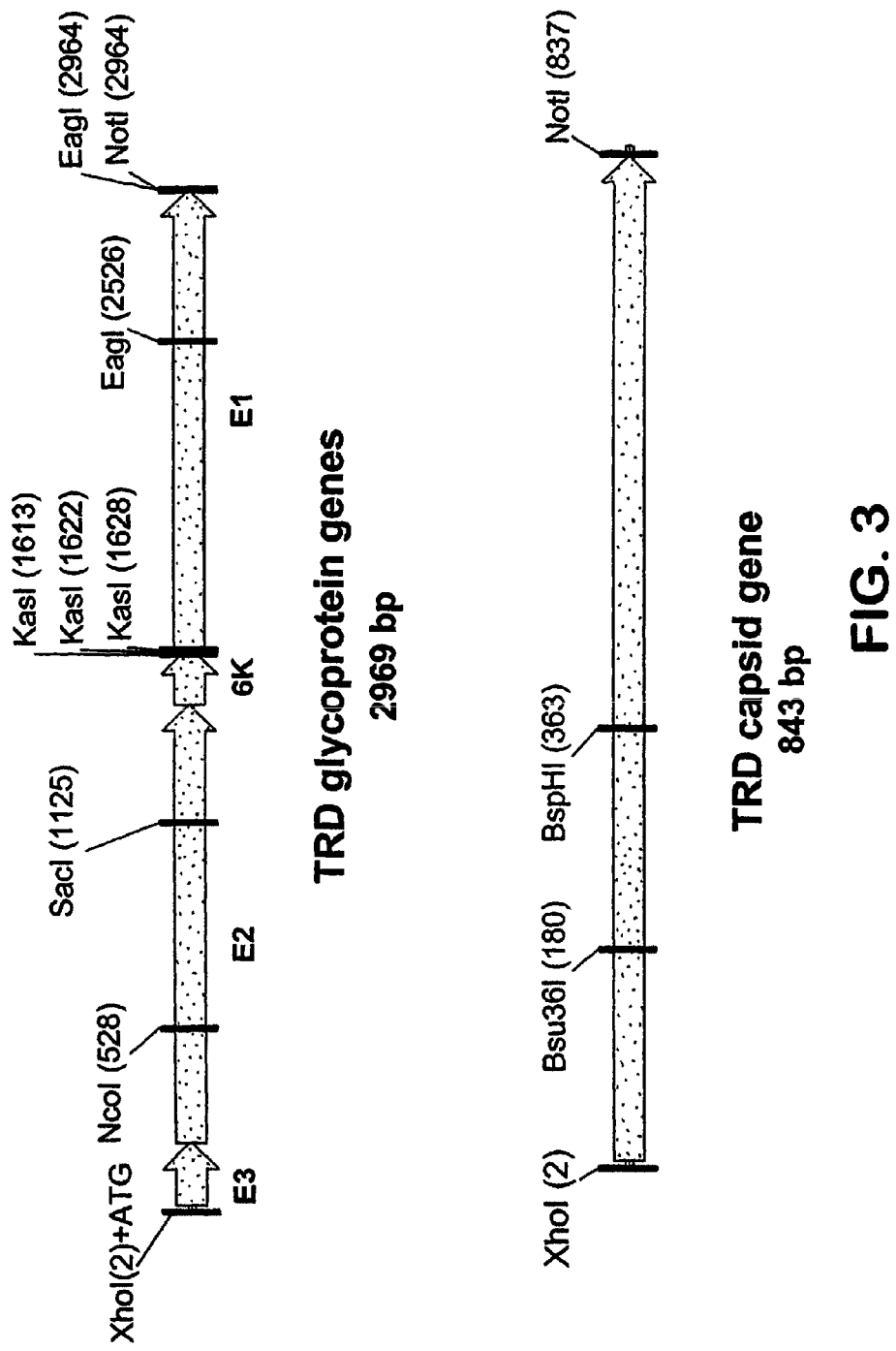
FIG. 3 depicts VEE gene synthesis fragments and restriction sites used for assembly of structural protein genes.

The VEE Trinidad donkey strain glycoprotein genes were generated using overlapping oligonucleotides that were designed based on the published GENBANK sequence. To allow expression from the appropriate vector packaging cassettes, an ATG codon, in-frame with the glycoprotein gene open reading frame, was added immediately preceding the first amino acid of E3, and a XhoI site and NotI site were added respectively at the 5' and 3' end of the glycoprotein gene sequences. Gene synthesis was performed by using overlapping PCR to generate five separate fragments spanning the entire glycoprotein sequence (FIG. 3). The fragments were assembled stepwise into a single fragment in pGEM using the restriction sites indicated in FIG. 3. A small nucleotide deletion within the KasI sites was corrected by standard site-directed mutagenesis. The final clone was verified by sequencing and designated pGEM-Vgly. Then the glycoprotein gene sequence was transferred from pGEM into tDH using the XhoI-NotI sites and the final clone was designated tDH-Vgly.

A construct similar to tDH-Vgly that also contains the attenuating mutation at E2 amino acid 120 present in the TC83 vaccine strain of VEE was constructed in an analogous way. Plasmid pGEM-Vgly was subjected to standard site directed mutagenesis and the E2-120 mutation confirmed by sequencing. Then, the VEE E2-120 glycoprotein sequence was transferred from pGEM into tDH using the XhoI-NotI sites and the construct was confirmed by sequencing and designated tDH-VE2-120.

Plasmid tDH-V$_{NTR}$-glydl160 is a tDH defective helper construct (see above) containing a SIN glycoprotein sequence from the human dendritic cell tropic strain described previously (Gardner et al., ibid), in which the SIN derived subgenomic 5' NTR and the synthetic XhoI site were substituted by the following VEE subgenomic 5' NTR sequence (5'-ACTACGACATAGTCTAGTCCGCCAAG) (SEQ ID NO: 53). This sequence was inserted such that it immediately precedes the glycoprotein ATG initiation codon. The construct is also known as tDH-V$_{UTR}$-glydl160 to reflect the interchangeable nomenclature for the subgenomic 5' non-translated region (NTR), also referred to as untranslated region (UTR).

Construction of VCR-DH-Vgly, VCR-DH-VE2-120 and VCR-DH-Sglydl160

The VEE glycoprotein gene sequence between the ATG and the restriction site NcoI was amplified by PCR using the following oligonucleotides.

```
VGBbvCI  5'-atatatctcgagcctcagcatgtcactagtgaccacc
         atgt-3'
         (SEQ ID NO: 15)

VGNcoIR  5'-atatataaattccatggtgatggagtcc-3'
         (SEQ ID NO: 16)
```

After PCR amplification, the fragment was digested with BbvCI and NcoI, and gel purified using QIAquick gel extraction kit. Separately, the VEE E2-120 glycoprotein region from NcoI to NotI was prepared by digesting pGEM-VE2-120 with these enzymes followed by gel purification. The two fragments were mixed and ligated to VCR-DH that had been previously digested with BbvCI and NotI, gel purified, and treated with alkaline phosphatase. Positive clones for the insert were verified by sequencing and designated VCR-DH-VE2-120. To obtain VCR-DH-Vgly the NcoI-XbaI fragment was obtained from pGEM-Vgly and used to substitute the same fragment in VCR-DH-VE2-120.

A SIN glycoprotein with the human DC+ phenotype was obtained from a defective helper plasmid E3ndl160/dlRRV, modified from Gardner et al. (2000, ibid) (WO 01/81609). Plasmid E3ndl160/dlRRV was digested with XhoI, treated it with Klenow fragment to blunt the ends, then digested with NotI. The 3 kb fragment was gel purified using QIAquick gel extraction kit and ligated to VCR-DH that had been previously digested with BbvCI, treated with Klenow fragment, digested with NotI, and treated with alkaline phosphatase. A positive clone for the insert was designated VCR-DH Sglydl160. Similarly, a defective helper construct containing the SIN LP strain-derived envelope glycoproteins (Gardner et al., 2000, ibid) was constructed.

Construction of VCR-DH-Vcap, VCR-DH-Scap and tDH-Vcap

The VEE capsid gene was synthesized using overlapping oligonucleotides, also designed based on the published GENBANK sequence of the VEE Trinidad donkey strain, with the addition of a XhoI site and a Kozak consensus sequence adjacent to the capsid ATG, and a NotI site at the 3'-end. The oligonucleotides were mixed and used for a 25-cycle PCR amplification reaction. The PCR generated fragment was digested with the restriction sites XhoI and NotI, gel purified and cloned into the vector pBS-SK+. Positive clones for the insert were verified by sequencing. Finally, the capsid sequence was further modified to insert a termination codon at it's 3'-end by PCR amplification in a 25-cycle reaction with the following oligonucleotides.

```
TRDCtR 5-atatatatgcggccgcttaccattgctcgcagttctccg-3'
     (SEQ ID NO: 17)
     contains stop codon in frame with the last
     amino acid capsid TRDNtF 5' atatatctcgagccaccatgttcccgttccagccaatg-3'
     (SEQ ID NO: 18)
```

The product was purified with QIAquick PCR purification kit, digested with XhoI and NotI and ligated to the backbone of tDH vector that had been previously prepared by digestion with XhoI and NotI, gel purification, and alkaline phosphatase treatment. Positive clones for the insert were verified by sequencing and the construct was designated tDH-Vcap.

The same PCR product was also digested with XhoI, treated with T4 DNA polymerase to blunt XhoI site, digested with NotI, gel purified, and ligated to VCR-DH that had been previously digested with BbvCI, treated with T4 DNA polymerase to blunt BbvCI site, digested with NotI, gel purified, and treated with alkaline phosphatase. Positive clones for the insert were verified by sequencing and the construct was designated VCR-DH-Vcap.

The SIN capsid sequence was obtained from a previously described defective helper and the 800 bp fragment was gel purified using QIAquick gel extraction kit and ligated to VCR-DH that had been previously digested with BbvCI, treated with Klenow fragment, digested with NotI, and treated with alkaline phosphatase. A positive clone for the insert was designated VCR-DH-Scap.

Example 3

Generation of Alphavirus Replicon Particle Chimeras with Hybrid Capsid Protein

In the case of hybrid capsid protein using elements obtained from both SIN and VEE, a series of hybrid capsid proteins were constructed containing the amino terminal (RNA binding) portion from SIN and the carboxy terminal (glycoprotein interaction) portion from VEE. Additional constructs with the opposite portions also were derived. The site at which such portions were fused varied by construct and necessarily factored into account the differences in overall length of these two capsid proteins, with SIN capsid being 264 amino acids and VEE capsid being 275 amino acids. Sites of fusion to generate the capsid hybrids are indicated in the table below, as well as in FIG. 4.

| Name of capsid chimera | NH2-terminus | COOH-terminis |
|---|---|---|
| S113V | SIN(1-113) | VEE(125-275) |
| S129V | SIN(1-129) | VEE(141-275) |
| S127V | SIN(1-127) | VEE(139-275) |
| S116V | SIN(1-116) | VEE(128-275) |
| S109V | SIN(1-109) | VEE(121-275) |
| V141S | VEE(1-141) | SIN(130-264) |

Each of the hybrid capsid constructs was generated by PCR amplification of two overlapping fragments, one coding for the amino-terminus of capsid protein from SIN or VEE, and the other coding for the carboxy-terminus of capsid protein from the opposite virus (VEE or SIN, respectively).

Fragments containing SIN capsid sequences were amplified from a defective helper construct (Gardner et al., 2000, ibid), and fragments containing VEE capsid sequences were amplified from construct VCR-DH-Vcap (above). The following oligonucleotides were used:

| Fragment | 5' oligonucleotide | 3' oligonucleotide |
|---|---|---|
| SIN(1-113) | SINNtF 5'atatatctcgagccaccatgaatag aggattctttaacatg-3' (SEQ ID NO: 19) containing the restriction site XhoI (nt. 7-13), the Kozak consensus sequence for optimal protein translation (nt. 14-18), and sequence complementary to SIN capsid (nts 19-48) | S113R 5'gggaacgtcttgtcggcctccaacttaagtg-3' (SEQ ID NO: 20) with nt. 1-10 complementary to VEE capsid sequence and nt. 11-31 to SIN capsid sequence |
| SIN(1-129) | SINNtF | SINNtR 5'gaataacttccctccgaccacacat gcgtgcccgatgacatctc-3' (SEQ ID NO: 21) with nt. 1-24 complementary to VEE capsid sequence and nt. 25-44 to SIN capsid sequence |

-continued

| Fragment | 5' oligonucleotide | 3' oligonucleotide |
|---|---|---|
| SIN(1-127) | SINNtF | S127R<br>5'ccacacaagcgtacccgatgacatctccgtcttc-3'<br>(SEQ ID NO: 22)<br>with nt. 1-13<br>complementary to VEE<br>capsid sequence and nt.<br>14-34 to SIN capsid sequence |
| SIN(1-116) | SINNtF | S116R<br>5'catgattgggaacaatctgtcggcctccaac-3'<br>(SEQ ID NO: 23)<br>with nt. 1-9 complementary<br>to VEE capsid sequence and<br>nt. 10-31 to SIN capsid sequence |
| SIN(1-109) | SINNtF | s109R<br>5'gtcagactccaacttaagtgccatgcg-3'<br>(SEQ ID NO: 24)<br>with nt. 1-6 complementary<br>to VEE capsid sequence and<br>nt. 7-27 to SIN capsid sequence. |
| SIN(130-264) | SINCtF<br>5'gggaagataaacggctacgctctg<br>gccatggaaggaaagg-3'<br>(SEQ ID NO: 25)<br>with nt. 1-21<br>complementary to VEE<br>capsid sequence and nt.<br>22-40 to SIN capsid sequence | SINCtR<br>5'atatatatgcggccgctcaccactcttctgtcccttc-3'<br>(SEQ ID NO: 26)<br>with the restriction site NotI<br>(nt. 9-16) and nt. 17-39<br>complementary to SIN<br>capsid sequence. |
| VEE(125-275) | TRD125F<br>5'gccgacaagacgttcccaatcatgttggaag-3'<br>(SEQ ID NO: 27)<br>with nt. 1-9 complementary<br>to SIN capsid sequence and<br>nt. 10-31 to VEE capsid sequence | TRDCtR<br>5'atatatatgcggccgcttaccattgctcgcagttctccg-3'<br>(SEQ ID NO: 28)<br>with the restriction site NotI<br>(nt. 9-16) and nt. 17-39<br>complementary to VEE capsid |
| VEE(141-275) | TRDCtF<br>5'gagatgtcatcgggcacgcatgtgt<br>ggtcggagggaagttattc-'<br>(SEQ ID NO: 29)<br>with nt. 1-20<br>complementary to SIN<br>capsid sequence and nt.<br>21-44 to VEE capsid sequence | TRDCtR |
| VEE(139-275) | TRD139F<br>5'-tcatcgggtacgcttgtgtggtcg-3'<br>(SEQ ID NO: 30)<br>with nt. 1-8 complementary<br>to SIN capsid sequence and<br>nt. 9-24 to VEE capsid sequence | TRDCtR |
| VEE(128-275) | TRD128F<br>5'gacagattgttcccaatcatgttggaaggg-3'<br>(SEQ ID NO: 31)<br>with nt. 1-11<br>complementary to SIN<br>capsid sequence and nt.<br>12-30 to VEE capsid sequence | TRDCtR |
| VEE(121-275) | TRF121F<br>5'acttaagttggagtctgacaagacgttcccaatc-3'<br>(SEQ ID NO: 32)<br>with nt. 1-13<br>complementary to SIN<br>capsid sequence and nts.<br>14-34 to VEE capsid sequence | TRDCtR |

-continued

| Fragment | 5' oligonucleotide | 3' oligonucleotide |
|---|---|---|
| VEE(1-141) | TRDNtF<br>5'atatatctcgagccaccatgttcccgttccagccaatg-3'<br>(SEQ ID NO: 33)<br>with the restriction site XhoI<br>(nt. 7-13), the Kozak<br>consensus sequence for<br>optimal protein translation<br>(nt. 14-18), and nts. 19-48<br>complementary to VEE<br>capsid sequence | TRDNtR<br>5'cctttccttccatggccagagcgtagccgtttatcttccc-3'<br>(SEQ ID NO: 34)<br>with nt. 1-19<br>complementary to SIN<br>capsid sequence and nt.<br>20-40 to VEE capsid sequence |

The oligonucleotides listed above were used at 2 μM concentration with 0.1 μg of the appropriate template plasmid DNA in a 30 cycle PCR reaction, with Pfu polymerase as suggested by the supplier and with the addition of 10% DMSO. The general amplification protocol illustrated below.

| Temperature (° C.) | Time (Min.) | No. Cycles |
|---|---|---|
| 94 | 2 | 1 |
| 94 | 0.5 | |
| 60 | 0.5 | 10 |
| 72 | 2 | |

The amplified fragments were purified from agarose gel using QIAquick gel extraction kit, and then an aliquot (1/15th) of each fragment was used as template for a second PCR amplification. The two fragments were mixed as follows and amplified with Vent Polymerase as suggested by supplier, with the addition of 10% DMSO:
SIN(1-129)+VEE(141-275)
SIN(1-127)+VEE(139-275)
SIN(1-116)+VEE(128-275)
SIN(1-113)+VEE(125-275)
SIN(1-109)+VEE(121-275)
VEE(1-141)+SIN(130-264)

One PCR amplification cycle was performed under the following conditions:

| Temperature (° C.) | Time (Min.) | No. Cycles |
|---|---|---|
| 94 | 2 | 1 |
| 94 | 0.5 | |
| 42 | 1 | 1 |
| 72 | 3 | |

For the SIN NH2-terminus/VEE COOH-terminus fusions, the SINNtF and TRDCtR primers, containing the XhoI and NotI restriction sites, were added at 2 μM concentration and the complete PCR amplification was performed as follows:

| Temperature (° C.) | Time (Min.) | No. Cycles |
|---|---|---|
| 94 | 2 | 1 |
| 94 | 0.5 | |
| 60 | 0.5 | 30 |
| 72 | 2 | |

The PCR product was purified using the QIAquick kit, digested with XhoI and NotI, gel purified from agarose gel as described above, and ligated to plasmid tDH that had also been digested with XhoI and NotI to remove the existing capsid gene insert. Clones containing the newly generated hybrid inserts were verified by sequencing and the new defective helper constructs for use in producing chimeric particles were designated tDHS129Vcap, tDHS127Vcap, tDHS116Vcap, tDHS113Vcap, and tDHS109Vcap.

Similarly, for the VEE NH2 terminus/SIN COOH terminus fusions, the TRDNtF and SINCtR primers, containing the XhoI and NotI restriction sites, were added at 2 μM concentration. The PCR amplification was performed using the same conditions as above. This PCR fragment was then digested with XhoI, blunted, digested with NotI and ligated to plasmid VCR-DH-Vcap that had been digested with BbvCI, blunted and digested with NotI. Clones containing the inserts were verified by sequencing and the new defective helper construct was designated VCR-DH-S129Vcap.

The capsid chimeras were then tested for their efficiencies of replicon packaging with the appropriate alphavirus replicon vector and glycoprotein defective helper. Specifically, the chimeras with the SIN-derived NH2-terminus and the VEE-derived COOH-terminus were tested for their ability to package SIN replicons with VEE glycoproteins. This was accomplished as follow. The plasmid DNA encoding for the chimeras (tDHS129Vcap, tDHS127Vcap, tDHS116Vcap, tDHS113Vcap, and tDHS109Vcap) were linearized with the unique restriction site PmeI and used for in vitro transcription as described previously (Polo et al., 1999, ibid). Each transcript was co-transfected by electroporation into BHK cells together with helper RNA expressing the VEE glycoproteins and SIN replicon RNA expressing GFP, as described previously (Polo et al. 1999, ibid). Transfected cells were incubated at 34° C. for 24 hr, at which time the culture supernatants were collected, clarified by centrifugation, serially diluted, and used to infect naïve BHK-21 cells for approximately 14 hr. Enumeration of GFP positive cells allowed for quantitation of input vector particles and the vector particle stock. The data below indicate that the efficiency of packaging for a SIN/VEE chimeric particle can be increased quite dramatically, particularly with the S113V hybrid capsid protein.

| Capsid | Glycoprotein | Replicon | Particle titer |
|---|---|---|---|
| S129V | VEE | SIN | $4e^5$ IU/ml |
| S127V | VEE | SIN | $2e^4$ IU/ml |
| S116V | VEE | SIN | $1.6e^6$ IU/ml |
| S113V | VEE | SIN | $1.1e^7$ IU/ml |

Similarly, each chimera transcript was co-transfected by electroporation into BHK cells together with 1) helper RNA expressing the VEE glycoproteins with the E2-120 attenuating mutation tDHVE2-120 and 2) SIN replicon RNA expressing GFP. Transfected cells were incubated at 34° C. for 24 hr, at which time the culture supernatants were collected, clarified by centrifugation, serially diluted, and used to infect naïve BHK-21 cells for approximately 14 hr. Enumeration of GFP positive cells allowed for quantitation of input vector particles and titer determination for the replicon vector particle stock. The data below confirm that the hybrid capsid can dramatically increase the packaging efficiency of the SIN replicon in particles containing the VEE glycoproteins.

| Capsid | Glycoprotein | Replicon | Particle titer |
|---|---|---|---|
| S129V | VE2-120 | SIN | $1.6e^7$ IU/ml |
| S127V | VE2-120 | SIN | $5.1e^5$ IU/ml |
| S116V | VE2-120 | SIN | $4.7e^7$ IU/ml |
| S113V | VE2-120 | SIN | $9.3e^7$ IU/ml |
| S | VE2-120 | SIN | $1e^2$ IU/ml |

Similar experiments with the VCR-GFP RNA, cotransfected with RNA helpers coding for the hybrid capsid S129Vcap and the SIN glycoproteins, produced particles with average titers of 1.6e7 IU/ml demonstrating that the ability of this hybrid protein to efficiently package VEE-derived vector RNA.

To further maximize the capsid-RNA and capsid-glycoprotein interactions, an additional construct was made, whereby the S113V hybrid capsid protein gene was incorporated into the genome of a chimeric alphavirus, comprising the 5'-end, 3'-end, subgenomic promoter and nonstructural protein genes of SIN, and the glycoprotein genes from VEE.

To generate such construct, an initial genome-length SIN cDNA clone from which infectious RNA may be transcribed in vitro was generated by assembling replicon and structural gene sequences from the previously described human dendritic cell tropic SIN variant, SINDCchiron (ATCC#VR-2643, deposited Apr. 13, 1999). DNA clones used encompassing the entire genome of SINDCchiron virus (Gardner et al., ibid; WO 00/61772) were assembled using standard molecular biology techniques and methods widely known to those of skill in the art (Rice et al. (1987) *J. Virol.* 61:3809-3819; and U.S. Pat. No. 6,015,694). The genomic SIN clone was designated SINDCSP6gen.

Subsequently, the existing SIN structural proteins were replaced with the hybrid capsid S129Vcapsid and VEE glycoproteins in the following manner. A fragment from TDH-S129V containing part of the hybrid capsid was generated by PCR amplification with the following oligonucleotides:

```
S/VcVg1R                              (SEQ ID NO: 54)
atatatatggtcactagtgaccattgctcgcagttctccg ScAatIIF                              (SEQ ID NO: 55)
gccgacagatcgttcgacgtc
```

The oligonucleotides were used 2 µM concentration with 0.1 µg of the appropriate template plasmid DNA in a 30 cycle PCR reaction, with Pfu polymerase as suggested by the supplier and with the addition of 10% DMSO. The general amplification protocol is illustrated below.

| Temperature (° C.) | Time (Min.) | No. Cycles |
|---|---|---|
| 94 | 2 | 1 |
| 94 | 0.5 | |
| 60 | 0.5 | 30 |
| 72 | 2 | |

The PCR fragment was gel purified using QIAquick gel extraction kit. Another fragment containing the VEE glycoprotein fragment was obtained from tDHVE2-120 by digestion with SpeI and PmeI, and gel purification. The two fragments were mixed and ligated to an 11 kb fragment obtained from the SINDCSP6gen clone by digestion with SpeI and PmeI, gel purification, and treatment with shrimp alkaline phosphatase. The positive clones for the inserts were confirmed by sequencing and this intermediate was called SrS129VcVg-interm. To restore the authentic 3'-end in the genomic clone, the PsiI-PsiI fragment was regenerated by PCR with the following oligonucleotides

```
PsiIFd1N                             (SEQ ID NO: 123)
5' ATATATATTTATAATTGGCTTGGTGCTGGCTACTATTGTGGCCATGT
ACGTGCTGACCAACCAGAAACATAATTGACCGCTACGCCCCAATGATC
C-3'

PsiR                                 (SEQ ID NO: 124)
5'-GGCCGAAATCGGCAAAATCCC-3'
``` at 2 µM concentration with 0.1 µg of the infectious clone plasmid DNA in a 30 cycle PCR reaction, with Vent polymerase as suggested by the supplier and with the addition of 10% DMSO. The general amplification protocol illustrated below.

| Temperature (° C.) | Time (Min.) | No. Cycles |
|---|---|---|
| 94 | 2 | 1 |
| 94 | 0.5 | |
| 60 | 0.5 | 30 |
| 72 | 2 | |

The fragment was digested with PsiI, gel purified, and ligated to SrS129VcVg-interm that had also been digested with PsiI, gel purified, and treated with shrimp alkaline phosphatase. The positive clones for the insert were confirmed by sequencing and the final construct was designated SrS129VcVg.

To construct a similar full-length cDNA clone containing the hybrid S113V capsid, a fragment containing part of SIN sequences upstream of the capsid gene and the capsid gene encoding for aa1-113 was generated using the following oligonucleotides

```
Sic7082F                             (SEQ ID NO: 125)
5'-CACAGTTTTGAATGTTCGTTATCGC-3'
```

S113R (see above)
at 2 µM concentration with 0.1 µg of the SIDCSP6gen construct in a 30 cycle PCR reaction, with Pfu polymerase as suggested by the supplier and with the addition of 10% DMSO. The general amplification protocol illustrated below.

| Temperature (° C.) | Time (Min.) | No. Cycles |
|---|---|---|
| 94 | 2 | 1 |
| 94 | 0.5 | |
| 60 | 0.5 | 30 |
| 72 | 2 | |

The fragment was gel purified using QIAquick gel extraction kit, and $^1/_{10}{}^{th}$ of the reaction was mixed with fragment VEE (141-275) (see above, construction of all hybrid capsid genes). One PCR amplification cycle was performed under the following conditions:

| Temperature (° C.) | Time (Min.) | No. Cycles |
|---|---|---|
| 94 | 2 | 1 |
| 94 | 0.5 | |
| 42 | 1 | 1 |
| 72 | 3 | |

Then oligonucleotides Sic7082F and TRDCtR were added at 2 µM concentration and the complete PCR amplification was performed as follows:

| Temperature (° C.) | Time (Min.) | No. Cycles |
|---|---|---|
| 94 | 2 | 1 |
| 94 | 0.5 | |
| 60 | 0.5 | 30 |
| 72 | 2 | |

The PCR product was purified using the QIAquick kit, digested with BstZ17I and SapI, gel purified from agarose gel as described above, and ligated to two fragments generated from plasmid SrS129VcVg that had also been digested with BstZ17I and SapI to remove the existing capsid gene insert. Clones containing the newly generated hybrid inserts were verified by sequencing and the new construct was designated SIN113CVgly.

In order to generate virus, the SIN113CVgly construct was linearized with PmeI, transcribed in vitro using SP6 polymerase and the RNA transfected into BHK cells. Progeny virus was harvested and passaged in cells, with the infectious titer increasing to levels approaching $10^9$ PFU/mL. A non-plaque purified stock of this chimeric SIN virus, designated SIN113CVgly virus (deposited with ATCC May 31, 2001, PTA-3417), was then used as the source of RNA for cloning and sequencing by standard molecular biology techniques (e.g., those described above) to identify additional genetic determinants that provide this high level of chimeric particle packaging. Individual genetic determinants are readily incorporated back into the replicon and defective helper packaging constructs of the present invention using teachings provided herein.

It is understood that the non-plaque-purified stock of chimeric SIN virus deposited with ATCC number may contain numerous genotypes and phenotypes not specifically disclosed herein that are considered part of the present invention. Persons having ordinary skill in the art could easily isolate individual phenotypes and or genotypes using plaque purification techniques and sequence the isolated chimeric SIN using procedures known to those having ordinary skill in the art and disclosed herein.

Example 4

Generation of Alphavirus Replicon Particle Chimeras with Hybrid Glycoproteins

In the case of a hybrid envelope glycoprotein using elements obtained from both SIN and VEE, hybrid E2 glycoproteins were constructed containing the cytoplasmic tail (e.g., capsid binding portion) from SIN and the transmembrane and ectodomain portions from VEE. Additional constructs with the opposite portions can also be derived. In some embodiments, it may also be desirable to include hybrids for both the E2 and E1 glycoproteins, and to include hybrids that encompass the transmembrane domain.

To demonstrate an increased efficiency of chimeric particle packaging using such glycoprotein hybrids, a modified VEE-derived glycoprotein was constructed wherein the E2 tail was substituted with SIN-derived E2 cytoplasmic tail. The fusion was done at the conserved cysteine residue (amino acid residue 390, both VEE and SIN E2) which is at the boundary between the transmembrane domain and the cytoplasmic tail (FIG. 5). The chimera construct was generated by PCR amplification of two overlapping fragments one of which included part of VEE E2 glycoprotein sequence upstream the cytoplasmic tail and part of the SIN E2 cytoplasmic tail. The second fragment included part of the SIN E2 cytoplasmic tail and VEE 6K protein.

The first fragment was amplified from the construct VCR-DH-Vgly using the following oligonucleotides:

VE2F:
(SEQ ID NO: 35)
5'-atatatcaggggactccatcaccatgg-3'

(nts 7-27 are complementary to the VEE glycoprotein and include the NcoI site)

VSGE2R:
(SEQ ID NO: 36)
5'-gggattacggcgtttggggccagggcgtatggcgtcaggcactcacg gcgcgctttgcaaaacagccaggtagacgc-3'

(nts 1-56 are SIN E2 cytoplasmic tail sequence, and nts. 57-77 are complementary to VEE glycoprotein sequence)

The second fragment was amplified from the same plasmid using the following primers:

VSGE3F:
(SEQ ID NO: 37)
5'gccccaaacgccgtaatcccaacttcgctggcactcttgtgctgcgtt aggtcggccaatgctgagaccacctgggagtccttg-3'

(nts. 1-63 correspond to part of the SIN E2 cytoplasmic tail sequence, and nts 64-84 are complementary to the VEE glycoproteins)

VEE3'-1R:
(SEQ ID NO: 38)
5'-ccaatcgccgcgagttctatgtaagcagcttgccaattgctgctgta tgc-3'

(complementary to VCR-DH Vgly downstream the glycoprotein open reading frame)

The oligonucleotides listed above were used at 2 µM concentration with 0.1 µg of template plasmid DNA VCR-DH-Vgly in a 30 cycles PCR reaction with Pfu Polymerase as suggested by the supplier, with the addition of 10% DMSO. The amplification protocol is shown below.

| Temperature (° C.) | Time (Min.) | No. Cycles |
|---|---|---|
| 94 | 2 | 1 |
| 94 | 0.5 | |
| 60 | 0.5 | 30 |
| 72 | 2 | |

The two amplified fragments were purified from agarose gel using QIAquick gel extraction kit, and then an aliquot (1/10th) of each fragment was used as templates for a second PCR amplification. The two fragments were mixed with Pfu Polymerase as suggested by supplier with the addition of 10% DMSO. One PCR amplification cycle was performed:

| Temperature (° C.) | Time (Min.) | No. Cycles |
|---|---|---|
| 94 | 2 | 1 |
| 94 | 0.5 | |
| 42 | 1 | 1 |
| 72 | 3 | |

Then the VE2NtF and VEE3'-1R primers were added 2 µM concentration and the PCR amplification was performed as follows:

| Temperature (° C.) | Time (Min.) | No. Cycles |
|---|---|---|
| 94 | 2 | 1 |
| | 0.5 | |
| 60 | 0.5 | 30 |
| 72 | 2 | |

The PCR product was purified using the QIAquick kit, digested with NcoI and NotI, gel purified from agarose gel as described above, and ligated to plasmid tDH-Vgly that had also been digested with NcoI and NotI and purified from agarose gel. Clones containing the inserts were verified by sequencing and the construct was designated tDH-VglySE2tail.

To demonstrate increased packaging of particles generated with such a glycoprotein chimera, plasmid DNA tDH-VglySE2tail was linearized with the single restriction enzyme PmeI and RNA transcribed in vitro. The RNA was co-transfected together with SINCR-GFP replicon RNA and the defective helper RNA encoding SIN capsid protein. Transfected cells were incubated at 34° C. for 24 hr, at which time the culture supernatant was collected, clarified by centrifugation, serially diluted, and used to infect naïve BHK-21 cells for approximately 14 hr. Using flow cytometry analysis the particles titers were determined and shown to be $2e^3$ IU/ml. This result showed that some low efficiency interaction is occurring between the glycoprotein chimera and SIN capsid.

To further increase the efficiency of chimeric particle packaging with a hybrid glycoprotein, additional constructs were generated. Alignment of the cytoplasmic tails from VEE and SIN (FIG. 5) shows the differences at 10 residues, four of which are conservative changes. Interestingly, the residues at positions 394 and 395 are charged in the SIN glycoprotein, while they are hydrophobic in VEE. Such difference might affect the E2 functionality. Site directed mutagenesis using a PCR amplification method was used to change the two residues in the construct tDH-VglySE2tail as follow:

| Name | Nucleotide change | amino acid change | Mutagenic oligos |
|---|---|---|---|
| tDH-M1 (SEQ ID NO: 39) | $A_{2151}$ to C | $Glu_{395}$ to Ala | M1R 5'GTATGGCGTCA GGCACGCACGGCG CGCTTTG-3' (SEQ ID NO: 39) M1F 5'AGCGCGGCGT GCGTGCCTGACG CCATACGCC-3' (SEQ ID NO: 40) |
| tDH-M2 (SEQ ID NO: 40) | $C_{2147}$ to G and $G_{2148}$ to T | $Arg_{394}$ to Val | M2R 5'ATGGCGTCAG GCACTCAACGCG CGCTTTGCAAAA C-3' (SEQ ID NO: 41) M2F 5'TTTGCAAAGCG CGCGTTGAGTGCC TGACGCCATAC-3' (SEQ ID NO: 42) |
| tDH-M3 | $A_{2151}$ to C, $C_{2147}$ to G, and $G_{2148}$ to T | $Arg_{394}$-$Glu_{395}$ to Val-Ala | M3R 5'ATGGCGTCAG GCACGCAACGCG CGCTTTGCAAAA C-3' (SEQ ID NO: 43) M3F 5'TTTGCAAAGCG CGCGTTGCGTGCC TGACGCCATAC-3' (SEQ ID NO: 44) |

The mutagenized constructs were verified by sequencing. To quantitate packaging by these new glycoprotein hybrids, the plasmid DNAs were linearized with the single restriction enzyme PmeI and transcribed in vitro. Each mutant RNA was then co-transfected together with the SINCR-GFP replicon RNA and defective helper RNA encoding SIN capsid. Transfected cells were incubated at 34° C. for 24 hr, at which time the culture supernatant was collected, clarified by centrifugation, serially diluted, and used to infect naïve BHK-21 cells for approximately 14 hr for titer analysis. Using flow cytometry analysis, the particle titers were determined and it was observed that the packaging efficiency was increased approximately 7-fold with M1.

Alternatively, and similarly to the capsid approach, it was possible to substitute the VEEglyco-E2 SIN tail chimera into a full-length alphavirus cDNA clone from which infectious virus may be obtained, and use the chimeric virus genome to select naturally arising chimeric particle variants with further increased efficiency of packaging. A large plaque phenotype may be indicative of high titer virus. This infectious chimera was constructed as follow. A fragment containing mostly SIN capsid sequence was generated by PCR in order to have a few nucleotides added to its 3' end corresponding to the VEE glycoprotein sequence and containing the SpeI restriction site. This fragment was amplified from a human DC-tropic SIN infectious clone construct (Gardner et al., ibid) with the following primers:

ScAatIIF:
(SEQ ID NO: 45)
5'-gccgacagatcgttcgacgtc-3'

ScVg1R:
(SEQ ID NO: 46)
5'-atatatatggtcactagtgaccactcttctgtcccttccg-3'

These oligonucleotides were used at 2 µM concentration with 0.1 µg of template plasmid DNA in a 30 cycles PCR reaction with Pfu Polymerase as suggested by the supplier with the addition of 10% DMSO. The amplification protocol is shown below.

| Temperature (° C.) | Time (Min.) | No. Cycles |
|---|---|---|
| 94 | 2 | 1 |
| 94 | 0.5 | |
| 60 | 0.5 | 30 |
| 72 | 2 | |

The amplified fragment (450 bp) was cleaned using QIAquick PCR purification kit, digested with AatII and SpeI, gel purified using QIAquick gel extraction kit. A fragment (3.4 kb) containing the VEE glycoprotein-SIN E2tail and SIN 3' UTR was generated by restriction digest from tDH-VE2Stail using the enzymes SpeI-PmeI and gel purification with QIAquick gel extraction kit. This fragment and the PCR fragment were mixed and ligated together to plasmid DNA from the infectious clone that had been also digested with AatII and PmeI, treated with Shrimp alkaline phosphatase, and gel purified. Positive clones for the insert were verified by sequencing. Finally, to restore the authentic full-length clone 3'-end, the PsiI-PsiI fragment was regenerated as described for SrS129VcVg and the new construct was designated SrcVgSE2t.

SrcVgSE2t was linearized with the single restriction enzyme PmeI and transcribed in vitro. The RNA was transfected into BHK cells. Transfected cells were incubated at 37° C. for 24 hr, at which time the culture supernatant was collected, clarified by centrifugation, and used to infect naïve BHK-21 cells. Approximately 24 hr post-infection the supernatant was collected, clarified by centrifugation, and used to infect naïve BHK-21 cells again. At 24 hr post-infection a few viral plaques were observed, so the supernatant was collected, clarified and used for to infect two flasks of naïve BHK. The cells of one flask were collected 16 hr post-infection and total RNA was extracted using Trizol (Gibco-BRL). The infection in the other flask was allowed to continue for another 8 hrs and extensive cytopathic effects were observed in the cells indicating that large amounts of virus had been produced.

Total RNA extracted from the infected cells was used to amplify and clone capsid and glycoprotein sequences using RT-PCR. The reverse transcription was primed with either polydT or with the specific primer

```
VglyR:
                                       (SEQ ID NO: 47)
5'-atatatatgcggccgctcaattatgtttctggttggtcag-3'
```

The cDNA was then used for PCR amplification of the capsid sequence with the primers SINNtF containing a XhoI site and SINCtR containing a NotI site, and of the glycoprotein sequence with the primers VglyR containing a NotI site and

```
VglyF:
                                       (SEQ ID NO: 48)
5'-atatatctcgagccgccagccatgtcactagtgaccac-3'
``` containing a XhoI site. Both fragments were cleaned using QIAquick PCR purification kit, digested with XhoI and NotI, gel purified using QIAquick gel extraction kit and separately ligated to tDH that had been previously digested with XhoI and NotI, gel purified and treated with shrimp alkaline phosphatase. Ten clones for the capsid fragment were sequenced to identify the possible adaptive mutation(s). However, no mutations were found in the capsid region indicating that either such mutations can only occur in the glycoprotein sequences or that, since the RNA came from unpurified plaques, the 10 clones did not completely represent the entire adapted population.

Repeating the same analysis on RNA derived from 5 individual viral plaques still did not lead to identification of capsid adaptive mutations. The glycoprotein sequence from one plaque (P3) revealed the presence of two amino acid changes at positions 380 of E2 (Val to Gly) and 391 (Lys to Arg), also numbered relative to wild-type E2. Interestingly, the amino acid 380 of E2 is conserved between Sindbis and at least three VEE strains (TRD, MAC10 and 6119) and amino acid 390, which is the first residue in of the cytoplasmic tail, is a Lys in the SIN glycoprotein sequences and MAC10 and 6119 but is a Arg in the TRD strain. This might indicate that the location of these residues play a role in the correct conformation of the transmembrane-cytoplasmic tail, which might stabilize the interactions between the glycoproteins and the capsid, and may be further exploited as part of the present invention.

To test if this double mutation could increase packaging efficiency, a 998 bp fragment (NcoI-MfeI) containing both mutations was swapped into tDH-VglySE2tail generating tDH-VglySE2tail-P3. Then, plasmid DNA tDH-VglySE2tail-P3 was linearized with the single restriction enzyme PmeI and RNA transcribed in vitro. The RNA was co-transfected together with SINCR-GFP replicon RNA and the defective helper RNA encoding SIN capsid protein. Transfected cells were incubated at 34° C. for 24 hr, at which time the culture supernatant was collected, clarified by centrifugation, serially diluted, and used to infect naïve BHK-21 cells for approximately 14 hr. Using flow cytometry analysis, the particles titers were determined and the efficiency of packaging increased 50 fold with respect to VglySE2tail. Also, in the context of a hybrid VEE glycoprotein containing the SE2tail and the VEE E2-120 attenuating mutation (VE2-120/SE2tail), the P3 mutations increased the packaging efficiency 200 fold.

Example 5

Figure 6:
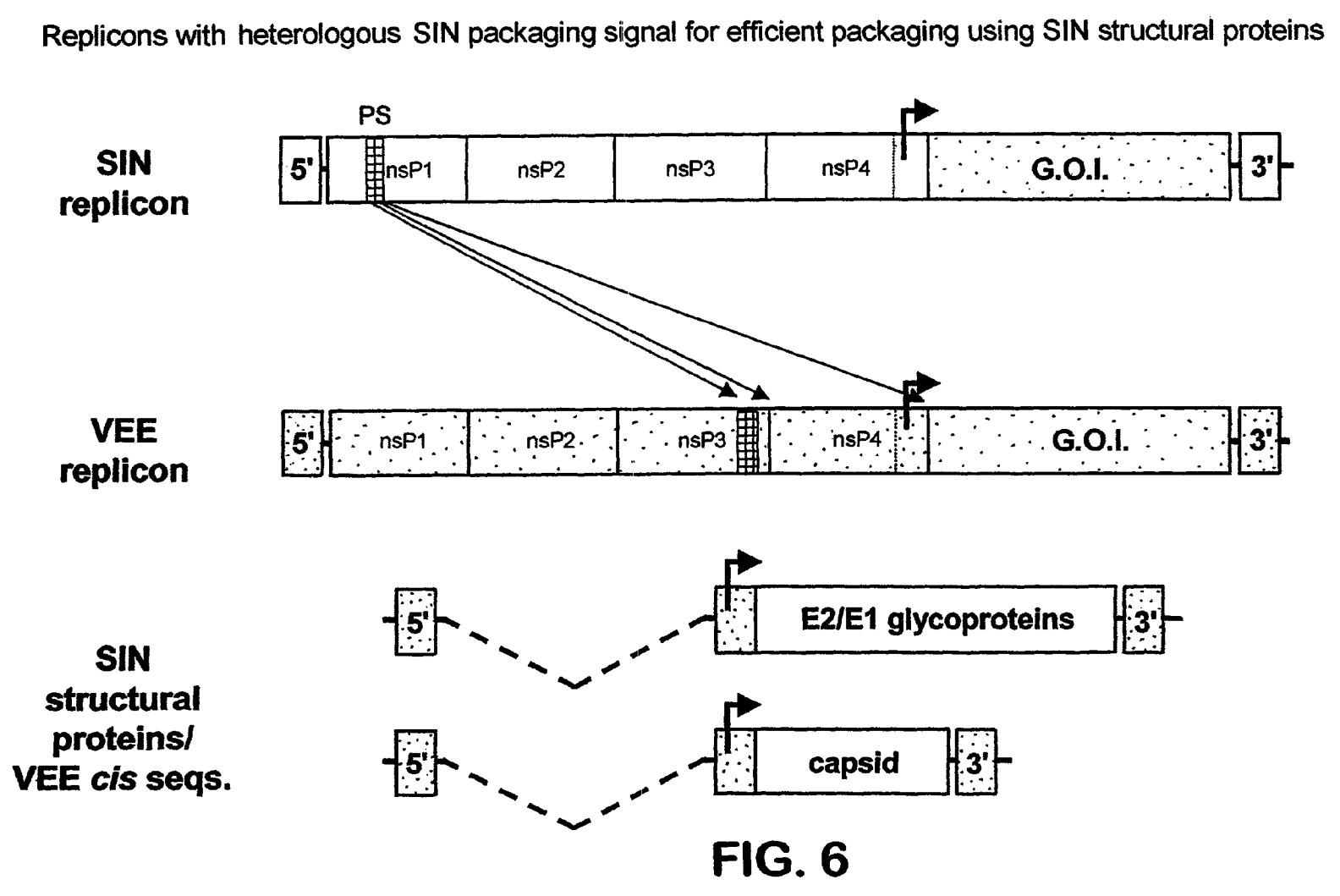

Generation of Alphavirus Replicon Particle Chimeras with Hybrid Packaging Signal To generate a highly efficient packaging system for a VEE replicon within Sindbis virus structural proteins, the well-defined RNA packaging signal from SIN was inserted at various points within a VEE replicon. For this work the 132 nucleotide (nt.) core packaging signal from SIN was separately inserted into each of three different sites (FIG. 6) within the VEE-TRD replicon constructed in Example 1. Four chimeric replicons were generated. Chimera-1A and Chimera-1B were the names given to the constructs in which the SIN packaging signal was inserted at the 3' end of the VEE-TRD nsP4 gene, just prior to the nsP4 stop codon. The Chimera-2 replicon contains the SIN packaging signal in-frame, at the C-terminus of nsP3, substituting at the nucleotide level for a 102 bp segment of nsP3. Finally, the Chimera-3 replicon resulted from the insertion of the SIN packaging signal at the end of nsP3, just prior to the nsP3 termination codon.

It is also contemplated by the inventors that the teachings herein may provide a unique opportunity to modify replicons and eukaryotic layered vector initiation systems derived from any BSL-3 alphavirus (e.g., VEE), such that they may be treated as BSL-2 or BSL-1 constructs by reducing the nucleotide sequence derived from the parental virus to less than two-thirds genome-length.

A) Chimera 1A, 1B:

A complicating factor for the construction of these chimeras lay in the fact that the subgenomic promoter of all alphaviruses overlaps the last approximately 100 nucleotides of nsP4. In order to place the SIN packaging signal at the end of nsP4 while maintaining a functional subgenomic promoter in the replicon vector for driving expression of the heterologous gene, it was necessary to alter the codon usage of the last 80 nt. of nsP4 (upstream of the inserted SIN sequence) to eliminate their ability to bind the replicase complex. Simultaneously, the VEE subgenomic promoter region was reconstituted downstream of the nsP4 stop codon by duplicating the native sequence of a portion of the 3' end of nsP4 thought to be part of the subgenomic promoter recognition sequence. Chimera 1A and 1B differ by the length of reconstituted nsP4 sequence that was added back to regenerate a functional subgenomic promoter: to −80 for CHIMERA-1A (FIG. 7), to −98 for CHIMERA-1B (FIG. 8).

Chimera 1A and 1B were prepared by cleaving pVCR-DH, an intermediate construct from the re-assembly phase of the pVCR construction described (above), with MscI and AscI. Into this vector was inserted either of two tripartite synthetic oligonucleotides coding, as described above, the last 80 bp or so of nsP4 with non-native codon usage, followed by the SIN packaging signal (in frame) and nsP4 termination codon, followed by the duplicated terminal 80 or 98 bp of native nsP4 sequence. The oligonucleotides were designed to provide synthetic full duplex strands that were treated in the same manner as was described earlier for the replicon synthesis. Sequence verified clones from this ligation were digested with MscI and AscI, and the oligo fragment bearing the SIN packaging signal was substituted into the vector fragment of pVCR, digested similarly. The resulting final constructs for each was called pVCR/CHIMERA-1A and pVCR/CHIMERA-1B. To evaluate the functionality of these constructs, the GFP gene was cloned into each using the unique BbvCI and NotI sites downstream of the subgenomic promoter and the constructs were designated VCR-Chim1A-GFP and VCR-Chim1B-GFP respectively.

Figure 9:
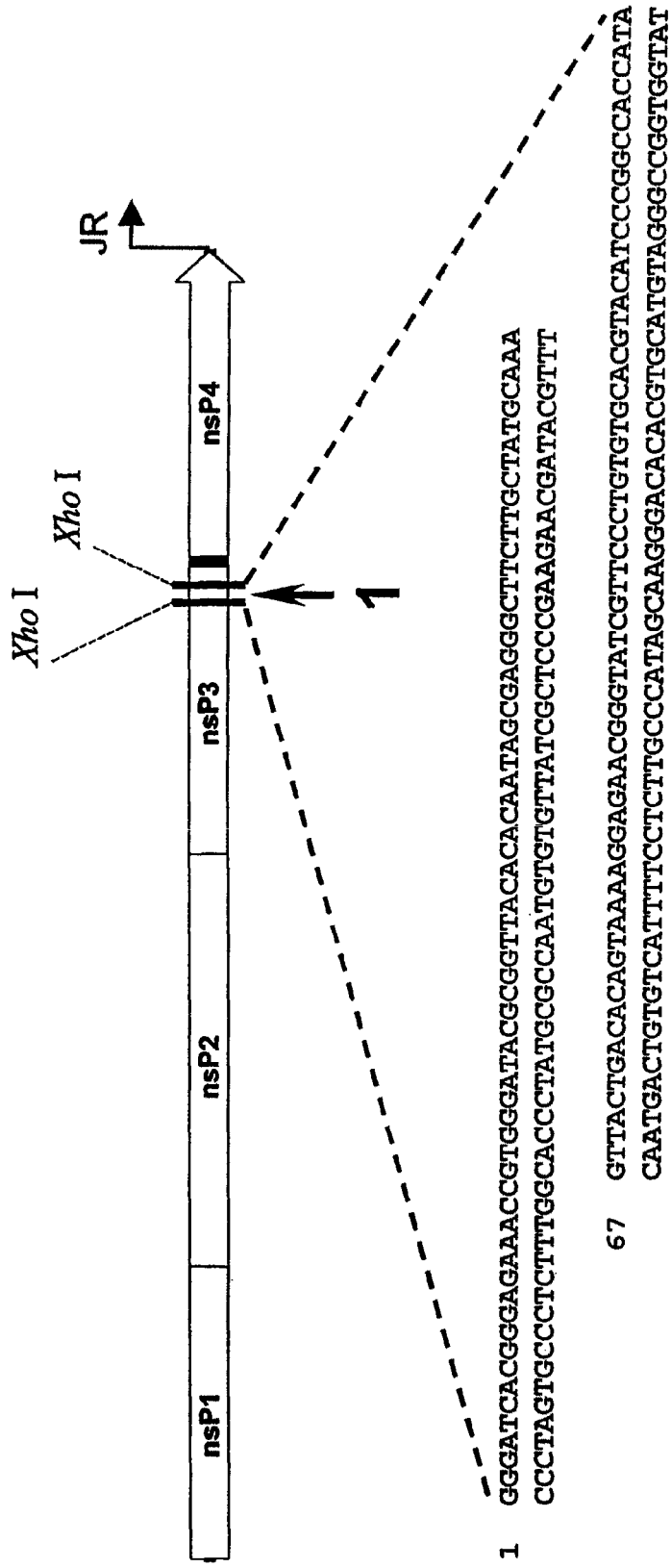
FIG. 9 depicts SIN/VEE packaging Chimera number 2 insertion of SIN packaging signal into a VEE nonstructural protein gene (nsP3) deletion (SEQ ID NO: 98).

B) Chimera2:

Chimera-2 was prepared by cleavage of the VEE-replicon assembly intermediate, pCMVkm2-(del XhoI/Cell)-VEE 9/10, from example 1, coding for a portion of VEE nsP3 and nsP4 bounded by the MamI and BlnI sites of the replicon. XhoI cleavage of this vector deletes a 102 bp segment of VEE nsP3. Into this cleaved vector was inserted a PCR product consisting of the SIN packaging signal flanked by terminal, in-frame, XhoI sites (FIG. 9). The template for this amplification was pSINCP and Pfu DNA polymerase was used with the following oligonucleotide primers.

```
5' Pr:
                                    (SEQ ID NO: 49)
5'-ATATCTCGAGAGGGATCACGGGAGAAAC-3'

3' Pr:
                                    (SEQ ID NO: 50)
5'-AGAGGAGCTCAAATACCACCGGCCCTAC-3'
```

Resulting clones were validated for sequence and orientation. One positive clone was digested MamI-BlnI to generate a fragment used to substitute for the native MamI-BlnI segment of pVCR. The resulting plasmid was called pVCR/CHIMERA-2. The GFP gene was cloned into this vector as described above for pVCR/CHIMERA-1A, -1B, generating VCR-Chim2-GFP. It should be appreciated that the region of deletion in nsP3 was selected based on convenient restriction endonuclease sites in the plasmid DNA construct. Additional deletions that remove larger regions of nsP3 are also contemplated by the present invention and can be performed readily by one of skill in the art.

Figure 10:
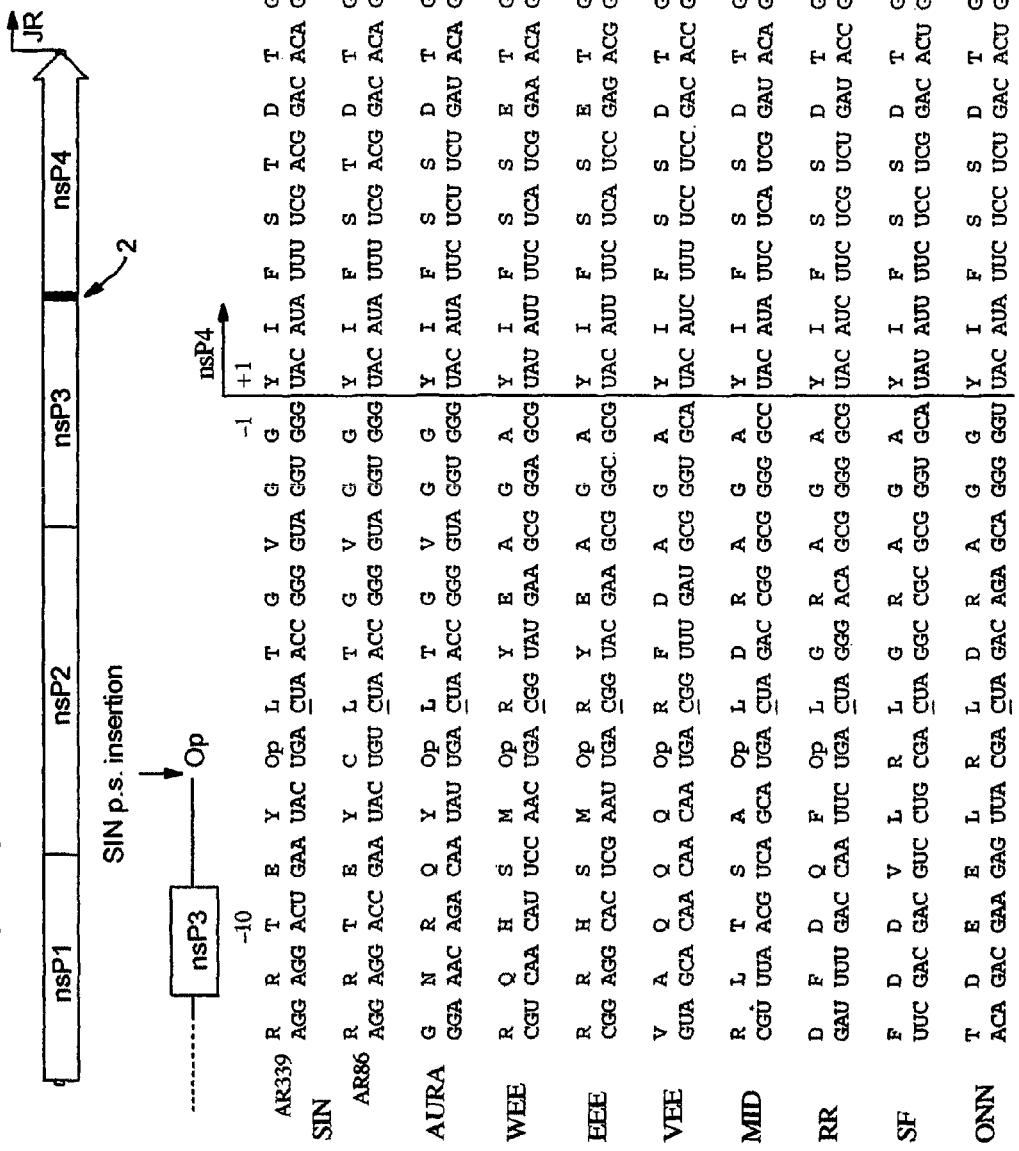
FIG. 10 depicts SIN/VEE packaging chimera number 3 insertion of SIN packaging signal at carboxy-terminus of VEE nsP3 (SEQ ID NOS: 99 to 118).
Figure 11:
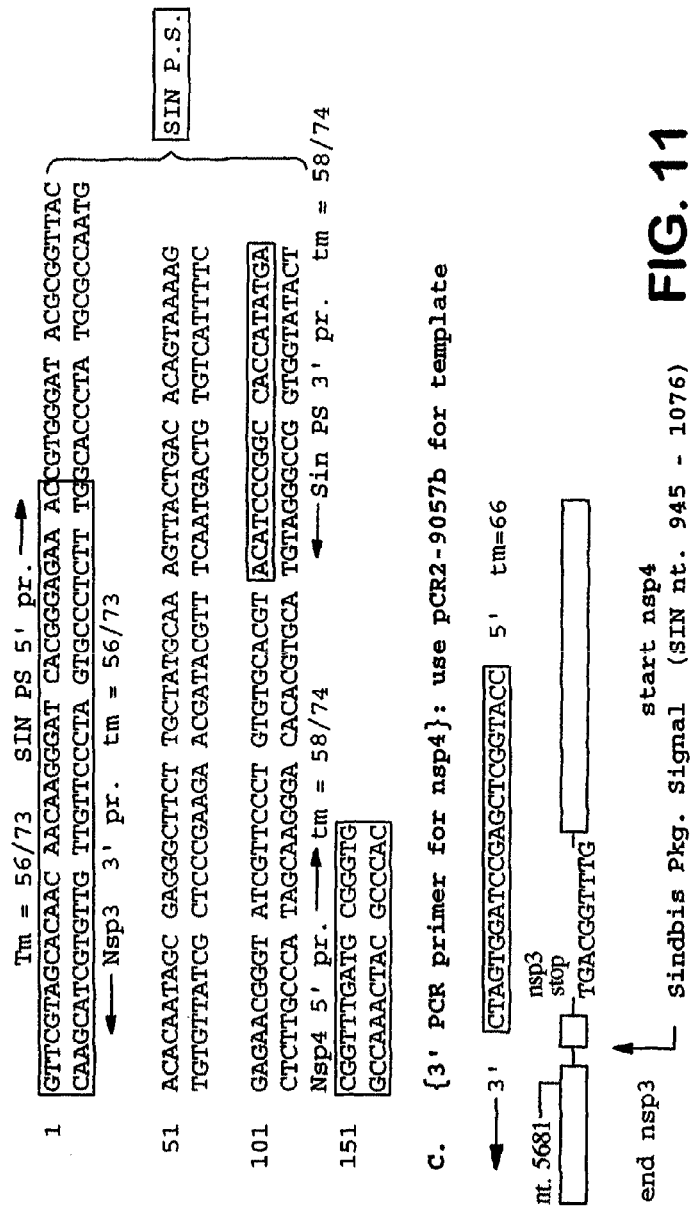
FIG. 11 depicts modification of nsP3/nsP4 termini for SIN packaging signal (SEQ ID NOS: 119 to 122).

C) Chimera-3:

Chimera-3 was prepared by modification of a replicon fragment from example 1, pCR2-9057b, which contained a portion of replicon fragments 9+10, encoding the region of the junction of VEE nsP3 and nsP4. Insertion of the SIN packaging site was accomplished by overlapping PCR using Pfu DNA polymerase and two sets of primers which amplified two products across the junction in pCR2-9057b and which appended SIN packaging signal sequence tails to the resulting products. Similarly the SIN packaging signal was amplified from pSINCP with primers that appended nsP3 and nsP4 sequence tails, respectively, at the 5' and 3' ends of the product. See FIGS. 10 and 11 for detail of this strategy including primer sequences. The three PCR products were diluted, mixed, denatured, re-annealed, and extended with Pfu DNA polymerase to create a chimeric overlap template for amplification utilizing the external nsP3 and nsP4, 5' and 3' primers. This product was digested with XbaI and MluI and cloned into a similarly digested intermediate cloning vector, pCM-Vkm2 (zur Megede, *J. Virol.* 74:2628, 2000). To place the chimera in the context of pVCR, the pCMVkm2/CHIMERA-3 intermediate was digested with MamI (5') and SacI (3') and co-ligated with a SacI-BlnI fragment from pVCR (nt. 5620-6016 of pVCR) into the MamI/BlnI vector fragment of pVCR. The resulting construct was called pVCR/CHIMERA-3. The GFP gene was cloned into this vector as described above for pVCR/CHIMERA-1A, -1B, generating VCR-Chim3-GFP.

To test the ability of these constructs to be packaged by Sindbis structural proteins, the plasmids VCR-Chim1A-GFP, VCR-Chim1b-GFP, VCR-Chim2-GFP, and VCR-Chim3-GFP were linearized with the single restriction enzyme PmeI and RNA transcribed in vitro. The RNA was co-transfected together with defective helper RNAs encoding SIN capsid and glycoproteins from constructs VCR-DH-Sglydl160 and VCR-DH-Scap also linearized with PmeI. Transfected cells were incubated at 34° C. for 24 hr, at which time the culture supernatants were collected, clarified by centrifugation, serially diluted, and used to infect naïve BHK-21 cells for approximately 14 hr. Using flow cytometry analysis the particle titers were determined. The results below showed that three chimeras could be packaged efficiently by the SIN structural proteins. Chimera 1A was not expressing GFP and it was not determined whether this was due to a defect in the subgenomic transcription or in the RNA replication.

| Replicon | Structural proteins | Titers |
|---|---|---|
| VCR-Chimera1A | SIN | 0 |
| VCR-Chimera1B | SIN | $3.8E^7$ Iu/ml |
| VCR-Chimera2 | SIN | $9.6E^7$ Iu/ml |
| VCR-Chimera1A | SIN | $3E^7$ Iu/ml |

Construction of Chimera 2.1

To further reduce the amount of parental VEE virus sequence present in the pVCR-Chimera2 replicon, the 3' NTR (also known as 3' sequence required for nonstructural protein-mediated amplification, or 3' UTR) sequence from VEE was removed in its entirety and replaced by the 3' NTR from SIN. Plasmid SINCR-GFP (Garner et al., 2000 ibid.) was digested with NotI and PmeI, the 466 bp fragment was gel purified using QIAquick gel extraction kit and ligated to both pVCR-Chimera2 and VCR-Chim2-GFP that had been previously digested with NotI and PmeI, gel purified and treated with shrimp alkaline phosphatase. Positive clones were verified and the constructs designated VCR-Chim2.1 and VCR-Chim2.1-GFP. These constructs now differ from the parental VEE virus genome by the deletion of multiple VEE sequences (e.g., region of nsP3, structural protein genes, 3' NTR).

To test the functionality of the new chimera replicon vector configuration, plasmid VCR-Chim2.1-GFP was linearized with the single restriction enzyme PmeI and RNA transcribed in vitro. The RNA was co-transfected together with defective helper RNAs encoding SIN capsid and glycoproteins from constructs VCR-DH-Sglydl160 and VCR-DH-Scap also linearized with PmeI. Transfected cells were incubated at 34° C. for 24 hr, at which time the culture supernatants were collected, clarified by centrifugation, serially diluted, and used to infect naïve BHK-21 cells for approximately 14 hr. Using flow cytometry analysis, the particle titers were determined to be the same titers as VCR-Chim2-GFP, demonstrating that deletion of the native 3' NTR and replacement with a heterologous alphavirus 3' NTR (e.g., SIN 3' NTR) maintains functionality in the VEE replicon.

Alternatively, as a means to reduce the overall VEE-derived sequences in VCR-Chimera2, the 3'NTR was reduced to a minimal sequence containing the 19nt conserved CSE. Such a modified 3'NTR was generated using overlapping oligonucleotides:

```
Vred2F 5'-ggccgcttttcttttccgaatcggattttgttttttaat-3'  SEQ ID NO: 77

Vred2R 5'-attaaaaacaaaatccgattcggaaaagaaaagc-3'  SEQ ID NO: 78

VEE3F   see VCR-DH construction for oligonucleotide
VEE3R   sequences
VEE4F
VEE4R
```

Each pair of forward and reverse oligonucleotides (e.g., Vred2F with Vred2R, VEE2F with VEE2R, etc) were mixed, phosphorylated, denatured, and slowly annealed. Then the 3 pairs of annealed oligonucleotides were mixed together, ligated to each other, digested with enzymes NotI and PmeI, gel purified using a QIAquick gel extraction kit, and ligated to the VCR-Chim2-GFP that had been previously digested with the same enzymes to delete the full length 3'NTR, gel purified and treated with shrimp alkaline phosphatase. Positive clones for the fragment were verified by sequencing. This construct was called VCR-Chim2.2-GFP.

To confirm functionality of this chimera replicon vector configuration, plasmid VCR-Chim2.2-GFP was linearized with the single restriction enzyme PmeI and RNA transcribed in vitro. The RNA was co-transfected together with defective helper RNAs encoding SIN capsid and glycoproteins from constructs VCR-DH-Sglydl160 and VCR-DH-Scap also linearized with PmeI. Transfected cells were incubated at 34° C. for 24 hr, at which time the culture supernatants were collected, clarified by centrifugation, serially diluted, and used to infect naïve BHK-21 cells for approximately 14 hr. Using flow cytometry analysis, the particle titers were determined to be the similar to VCR-Chim2-GFP, demonstrating that reducing the size of the 3' NTR from 117 bp to 37 bp and replacement maintains functionality of the replicon.

Similar to the above replicon vectors for use as RNA or replicon particles, alphavirus DNA-based replicons that function directly within a eukaryotic cell (e.g., Eukaryotic Layered Vector Initiation Systems) may be derived by one of skill in the art, using the teachings provided herein. Such DNA-based replicons may be deleted of a variety of parental virus sequences for example, including, but not limited to, sequences from the nsP3 carboxy terminal region, structural protein gene region, 3' CSE region, and the like.

Example 6

Use of Different Structural Proteins for Delivery of Replicon RNA

An HIV antigen was expressed from SIN replicon RNA packaged with either SIN or VEE structural proteins, and from VEE replicon RNA packaged with either SIN or VEE structural proteins as follows. Specifically, a fragment containing the heterologous gene sequence encoding codon-optimized HIV p55gag (zur Megede (2000) *J. Virol.* 74:2628) from plasmid pCMVKm2.GagMod.SF2 was inserted into the SINCR replicon vector (Gardner et al., 2000, ibid) at the XhoI-NotI sites, into the VCR replicon vector at the BbvCI-NotI sites and into the VCR-Chim2.1 vector at the BbvCI-MfeI sites. The p55gag encoding replicon constructs were designated SINCR-p55gag, VCR-p55gag, and VCR-Chim2.1-p55gag, respectively. To produce SIN, VEE and chimera replicon particles expressing p55gag, the above plasmids were linearized with the single restriction enzyme PmeI and RNA transcribed was in vitro. The RNA was co-transfected together with defective helper RNA encoding for the appropriate structural proteins which were transcribed from the PmeI linearized plasmids as shown below:

| Particles | Replicon | Caspid | Glycoproteins |
| --- | --- | --- | --- |
| SIN | SINCR-p55gag | SINdl-cap (Polo et al., 1999, ibid) | tDH-VUTR-Sglydl160 |
| VEE | VCR-p55gag | VCR-DH-Vcap | VCR-DH-VE2-120 |
| SINrep/VEEenv | SINCR-p55gag | tDH-S113Vcap | tDH-VUTR-Sglydl160 |
| VEErep/SINenv | VCR-Chim2.1p55gag | VCR-DH-Scap | VCR-DH-Vglydl160 |

Transfected cells were incubated at 34° C., supernatants collected at 20 hr and 36 hr, followed by clarification by centrifugation, and chromatographic purification as described previously (WO 01/92552).

Particle titers were determined by intracellular staining for gag expression in BHK21 cells infected for 16 hrs with serial dilution of purified particle preparations. The cells were first permeabilized and fixed with Cytofix/Cytoperm Kit (Pharmingen), then stained for intracellular p55gag with FITC conjugated antibodies to HIV-1 core antigen (Coulter). Using flow cytometry analysis, the percentage of gag positive cells were determined and used to calculate the particle titers.

Figure 12:
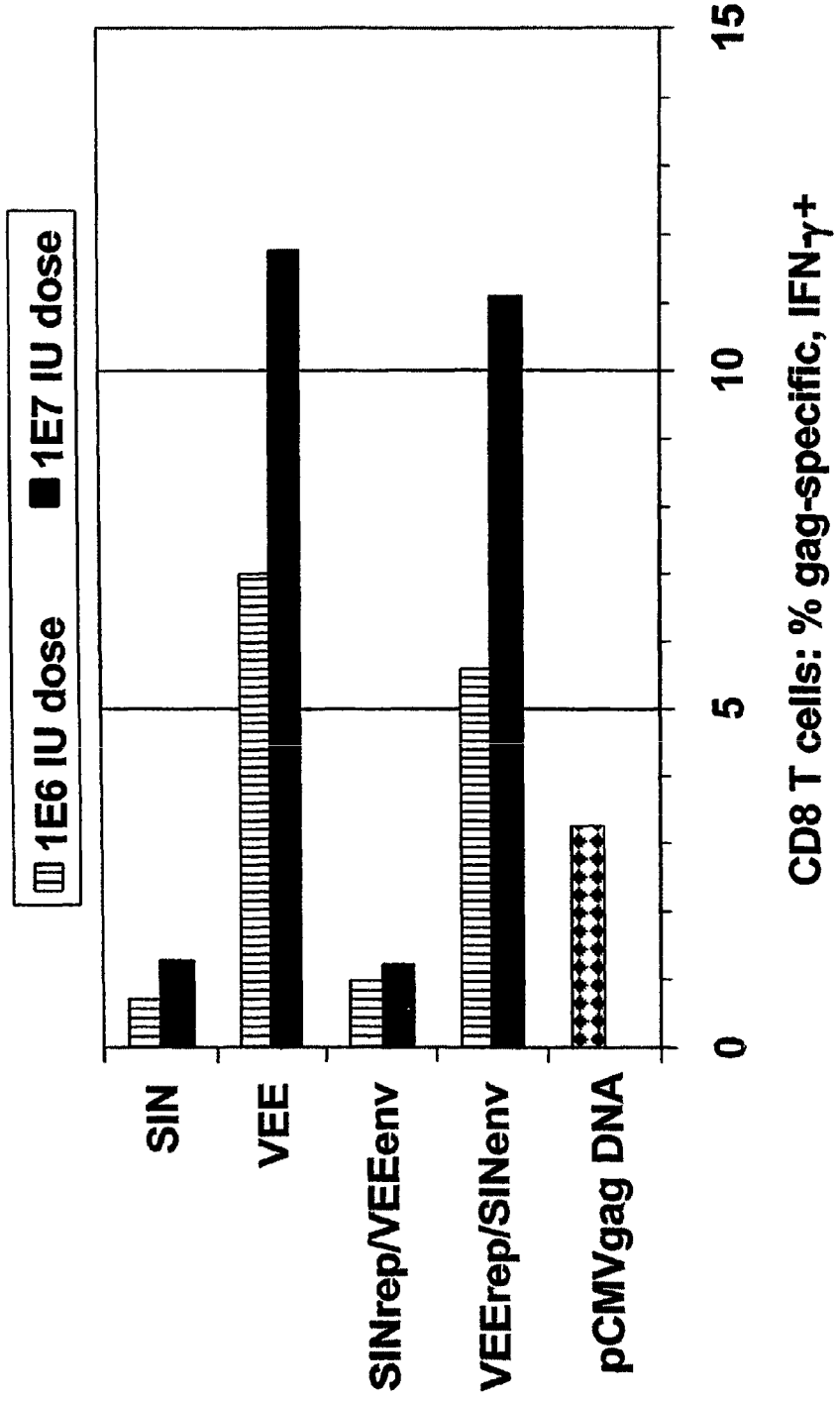
FIG. 12 is a graph depicting immunogenicity of alphavirus replicon particle chimeras expressing an HIV antigen. In particular, the graph depicts HIV p55gag-specific CD8+ T cell responses in mice primed with alphavirus replicon encoding HIV gag sequences.

Immunogenicity in rodent models was determined after immunization with the different alphavirus replicon particle preparations expressing HIV p55gag, at doses of $10^6$ or $10^7$ IU replicon particle doses (FIG. 12). Each was found to be immunogenic and one chimera, VEErep/SINenv, was found to be a particularly potent immunogen.

Additionally, such replicon particles may be used in combination with another vaccine modality (e.g., DNA, non-alphavirus viral vector), such as in a prime-boost regime. For example, mice were first immunized with a plasmid DNA vaccine encoding HIV p55gag (pCMVKm2.GagMod.SF2), and then boosted with each of the above alphavirus replicon particles expressing the p55gag antigen (FIG. 13). Each of the alphavirus replicon particles was found to be immunogenic, boosting the CD8+ T cell responses, and one chimera, VEErep/SINenv, was found to be a particularly potent immunogens.

Demonstration of sequential immunization of rodents or primates with alphavirus replicon particles, such as the above replicon particles, differing in their structural proteins, may be performed using a variety of routes (e.g., intramuscular, intradermal, subcutaneous, intranasal) and with dosages ranging from $10^3$ IU up to $10^8$ IU, or greater. For example, primates are immunized first with $10^7$ SINCR-p55gag particles containing VEE structural proteins in 0.5 mL of PBS diluent, by a subcutaneous route. The same materials are then administered a second time 30 days later, by the same route of injection. Approximately 6-12 months later, the animals are then immunized one or more times with $10^7$ SINCR-p55gag particles containing SIN structural proteins in 0.5 mL of PBS diluent, by an intramuscular route. Demonstration of immunogenicity is performed using standard assays and may be compared to parallel animals that received only a single type of replicon particle at time of administration.

The preceding examples have described various techniques suitable for preparing chimeric alphavirus particles using nucleic acids, nonstructural proteins and structural proteins, as well as portions thereof, derived from two different alphaviruses. However, one of ordinary skill in the art, using the teaching provided herein, could prepare chimeric alphavirus particles from three or more viruses without undue experimentation. In would be logical to combine the teachings found herein with the teachings of other relevant technical disclosures generally available to those skilled in the art including, but not limited to, patents, patent applications, scientific journals, scientific treatise and standard references and textbooks.

For example, alphavirus chimeric particles are made using SIN replicon vectors and at least two defective helper RNA molecules. The replicon RNA encodes for SIN non-structural proteins, a VEE packaging signal and a heterologous gene of interest. The first defective helper RNA encodes for a hybrid capsid protein having a VEE RNA binding domain and a WEE glycoprotein interaction domain. The second defective helper RNA encodes for WEE glycoprotein. The resulting chimeric alphavirus particles have nucleic acid derived from SIN with a VEE/WEE hybrid capsid and a WEE envelope glycoprotein.

In another example, a chimeric alphavirus particle is made in accordance with the teachings of the present invention where a SIN replicon having SIN non-structural proteins and a heterologous gene of interest is combined with two defective helper RNA molecules. The first defective helper RNA encodes for a hybrid capsid having a SIN RNA binding domain and a SFV glycoprotein interaction domain. The second defective helper RNA encodes for a hybrid glycoprotein having a SFV cytoplasmic tail with the remainder of the glycoprotein envelope provided by VEE. The resulting chimeric alphavirus particle has SIN nucleic acids with a heterologous gene of interest encapsidated in a SIN/SFV hybrid capsid with a SFV/VEE hybrid envelope glycoprotein, the outer ectodomain portion of the glycoprotein being derived from VEE.

In yet another example four different alphaviruses are used to prepare the chimeric alphavirus particle. In this example a SIN replicon RNA encoding for SIN non-structural proteins, a VEE packaging signal and a heterologous gene of interest is provided. A first defective helper RNA encodes for a hybrid capsid having a VEE RNA binding domain and a WEE glycoprotein interaction domain. The second defective helper RNA encodes for a hybrid glycoprotein having a WEE cytoplasmic tail with the remainder of the glycoprotein being provided by SFV. The resulting chimeric alphavirus particle has SIN RNA and a heterologous gene of interest, a VEE/WEE hybrid capsid and a WEE/SFV hybrid glycoprotein, the outer ectodomain portion of the glycoprotein being derived from SFV.

Many other combinations are possible and the preceding examples serve to illustrate the present invention's tremendous versatility. Therefore, these non-limiting examples represent only a few of the numerous chimeric alphavirus particles that can be made in accordance with the teachings of the present invention.

Example 7

Use of Alphavirus Replicon Vectors and Defective Helpers with Different Control Elements To produce alphavirus replicon particles using vector (e.g., replicon RNA, eukaryotic layered vector initiation system) and packaging (e.g., defective helper, structural protein expression cassette) components with different control elements, a wide variety of combinations may be utilized according to the present invention. For example, a SIN plasmid DNA-based replicon (eukaryotic layered vector initiation system) can be constructed to contain a different 3' sequence required for nonstructural protein-mediated amplification (3' CSE) than contained in the structural protein expression cassettes of a SIN packaging cell line. More specifically, modification of the SIN 3' end to incorporate a polyadenylation signal derived from the bovine growth hormone gene is performed as described below. The resulting sequence:

```
                                    (SEQ ID NO: 56)
GCGGCCGCCGCTACGCCCCAATGATCCGACCAGCAAAACTCGATGTACTT

CCGAGGAACTGATGTGCATAATGCATCAGGCTGGTACATTAGATCCCCGC

TTACCGCGGGCAATATAGCAACACTAAAAACTCGATGTACTTCCGAGGAA

GCGCAGTGCATAATGCTGCGCAGTGTTGCCACATAACCACTATATTAACC

ATTTATCTAGCGGACGCCAAAAACTCAATGTATTTCTGAGGAAGCGTGGT

GCATAATGCCACGCAGCGTCTGCATAACTTTTATTATTTCTTTTATTAAT

CAAATAAATTTTGTTTTTAACATTTCAAAAAAAAGTAGGTGTCATTCTA

TTCTGGGGGGTGGGGTGGGGGTTTAAAC
``` thus is engineered into the SIN plasmid construct. This new sequence is substituted for the existing 3'-end, synthetic polyA-tract, ribozyme, and BHGpolyA site of plasmid pSINCP (see, WO 01/81690) as follows. Plasmid pSINCP-bgal (pSINCP expressing bgal) is deleted of the aforementioned elements by PCR with the following primers:

NFSfWd:
(SEQ ID NO: 57)
5'ACAGACAGACCGCGGCCGCACAGACAGACGTITAAACGTGGGCGAAGA

ACTCCAGCATGAGATCC which contains a NotI site (12-19 nts.), a PmeI site (30-37 nt), and 38-65 nts that are complementary to SINCP-bgal sequences downstream of the aforementioned elements, a NotI site precedes them.

NPSrev:           (SEQ ID NO: 58)
5'-TTCGCCAGGCTCAAGGCGCGCATGCCCGAC which is complementary to the plasmid backbone region containing the SphI site. The amplified 492 bp fragment is purified from agarose gel using QIAquick gel extraction kit, digested with NotI and SphI and ligated to SINCP-bgal that has also been digested with NotI and SphI to remove the existing sequence (1106 bp). Clones containing the newly generated fragment are verified by sequencing and the intermediate construct is called SINCPt-bgal. The new 3' end is then generated using overlapping oligonucleotides:

SINpA1F
(SEQ ID NO: 59)
5'-tcgacccgggcggocgccgctacgccccaatgatccgaccagcaaaa ctcgatgtacttccgaggaactg-3'

SINpA1R
(SEQ ID NO: 60)
5'-ggtcggatcattggggcgtagcggcggccgcccgggtcga-3'

SINpA2F
(SEQ ID NO: 61)
5'-atgtgcataatgcatcaggctggtacattagatcccccgcttaccgcg ggcaatatagcaacactaaaaac-3'

SINpA2R
(SEQ ID NO: 62)
5'-agcggggatctaatgtaccagcctgatgcattatgcacatcagttcc tcggaagtacatcgagttttgct-3

SINpA3F
(SEQ ID NO: 63)
5'-tcgatgtacttccgaggaagcgoagtgcataatgctgcgcagtgttg ccacataaccactatattaacca-3'

SINpA3R
(SEQ ID NO: 64)
5'-gcgcagcattatgcactgcgcttcctcggaagtacatcgagttttta gtgttgctatattgcccgcggta-3'

SINpA4F
(SEQ ID NO: 65)
5'-tttatctagcggacgccaaaaactcaatgtatttctgaggaagcgtg gtgcataatgccacgcagcgtct-3'

SINpA4R
(SEQ ID NO: 66)
5'-cctcagaaatacattgagttttggcgtccgctagataaatggttaa tatagtggtatgtggcaacact-3'

SINpA5F
(SEQ ID NO: 67)
5'-gcataacttttattatttcttttattaatcaaataaatttgtttttt aacatttcaaaaaaaagtaggtg-3'

SINpA5R
(SEQ ID NO: 68)
5'-aacaaaatttatttgattaataaaagaaataataaaagttatgcaga cgctgcgtggcattatgcaccacgctt-3'

SINpA6F
(SEQ ID NO: 69)
5'-tcattctattctgggggtggggtggggtttaaacatcatgatc g-3'

SINpA6R
(SEQ ID NO: 70)
5'-cgatcatgatgtttaaacccccaccccaccccccagaatagaatgac acctacttttttttgaaatgttaaa-3'

The oligonucleotides are mixed, phosphorylated, denatured, slowly annealed, and ligated. After inactivating the ligase, the DNA is digested with the enzymes NotI and PmeI, gel purified using the QIAquick gel extraction kit and ligated to SINCPt-bgal digested with the same enzymes and treated with alkaline phosphatase. Clones containing the newly generated fragment are verified by sequencing and the final construct is called SINCP-pA-bgal.

To produce replicon particles this plasmid is transfected into a SIN packaging cell line that contains structural protein expression cassettes, which do not have similarly modified 3'-end sequences (Polo et al. (1999) *Proc. Natl. Acad. Sci. USA*, 96:4598-4603). After appropriate incubation, the replicon particles are harvested and purified as describe above.

Alphavirus particles are also produced in which the 3'-ends (e.g. 3' sequence required for nonstructural protein-mediated amplification, 3' CSE) of structural protein expression cassettes (e.g., defective helpers) and reporter gene cassettes (Olivo et al. (1994) *Virology* 198:381-384) are modified to incorporate a polyadenylation signal. The efficiency of RNA transport from the nucleus for alphavirus DNA molecules modified in this way is typically increased.

Example 8

Alphavirus Replicons with Modified Nonstructural Protein Genes

A Sindbis virus-based replicon (SINCR, Gardner et al., ibid) was modified within a conserved region of nsP4, encompassing SIN amino acids 363 to 404. For instance, amino acid 390 was modified by substituting (replacing) the wild-type leucine residue. The wild-type leucine residue was substituted with a basic amino acid (e.g., lysine); an acidic amino acid (e.g., glutamic acid); or an aromatic amino acid (e.g. phenylalanine).

To make these substitutions, a fragment of the replicon from plasmid pSINCR-GFP was subcloned into plasmid pCMVKm2 (zur Megede (2000) *J. Virol.* 74:2628-2635) for in vitro mutagenesis, by digestion of pSINCR-GFP with XhoI and HpaI, gel purification of the small 725 by fragment, and ligation into pCMVKm2 that had also been digested with XhoI and HpaI, resulting in the construct pCMVKm2XhoI/HpaI. Mutagenesis was performed using the Stratagene (La Jolla, Calif.) QuikChange XL site directed mutagenesis kit, according to the manufacturer's instructions, and the following pairs of oligonucleotide primers (mutation site indicated with parenthesis).

For LEU => PHE substitution:
Oligo A1:
CCGGTCTGATGATC(TTC)GAGGACCTGGGTG        (SEQ ID NO: 71)

Oligo A2:
CACCCAGGTCCTC(GAA)GATCATCAGACCGG        (SEQ ID NO: 72)

For LEU => LYS substitution:
Oligo B1:
CCGGTCTGATGATC(AAG)GAGGACCTGGGTG        (SEQ ID NO: 73)

Oligo B2:
CACCCAGGTCCTC(CTT)GATCATCAGACCGG        (SEQ ID NO: 74)

For LEU => GLU substitution:
Oligo C1:
CCGGTCTGATGATC(GAG)GAGGACCTGGGTG        (SEQ ID NO: 75)

Oligo C2:
CACCCAGGTCCTC(CTC)GATCATCAGACCGG        (SEQ ID NO: 76)

Following PCR amplification, the PCR reaction mixture was digested with DpnI and transformed into DH5α cells, according to the manufacturer's instructions. A positive clone for each of the three mutations was then used to subclone the modified nsP4 sequence back into the pSINCR-GFP replicon, again using the XhoI and HpaI sites, to generate the following alphavirus replicons with modified nsP4 genes: pSINCR390F-GFP, pSINCR390K-GFP and pSINCR390E-GFP.

RNA replicons transcribed in vitro from these plasmids are introduced into cells containing one or more structural protein-encoding defective RNA helper cells and the frequency of recombination with the non-modified parental SINCR-GFP replicon is measured by enumeration of PFU in the culture supernatant by plaque assay (either directly or after one or more serial passages in cells). The modified sequences reduce or eliminate recombination (inter-strand transfer).

Additional sequence modifications that result in the same intended phenotype may be readily obtained by one of skill in the art using random or site-directed mutagenesis in this or other (e.g., conserved) regions of nsP4 and analysis based on the teachings provided herein. For example, any of the alphavirus nsP4 amino acids corresponding to SIN nsP4 amino acids 363 to 404 may be modified singly or in combination (e.g., nsP4 391/392 E/D changed to nsP4 391/392 F/A), by using the above detailed protocol with substitution of any desired oligonucleotides for mutagenesis.

Recitation of ranges of values herein are merely intended to serve as a shorthand method of referring individually to each separate value falling within the range, unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An alphavirus replicon RNA, comprising:
   (1) a 5' alphaviral nucleotide sequence required for nonstructural protein-mediated amplification,
   (2) one or more alphaviral nucleotide sequence(s) encoding nonstructural proteins nsP1, nsP2, nsP3, and nsP4,
   (3) an alphaviral nucleotide subgenomic promoter sequence,
   (4) one or more heterologous protein-encoding nucleotide sequence(s), and
   (5) a 3' alphaviral nucleotide sequence required for nonstructural protein-mediated amplification,
   wherein the one or more alphaviral nucleotide sequence(s) encoding the nonstructural proteins is derived from a alphavirus,
   wherein the alphaviral nucleotide sequence(s) exhibit sequence identity to at least one third but no more than two-thirds of a genome of an alphavisus, and wherein the alphavirus replicon RNA further comprises a modification in a nonstructural protein selected from the group consisting of:
   (a) deletion of amino acid residues 101-120 of the nsP1 protein,
   (b) deletion of amino acid residues 450-470 of the nsP1 protein,
   (c) deletion of amino acid residues 460-480 of the nsP1 protein,
   (d) deletion of amino acid residues 470-490 of the nsP1 protein,
   (e) deletion of amino acid residues 480-500 of the nsP1 protein,
   (f) deletion of amino acid residues 9-29 of the nsP2 protein,
   (g) deletion of amino acid residues 613-633 of the nsP2 protein
   (h) deletion of amino acid residues 650-670 of the nsP2 protein,
   (i) deletion of amino acid residues 740-760 of the nsP2 protein,
   (j) deletion of amino acid residues 8-28 of the nsP4 protein, and
   (k) deletion of amino acid residues 552-570 of the nsP4 protein,
   wherein the amino acid residues are numbered relative to wild-type Venezuelan Equine Encephalitis (VEE) virus encoded by SEQ ID NO:140.

2. The alphavirus replicon RNA of claim 1, wherein the alphavirus is a Venezuelan Equine Encephalitis (VEE) virus.

3. The alphavirus replicon RNA of claim 1 wherein at least one of the heterologous protein-encoding nucleotide sequences encodes an immunogen.

4. A eukaryotic layered vector initiation system, comprising a eukaryotic promoter and the alphaviral replicon RNA of claim 1, wherein the eukaryotic promoter initiates initiates 5' to 3' synthesis of the alphaviral replicon RNA.

5. The eukaryotic layered vector initiation system of claim 4, wherein the alphavirus is a Venezuelan Equine Encephalitis (VEE) virus.

6. The eukaryotic layered vector initiation system of claim 4, wherein at least one heterologous gene encodes an immunogen.

7. A method of generating an immune response in a mammal, comprising administering an effective amount of the eukaryotic layered vector initiation system of claim 6 to the mammal.

8. A chimeric alphavirus particle, comprising:
   (1) a capsid protein,
   (2) an E1 envelope glycoprotein,
   (3) an E2 envelope glycoprotein, and
   (4) the alphavirus replicon RNA of claim 1.

9. The alphavirus replicon RNA of claim 1, wherein the alphavirus replicon RNA comprises a deletion in a nonstructural protein selected from the group consisting of:
   (a) amino acid residues 101-120 of the nsP1 protein,
   (b) amino acid residues 450-470 of the nsP1 protein,
   (c) amino acid residues 460-480 of the nsP1 protein,
   (d) amino acid residues 470-490 of the nsP1 protein, and
   (e) amino acid residues 480-500 of the nsP1 protein.

10. The alphavirus replicon RNA of claim 1, wherein the alphavirus replicon RNA comprises a deletion in a nonstructural protein selected from the group consisting of:
    (a) amino acid residues 9-29 of the nsP2 protein,
    (b) amino acid residues 613-633 of the nsP2 protein,
    (c) amino acid residues 650-670 of the nsP2 protein, and
    (d) amino acid residues 740-760 of the nsP2 protein.

11. The alphavirus replicon RNA of claim 1, wherein the alphavirus replicon RNA comprises a modification in a nonstructural protein selected from the group consisting of:
    (a) deletion of amino acid residues 8-28 of the nsP4 protein, and
    (b) deletion of amino acid residues 552-570 of the nsP4 protein.

12. An alphavirus replicon RNA, comprising:
    (1) a 5' alphaviral nucleotide sequence required for nonstructural protein-mediated amplification,
    (2) an alphaviral nucleotide sequence encoding nonstructural proteins nsP1, nsP2, nsP3, and nsP4,
    (3) an alphaviral nucleotide subgenomic promoter sequence,
    (4) one or more heterologous protein-encoding nucleotide sequences, and
    (5) a 3' alphaviral nucleotide sequence required for nonstructural protein-mediated amplification,
    wherein the alphaviral nucleotide sequence encoding the nonstructural proteins is derived from an alphavirus,
    wherein the alphaviral nucleotide sequences exhibit sequence identity to at least one third but no more than two-thirds of a genome of an alphavirus, and
    wherein the alphavirus replicon RNA further composes a modification in a nonstructural protein selected from the group consisting of:
    (a) deletion of amino acid residues 350-380 of the nsP3 protein,
    (b) deletion of amino acid residues 360-390 of the nsP3 protein,
    (c) deletion of amino acid residues 370-400 of the nsP3 protein,
    (d) deletion of amino acid residues 380-410 of the nsP3 protein,
    (e) deletion of amino acid residues 390-420 of the nsP3 protein,
    (f) deletion of amino acid residues 400-430 of the nsP3 protein,
    (g) deletion of amino acid residues 410-440 of the nsP3 protein,
    (h) deletion of amino acid residues 420-450 of the nsP3 protein,
    (i) deletion of amino acid residues 430-460 of the nsP3 protein,
    (j) deletion of amino acid residues 440-470 of the nsP3 protein,
    (k) deletion of amino acid residues 450-480 of the nsP3 protein,
    (l) deletion of amino acid residues 460-490 of the nsP3 protein, (m) deletion of amino acid residues 470-500 of the nsP3 protein, (n) deletion of amino acid residues 480-510 of the nsP3 protein, (o) deletion of amino acid residues 500-530 of the nsP3 protein, and (p) a deletion of at least 30 contiguous amino acids from the non-conserved region between amino acid residues 340-530 of nsP3 of an alphavirus other than VEE or Semliki forest virus (SFV), wherein the amino acid residues are numbered relative to wild-type VEE virus encoded by SEQ ID NO:140, and wherein the amino acid positions are aligned according to the full length nsP1-4 precursor polypeptide.

13. The alphavirus replicon RNA of claim 12, wherein the alphavirus is a Venezuelan Equine Encephalitis (VEE) virus.

14. The alphavirus replicon RNA of claim 12, wherein at least one of the heterologous protein-encoding nucleotide sequences encodes an immunogen.

15. A eukaryotic layered vector initiation system, comprising a eukaryotic promoter and the alphaviral replicon RNA of claim 1, wherein the eukaryotic promoter initiates 5' to 3' synthesis of the alphaviral replicon RNA.

16. The eukaryotic layered vector initiation system of claim 15, wherein the alphavirus is a Venezuelan Equine Encephalitis (VEE) virus.

17. The eukaryotic layered vector initiation system of claim 15, wherein at least one heterologous gene encodes an immunogen.

18. A method of generating an immune response in a mammal, comprising administering an effective amount of the eukaryotic layered vector initiation system of claim 15 to the mammal.

19. A chimeric alphavirus particle, comprising:
(1) a capsid protein,
(2) an E1 envelope glycoprotein,
(3) an E2 envelope glycoprotein, and
(4) the alphavirus replicon RNA of claim 1.

20. An alphavirus replicon RNA, comprising:
(1) a 5' alphaviral nucleotide sequence required for non-structural protein-mediated amplification;
(2) an alphaviral nucleotide sequence encoding nonstructural proteins nsP1, nsP2, nsP3, and nsP4 from Venezuelan Equine Encephalitis (VEE) virus, wherein the nucleotide sequence encoding amino acid residues 490-520 of the nsP3 protein is replaced in-frame by a packaging sequence from another alphavirus, and wherein the amino acid residues are numbered relative to wild-type VEE virus encoded by SEQ ID NO:140;
(3) an alphaviral nucleotide subgenomic promoter sequence;
(4) one or more heterologous protein-encoding nucleotide sequences; and
(5) a 3' alphaviral nucleotide sequence required for non-structural protein-mediated amplification; and
wherein the alphaviral nucleotide sequences exhibit sequence identity to at least one third but no more than two-thirds of a genome of a alphavirus.

* * * * *

SEQUENCE LISTING

```
<160> NUMBER OF SEQ ID NOS: 140

<210> SEQ ID NO 1
<211> LENGTH: 39
<212> TYPE: DNA
<213> ORGANISM: Artificial Sequence
<220> FEATURE:
<223> OTHER INFORMATION: VEE 5' primer

<400> SEQUENCE: 1
aagcagagct cgtttagtga accgtatggg cggcgcatg                     39

<210> SEQ ID NO 2
<211> LENGTH: 41
<212> TYPE: DNA
<213> ORGANISM: Artificial Sequence
<220> FEATURE:
<223> OTHER INFORMATION: VEE 3' primer

<400> SEQUENCE: 2
gccctgcgtc cagctcatct cgatctgtcc ggatcttccg c                  41
```

<210> SEQ ID NO 3
<211> LENGTH: 80
<212> TYPE: DNA
<213> ORGANISM: Artificial Sequence
<220> FEATURE:
<223> OTHER INFORMATION: Synthetically generated oligonucleotide

<400> SEQUENCE: 3
cacgcgtact actgttaact catcaagatc tactaggcct aaggcaccac ctgcaggtag        60
tagatacaca tcataatacc                                                    80

<210> SEQ ID NO 4
<211> LENGTH: 78
<212> TYPE: DNA
<213> ORGANISM: Artificial Sequence
<220> FEATURE:
<223> OTHER INFORMATION: Synthetically generated oligonucleotide

<400> SEQUENCE: 4
tagggcggcg atttaaatga tttagactac gtcagcagcc ctcagcggcg cgcccaccca        60
gcggccgcag gatagttt                                                      78

<210> SEQ ID NO 5
<211> LENGTH: 79
<212> TYPE: DNA
<213> ORGANISM: Artificial Sequence
<220> FEATURE:
<223> OTHER INFORMATION: Synthetically generated oligonucleotide

<400> SEQUENCE: 5
tatgatgtgt atctactacc tgcaggtggt gccttaggcc tagtagatct tgatgagtta        60
acagtagtac gcgtgggcc                                                     79

<210> SEQ ID NO 6
<211> LENGTH: 83
<212> TYPE: DNA
<213> ORGANISM: Artificial Sequence
<220> FEATURE:
<223> OTHER INFORMATION: Synthetically generated oligonucleotide

<400> SEQUENCE: 6
aaactatcct gcggccgctg ggtgggcgcg ccgctgaggg ctgctgacgt agtctaaatc        60
atttaaatcg ccgccctagg tat                                                83

<210> SEQ ID NO 7
<211> LENGTH: 58
<212> TYPE: DNA
<213> ORGANISM: Artificial Sequence
<220> FEATURE:
<223> OTHER INFORMATION: Synthetically generated oligonucleotide

<400> SEQUENCE: 7
ggccgcatac agcagcaatt ggcaagctgc ttacatagaa ctcgcggcga ttggcatg         58

<210> SEQ ID NO 8
<211> LENGTH: 50
<212> TYPE: DNA
<213> ORGANISM: Artificial Sequence
<220> FEATURE:
<223> OTHER INFORMATION: Synthetically generated oligonucleotide

<400> SEQUENCE: 8

```
ccaatcgccg cgagttctat gtaagcagct tgccaattgc tgctgtatgc        50
```

<210> SEQ ID NO 9
<211> LENGTH: 61
<212> TYPE: DNA
<213> ORGANISM: Artificial Sequence
<220> FEATURE:
<223> OTHER INFORMATION: Synthetically generated oligonucleotide

<400> SEQUENCE: 9

```
ccgccttaaa attttatttt tatttttttct tttcttttcc gaatcggatt ttgttttaa    60
t                                                                   61
```

<210> SEQ ID NO 10
<211> LENGTH: 65
<212> TYPE: DNA
<213> ORGANISM: Artificial Sequence
<220> FEATURE:
<223> OTHER INFORMATION: Synthetically generated oligonucleotide

<400> SEQUENCE: 10

```
attaaaaaca aatccgatt cggaaaagaa agaaaaaat aaaataaaaa ttttaaggcg     60
gcatg                                                               65
```

<210> SEQ ID NO 11
<211> LENGTH: 75
<212> TYPE: DNA
<213> ORGANISM: Artificial Sequence
<220> FEATURE:
<223> OTHER INFORMATION: Synthetically generated oligonucleotide

<400> SEQUENCE: 11

```
atttcaaaaa aaaaaaaaaa aaaaaaaaaa aaaaaaaaaa aaaaagggtc ggcatggcat   60
ctccacctcc tcgcg                                                    75
```

<210> SEQ ID NO 12
<211> LENGTH: 78
<212> TYPE: DNA
<213> ORGANISM: Artificial Sequence
<220> FEATURE:
<223> OTHER INFORMATION: Synthetically generated oligonucleotide

<400> SEQUENCE: 12

```
gaccgcgagg aggtggagat gccatgccga ccctttttttt tttttttttt tttttttttt   60
tttttttttt tttgaaat                                                 78
```

<210> SEQ ID NO 13
<211> LENGTH: 64
<212> TYPE: DNA
<213> ORGANISM: Artificial Sequence
<220> FEATURE:
<223> OTHER INFORMATION: Synthetically generated oligonucleotide

<400> SEQUENCE: 13

```
gtccgacctg gcatccgaa ggaggacgca cgtccactcg gatggctaag ggagagccac    60
gttt                                                                64
```

<210> SEQ ID NO 14
<211> LENGTH: 61
<212> TYPE: DNA
<213> ORGANISM: Artificial Sequence
<220> FEATURE:
<223> OTHER INFORMATION: Synthetically generated oligonucleotide

<400> SEQUENCE: 14
aaacgtggct ctcccttagc catccgagtg gacgtgcgtc ctccttcgga tgcccaggtc      60
g                                                                      61

<210> SEQ ID NO 15
<211> LENGTH: 43
<212> TYPE: DNA
<213> ORGANISM: Artificial Sequence
<220> FEATURE:
<223> OTHER INFORMATION: Primer

<400> SEQUENCE: 15
atatatatct cgagcctcag catgtcacta gtgaccacca tgt                        43

<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16
atatataaat tccatggtga tggagtcc                                         28

<210> SEQ ID NO 17
<211> LENGTH: 39
<212> TYPE: DNA
<213> ORGANISM: Artificial Sequence
<220> FEATURE:
<223> OTHER INFORMATION: Synthetically generated oligonucleotide

<400> SEQUENCE: 17
atatatatgc ggccgcttac cattgctcgc agttctccg                             39

<210> SEQ ID NO 18
<211> LENGTH: 44
<212> TYPE: DNA
<213> ORGANISM: Artificial Sequence
<220> FEATURE:
<223> OTHER INFORMATION: Synthetically generated oligonucleotide

<400> SEQUENCE: 18
gagatgtcat cgggcacgca tgtgtggtcg gagggaagtt attc                       44

<210> SEQ ID NO 19
<211> LENGTH: 41
<212> TYPE: DNA
<213> ORGANISM: Artificial Sequence
<220> FEATURE:
<223> OTHER INFORMATION: Synthetically generated oligonucleotide

<400> SEQUENCE: 19
atatatctcg agccaccatg aatagaggat tctttaacat g                          41

<210> SEQ ID NO 20
<211> LENGTH: 31
<212> TYPE: DNA
<213> ORGANISM: Artificial Sequence
<220> FEATURE:
<223> OTHER INFORMATION: Synthetically generated oligonucleotide

<400> SEQUENCE: 20
gggaacgtct tgtcggcctc caacttaagt g                                     31

-continued

<210> SEQ ID NO 21
<211> LENGTH: 44
<212> TYPE: DNA
<213> ORGANISM: Artificial Sequence
<220> FEATURE:
<223> OTHER INFORMATION: Synthetically generated oligonucleotide

<400> SEQUENCE: 21
gaataacttc cctccgacca cacatgcgtg cccgatgaca tctc                44

<210> SEQ ID NO 22
<211> LENGTH: 34
<212> TYPE: DNA
<213> ORGANISM: Artificial Sequence
<220> FEATURE:
<223> OTHER INFORMATION: Synthetically generated oligonucleotide

<400> SEQUENCE: 22
ccacacaagc gtacccgatg acatctccgt cttc                            34

<210> SEQ ID NO 23
<211> LENGTH: 31
<212> TYPE: DNA
<213> ORGANISM: Artificial Sequence
<220> FEATURE:
<223> OTHER INFORMATION: Synthetically generated oligonucleotide

<400> SEQUENCE: 23
catgattggg aacaatctgt cggcctccaa c                               31

<210> SEQ ID NO 24
<211> LENGTH: 27
<212> TYPE: DNA
<213> ORGANISM: Artificial Sequence
<220> FEATURE:
<223> OTHER INFORMATION: Synthetically generated oligonucleotide

<400> SEQUENCE: 24
gtcagactcc aacttaagtg ccatgcg                                    27

<210> SEQ ID NO 25
<211> LENGTH: 40
<212> TYPE: DNA
<213> ORGANISM: Artificial Sequence
<220> FEATURE:
<223> OTHER INFORMATION: Synthetically generated oligonucleotide

<400> SEQUENCE: 25
gggaagataa acggctacgc tctggccatg gaaggaaagg                      40

<210> SEQ ID NO 26
<211> LENGTH: 37
<212> TYPE: DNA
<213> ORGANISM: Artificial Sequence
<220> FEATURE:
<223> OTHER INFORMATION: Synthetically generated oligonucleotide

<400> SEQUENCE: 26
atatatatgc ggccgctcac cactcttctg tcccttc                         37

<210> SEQ ID NO 27
<211> LENGTH: 31
<212> TYPE: DNA
<213> ORGANISM: Artificial Sequence
<220> FEATURE:
<223> OTHER INFORMATION: Synthetically generated oligonucleotide

<400> SEQUENCE: 27
gccgacaaga cgttcccaat catgttggaa g                           31

<210> SEQ ID NO 28
<211> LENGTH: 39
<212> TYPE: DNA
<213> ORGANISM: Artificial Sequence
<220> FEATURE:
<223> OTHER INFORMATION: Synthetically generated oligonucleotide

<400> SEQUENCE: 28
atatatatgc ggccgcttac cattgctcgc agttctccg                   39

<210> SEQ ID NO 29
<211> LENGTH: 44
<212> TYPE: DNA
<213> ORGANISM: Artificial Sequence
<220> FEATURE:
<223> OTHER INFORMATION: Synthetically generated oligonucleotide

<400> SEQUENCE: 29
gagatgtcat cgggcacgca tgtgtggtcg gagggaagtt attc             44

<210> SEQ ID NO 30
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 30
tcatcgggta cgcttgtgtg gtcg                                   24

<210> SEQ ID NO 31
<211> LENGTH: 30
<212> TYPE: DNA
<213> ORGANISM: Artificial Sequence
<220> FEATURE:
<223> OTHER INFORMATION: Synthetically generated oligonucleotide

<400> SEQUENCE: 31
gacagattgt tcccaatcat gttggaaggg                             30

<210> SEQ ID NO 32
<211> LENGTH: 34
<212> TYPE: DNA
<213> ORGANISM: Artificial Sequence
<220> FEATURE:
<223> OTHER INFORMATION: Synthetically generated oligonucleotide

<400> SEQUENCE: 32
acttaagttg gagtctgaca agacgttccc aatc                        34

<210> SEQ ID NO 33
<211> LENGTH: 38
<212> TYPE: DNA
<213> ORGANISM: Artificial Sequence
<220> FEATURE:
<223> OTHER INFORMATION: Synthetically generated oligonucleotide

<400> SEQUENCE: 33
atatatctcg agccaccatg ttcccgttcc agccaatg                    38

<210> SEQ ID NO 34

```
<211> LENGTH: 40
<212> TYPE: DNA
<213> ORGANISM: Artificial Sequence
<220> FEATURE:
<223> OTHER INFORMATION: Synthetically generated oligonucleotide

<400> SEQUENCE: 34
cctttccttc catggccaga gcgtagccgt ttatcttccc                           40

<210> SEQ ID NO 35
<211> LENGTH: 27
<212> TYPE: DNA
<213> ORGANISM: Artificial Sequence
<220> FEATURE:
<223> OTHER INFORMATION: Synthetically generated oligonucleotide

<400> SEQUENCE: 35
atatatcagg ggactccatc accatgg                                        27

<210> SEQ ID NO 36
<211> LENGTH: 77
<212> TYPE: DNA
<213> ORGANISM: Artificial Sequence
<220> FEATURE:
<223> OTHER INFORMATION: Synthetically generated oligonucleotide

<400> SEQUENCE: 36
gggattacgg cgtttggggc cagggcgtat ggcgtcaggc actcacggcg cgctttgcaa    60
aacagccagg tagacgc                                                   77

<210> SEQ ID NO 37
<211> LENGTH: 84
<212> TYPE: DNA
<213> ORGANISM: Artificial Sequence
<220> FEATURE:
<223> OTHER INFORMATION: Primer

<400> SEQUENCE: 37
gccccaaacg ccgtaatccc aacttcgctg gcactcttgt gctgcgttag gtcggccaat    60
gctgagacca cctgggagtc cttg                                           84

<210> SEQ ID NO 38
<211> LENGTH: 50
<212> TYPE: DNA
<213> ORGANISM: Artificial Sequence
<220> FEATURE:
<223> OTHER INFORMATION: Primer

<400> SEQUENCE: 38
ccaatcgccg cgagttctat gtaagcagct tgccaattgc tgctgtatgc                50

<210> SEQ ID NO 39
<211> LENGTH: 31
<212> TYPE: DNA
<213> ORGANISM: Artificial Sequence
<220> FEATURE:
<223> OTHER INFORMATION: Synthetically generated oligonucleotide

<400> SEQUENCE: 39
gtatggcgtc aggcacgcac ggcgcgcttt g                                   31

<210> SEQ ID NO 40
<211> LENGTH: 31
<212> TYPE: DNA
<213> ORGANISM: Artificial Sequence
```

```
<220> FEATURE:
<223> OTHER INFORMATION: Synthetically generated oligonucleotide

<400> SEQUENCE: 40
agcgcgccgt gcgtgcctga cgccatacgc c                              31

<210> SEQ ID NO 41
<211> LENGTH: 35
<212> TYPE: DNA
<213> ORGANISM: Artificial Sequence
<220> FEATURE:
<223> OTHER INFORMATION: Synthetically generated oligonucleotide

<400> SEQUENCE: 41
atggcgtcag gcactcaacg cgcgctttgc aaaac                          35

<210> SEQ ID NO 42
<211> LENGTH: 35
<212> TYPE: DNA
<213> ORGANISM: Artificial Sequence
<220> FEATURE:
<223> OTHER INFORMATION: Synthetically generated oligonucleotide

<400> SEQUENCE: 42
tttgcaaagc gcgcgttgag tgcctgacgc catac                          35

<210> SEQ ID NO 43
<211> LENGTH: 35
<212> TYPE: DNA
<213> ORGANISM: Artificial Sequence
<220> FEATURE:
<223> OTHER INFORMATION: Synthetically generated oligonucleotide

<400> SEQUENCE: 43
atggcgtcag gcacgcaacg cgcgctttgc aaaac                          35

<210> SEQ ID NO 44
<211> LENGTH: 35
<212> TYPE: DNA
<213> ORGANISM: Artificial Sequence
<220> FEATURE:
<223> OTHER INFORMATION: Synthetically generated oligonucleotide

<400> SEQUENCE: 44
tttgcaaagc gcgcgttgcg tgcctgacgc catac                          35

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
gccgacagat cgttcgacgt c                                         21

<210> SEQ ID NO 46
<211> LENGTH: 40
<212> TYPE: DNA
<213> ORGANISM: Artificial Sequence
<220> FEATURE:
<223> OTHER INFORMATION: Primer

<400> SEQUENCE: 46
atatatatgg tcactagtga ccactcttct gtcccttccg                     40
```

<210> SEQ ID NO 47
<211> LENGTH: 40
<212> TYPE: DNA
<213> ORGANISM: Artificial Sequence
<220> FEATURE:
<223> OTHER INFORMATION: Primer

<400> SEQUENCE: 47
atatatatgc ggccgctcaa ttatgtttct ggttggtcag                40

<210> SEQ ID NO 48
<211> LENGTH: 38
<212> TYPE: DNA
<213> ORGANISM: Artificial Sequence
<220> FEATURE:
<223> OTHER INFORMATION: Primer

<400> SEQUENCE: 48
atatatctcg agccgccagc catgtcacta gtgaccac                  38

<210> SEQ ID NO 49
<211> LENGTH: 28
<212> TYPE: DNA
<213> ORGANISM: Artificial Sequence
<220> FEATURE:
<223> OTHER INFORMATION: Primer

<400> SEQUENCE: 49
atatctcgag agggatcacg ggagaaac                             28

<210> SEQ ID NO 50
<211> LENGTH: 28
<212> TYPE: DNA
<213> ORGANISM: Artificial Sequence
<220> FEATURE:
<223> OTHER INFORMATION: Primer

<400> SEQUENCE: 50
agaggagctc aaataccacc ggccctac                             28

<210> SEQ ID NO 51
<211> LENGTH: 705
<212> TYPE: DNA
<213> ORGANISM: Artificial Sequence
<220> FEATURE:
<223> OTHER INFORMATION: Synthetically generated oligonucleotide

<400> SEQUENCE: 51
ctagagttaa cggctcgtaa cataggccta tgcagctctg acgttatgga gcggtcacgt    60
agagggatgt ccattcttag aaagaagtat ttgaaaccat ccaacaatgt tctattctct   120
gttggctcga ccatctacca cgagaagagg gacttactga ggagctggca cctgccgtct   180
gtatttcact tacgtggcaa gcaaaattac acatgtcggt gtgagactat agttagttgc   240
gacgggtacg tcgttaaaag aatagctatc agtccaggcc tgtatgggaa gccttcaggc   300
tatgctgcta cgatgcaccg cgagggattc ttgtgctgca aagtgacaga cacattgaac   360
ggggagaggg tctctttttcc cgtgtgcacg tatgtgccag ctacattgtg tgaccaaatg   420
actggcatac tggcaacaga tgtcagtgcg gacgacgcgc aaaaactgct ggttgggctc   480
aaccagcgta tagtcgtcaa cggtcgcacc cagagaaaca ccaataccat gaaaaattac   540
cttttgcccg tagtggccca ggcatttgct aggtgggcaa aggaatataa ggaagatcaa   600
gaagatgaaa ggccactagg actacgagat agacagttag tcatggggtg ttgttgggct   660
tttagaaggc acaagataac atctatttat aagcgcccgg ataca          705

<210> SEQ ID NO 52
<211> LENGTH: 705
<212> TYPE: DNA
<213> ORGANISM: Artificial Sequence
<220> FEATURE:
<223> OTHER INFORMATION: Synthetically generated oligonucleotide

<400> SEQUENCE: 52
tcaattgccg agcattgtat ccggatacgt cgagactgca atacctcgcc agtgcatctc   60
cctacaggta agaatctttc ttcataaact ttggtaggtt gttacaagat aagagacaac  120
cgagctggta gatggtgctc ttctccctga atgactcctc gaccgtggac ggcagacata  180
aagtgaatgc accgttcgtt ttaatgtgta cagccacact ctgatatcaa tcaacgctgc  240
ccatgcagca atttcttat cgatagtcag gtccggacat acccttcgga agtccgatac  300
gacgatgcta cgtggcgctc cctaagaaca cgacgtttca ctgtctgtgt aacttgcccc  360
tctcccagag aaaagggcac acgtgcatac acggtcgatg taacacactg gtttactgac  420
cgtatgaccg ttgtctacag tcacgcctgc tgcgcgtttt tgacgaccaa cccgagttgg  480
tcgcatatca gcagttgcca gcgtgggtct ctttgtggtt atggtacttt ttaatggaaa  540
acgggcatca ccgggtccgt aaacgatcca cccgtttcct tatattcctt ctagttcttc  600
tactttccgg tgatcctgat gctctatctg tcaatcagta ccccacaaca acccgaaaat  660
cttccgtgtt ctattgtaga taaatattcg cgggcctatg tgcgc                  705

<210> SEQ ID NO 53
<211> LENGTH: 26
<212> TYPE: DNA
<213> ORGANISM: Artificial sequence
<220> FEATURE:
<223> OTHER INFORMATION: VEE subgenomic 5' NTR sequence

<400> SEQUENCE: 53
actacgacat agtctagtcc gccaag                                        26

<210> SEQ ID NO 54
<211> LENGTH: 40
<212> TYPE: DNA
<213> ORGANISM: Artificial sequence
<220> FEATURE:
<223> OTHER INFORMATION: Synthetically generated oligonucleotide S/Vc
Vg1R

<400> SEQUENCE: 54
atatatatgg tcactagtga ccattgctcg cagttctccg 40

<210> SEQ ID NO 55
<211> LENGTH: 21
<212> TYPE: DNA
<213> ORGANISM: Artificial sequence
<220> FEATURE:
<223> OTHER INFORMATION: Synthetically generated oligonucleotide
ScAatIIF

<400> SEQUENCE: 55
gccgacagat cgttcgacgt c 21

<210> SEQ ID NO 56
<211> LENGTH: 378
<212> TYPE: DNA

<213> ORGANISM: Artificial sequence
<220> FEATURE:
<223> OTHER INFORMATION: Synthetic construct

<400> SEQUENCE: 56

```
gcggccgccg ctacgcccca atgatccgac cagcaaaact cgatgtactt ccgaggaact    60
gatgtgcata atgcatcagg ctggtacatt agatccccgc ttaccgcggg caatatagca   120
acactaaaaa ctcgatgtac ttccgaggaa gcgcagtgca taatgctgcg cagtgttgcc   180
acataaccac tatattaacc atttatctag cggacgccaa aaactcaatg tatttctgag   240
gaagcgtggt gcataatgcc acgcagcgtc tgcataactt ttattatttc ttttattaat   300
caaataaatt ttgtttttaa catttcaaaa aaaagtagg tgtcattcta ttctgggggg    360
tggggtgggg gtttaaac                                                 378
```

<210> SEQ ID NO 57
<211> LENGTH: 65
<212> TYPE: DNA
<213> ORGANISM: Artificial sequence
<220> FEATURE:
<223> OTHER INFORMATION: Primer

<400> SEQUENCE: 57

```
acagacagac cgcggccgca cagacagacg tttaaacgtg ggcgaagaac tccagcatga    60
gatcc                                                               65
```

<210> SEQ ID NO 58
<211> LENGTH: 30
<212> TYPE: DNA
<213> ORGANISM: Artificial sequence
<220> FEATURE:
<223> OTHER INFORMATION: Primer

<400> SEQUENCE: 58

```
ttcgccaggc tcaaggcgcg catgcccgac                                     30
```

<210> SEQ ID NO 59
<211> LENGTH: 70
<212> TYPE: DNA
<213> ORGANISM: Artificial sequence
<220> FEATURE:
<223> OTHER INFORMATION: Synthetically generated oligonucleotide

<400> SEQUENCE: 59

```
tcgacccggg cggccgccgc tacgccccaa tgatccgacc agcaaaactc gatgtacttc    60
cgaggaactg                                                          70
```

<210> SEQ ID NO 60
<211> LENGTH: 40
<212> TYPE: DNA
<213> ORGANISM: Artificial sequence
<220> FEATURE:
<223> OTHER INFORMATION: Synthetically generated oligonucleotide

<400> SEQUENCE: 60

```
ggtcggatca ttggggcgta gcggcggccg cccgggtcga                          40
```

<210> SEQ ID NO 61
<211> LENGTH: 70
<212> TYPE: DNA
<213> ORGANISM: Artificial sequence
<220> FEATURE:
<223> OTHER INFORMATION: Synthetically generated oligonucleotide
```

<400> SEQUENCE: 61
atgtgcataa tgcatcaggc tggtacatta gatccccgct taccgcgggc aatatagcaa    60
cactaaaaac                                                           70

<210> SEQ ID NO 62
<211> LENGTH: 70
<212> TYPE: DNA
<213> ORGANISM: Artificial sequence
<220> FEATURE:
<223> OTHER INFORMATION: Synthetically generated oligonucleotide

<400> SEQUENCE: 62
agcggggatc taatgtacca gcctgatgca ttatgcacat cagttcctcg gaagtacatc    60
gagttttgct                                                           70

<210> SEQ ID NO 63
<211> LENGTH: 70
<212> TYPE: DNA
<213> ORGANISM: Artificial sequence
<220> FEATURE:
<223> OTHER INFORMATION: Synthetically generated oligonucleotide

<400> SEQUENCE: 63
tcgatgtact tccgaggaag cgcagtgcat aatgctgcgc agtgttgcca cataaccact    60
atattaacca                                                           70

<210> SEQ ID NO 64
<211> LENGTH: 70
<212> TYPE: DNA
<213> ORGANISM: Artificial sequence
<220> FEATURE:
<223> OTHER INFORMATION: Synthetically generated oligonucleotide

<400> SEQUENCE: 64
gcgcagcatt atgcactgcg cttcctcgga agtacatcga gttttagtg ttgctatatt     60 gcccgcggta                                                           70

<210> SEQ ID NO 65
<211> LENGTH: 70
<212> TYPE: DNA
<213> ORGANISM: Artificial sequence
<220> FEATURE:
<223> OTHER INFORMATION: Synthetically generated oligonucleotide

<400> SEQUENCE: 65
tttatctagc ggacgccaaa aactcaatgt atttctgagg aagcgtggtg cataatgcca    60
cgcagcgtct                                                           70

<210> SEQ ID NO 66
<211> LENGTH: 70
<212> TYPE: DNA
<213> ORGANISM: Artificial sequence
<220> FEATURE:
<223> OTHER INFORMATION: Synthetically generated oligonucleotide

<400> SEQUENCE: 66
cctcagaaat acattgagtt tttggcgtcc gctagataaa tggttaatat agtggttatg    60
tggcaacact                                                           70

<210> SEQ ID NO 67

```
<211> LENGTH: 71
<212> TYPE: DNA
<213> ORGANISM: Artificial sequence
<220> FEATURE:
<223> OTHER INFORMATION: Synthetically generated oligonucleotide

<400> SEQUENCE: 67
gcataacttt tattatttct tttattaatc aaataaattt tgttttttaac atttcaaaaa    60 aaaagtaggt g                                                          71

<210> SEQ ID NO 68
<211> LENGTH: 74
<212> TYPE: DNA
<213> ORGANISM: Artificial sequence
<220> FEATURE:
<223> OTHER INFORMATION: Synthetically generated oligonucleotide

<400> SEQUENCE: 68
aacaaaattt atttgattaa taaagaaat aataaaagtt atgcagacgc tgcgtggcat      60
tatgcaccac gctt                                                       74

<210> SEQ ID NO 69
<211> LENGTH: 46
<212> TYPE: DNA
<213> ORGANISM: Artificial sequence
<220> FEATURE:
<223> OTHER INFORMATION: Synthetically generated oligonucleotide

<400> SEQUENCE: 69
tcattctatt ctgggggtg gggtgggggt ttaaacatca tgatcg                     46

<210> SEQ ID NO 70
<211> LENGTH: 73
<212> TYPE: DNA
<213> ORGANISM: Artificial sequence
<220> FEATURE:
<223> OTHER INFORMATION: Synthetically generated oligonucleotide

<400> SEQUENCE: 70
cgatcatgat gtttaaaccc ccaccccacc ccccagaata gaatgacacc tactttttt      60 ttgaaatgtt aaa                                                        73

<210> SEQ ID NO 71
<211> LENGTH: 30
<212> TYPE: DNA
<213> ORGANISM: Artificial sequence
<220> FEATURE:
<223> OTHER INFORMATION: Primer

<400> SEQUENCE: 71
ccggtctgat gatcttcgag gacctgggtg                                      30

<210> SEQ ID NO 72
<211> LENGTH: 30
<212> TYPE: DNA
<213> ORGANISM: Artificial sequence
<220> FEATURE:
<223> OTHER INFORMATION: Primer

<400> SEQUENCE: 72
cacccaggtc ctcgaagatc atcagaccgg                                      30

<210> SEQ ID NO 73
<211> LENGTH: 30
```

```
<212> TYPE: DNA
<213> ORGANISM: Artificial sequence
<220> FEATURE:
<223> OTHER INFORMATION: Primer

<400> SEQUENCE: 73
ccggtctgat gatcaaggag gacctgggtg                                       30

<210> SEQ ID NO 74
<211> LENGTH: 30
<212> TYPE: DNA
<213> ORGANISM: Artificial sequence
<220> FEATURE:
<223> OTHER INFORMATION: Primer

<400> SEQUENCE: 74
cacccaggtc ctccttgatc atcagaccgg                                       30

<210> SEQ ID NO 75
<211> LENGTH: 30
<212> TYPE: DNA
<213> ORGANISM: Artificial sequence
<220> FEATURE:
<223> OTHER INFORMATION: Primer

<400> SEQUENCE: 75
ccggtctgat gatcgaggag gacctgggtg                                       30

<210> SEQ ID NO 76
<211> LENGTH: 30
<212> TYPE: DNA
<213> ORGANISM: Artificial sequence
<220> FEATURE:
<223> OTHER INFORMATION: Primer

<400> SEQUENCE: 76
cacccaggtc ctcctcgatc atcagaccgg                                       30

<210> SEQ ID NO 77
<211> LENGTH: 38
<212> TYPE: DNA
<213> ORGANISM: Artificial sequence
<220> FEATURE:
<223> OTHER INFORMATION: Primer

<400> SEQUENCE: 77
ggccgctttt cttttccgaa tcggattttg tttttaat                              38

<210> SEQ ID NO 78
<211> LENGTH: 34
<212> TYPE: DNA
<213> ORGANISM: Artificial sequence
<220> FEATURE:
<223> OTHER INFORMATION: Primer

<400> SEQUENCE: 78
attaaaaaca aaatccgatt cggaaaagaa aagc                                  34

<210> SEQ ID NO 79
<211> LENGTH: 45
<212> TYPE: PRT
<213> ORGANISM: Sindbis virus"

<400> SEQUENCE: 79

Lys Gln Gly Asp Pro Val Leu Glu Thr Asp Ile Ala Ser Phe Asp Lys
1               5                   10                  15
```

Ser Gln Asp Asp Ser Met Ala Leu Thr Gly Leu Met Ile Leu Glu Asp
            20                  25                  30

Leu Gly Val Asp Gln Pro Leu Leu Asp Leu Ile Glu Cys
        35                  40                  45

<210> SEQ ID NO 80
<211> LENGTH: 45
<212> TYPE: PRT
<213> ORGANISM: Venezuelan equine encephalitis virus

<400> SEQUENCE: 80

Gln Pro Gly Asp Cys Val Leu Glu Thr Asp Ile Ala Ser Phe Asp Lys
1               5                   10                  15

Ser Glu Asp Asp Ser Met Ala Leu Thr Ala Leu Met Ile Leu Glu Asp
            20                  25                  30

Leu Gly Val Asp Ala Glu Leu Leu Thr Leu Ile Glu Ala
        35                  40                  45

<210> SEQ ID NO 81
<211> LENGTH: 45
<212> TYPE: PRT
<213> ORGANISM: Semliki Forest virus

<400> SEQUENCE: 81

His Pro Gly Asp Pro Val Leu Glu Thr Asp Ile Ala Ser Phe Asp Lys
1               5                   10                  15

Ser Gln Asp Asp Ser Leu Ala Leu Thr Ala Leu Met Ile Leu Glu Asp
            20                  25                  30

Leu Gly Val Asp Gln Tyr Leu Leu Asp Leu Ile Glu Ala
        35                  40                  45

<210> SEQ ID NO 82
<211> LENGTH: 45
<212> TYPE: PRT
<213> ORGANISM: Plant virus

<400> SEQUENCE: 82

Leu Asn Asn Arg Tyr Phe Leu Glu Ala Asp Leu Ser Lys Phe Asp Lys
1               5                   10                  15

Ser Gln Gly Glu Leu His Leu Gly Phe Gln Arg Glu Ile Leu Leu Ala
            20                  25                  30

Leu Gly Phe Pro Ala Pro Leu Thr Asn Trp Trp Ser Asp
        35                  40                  45

<210> SEQ ID NO 83
<211> LENGTH: 63
<212> TYPE: PRT
<213> ORGANISM: Artificial Sequence
<220> FEATURE:
<223> OTHER INFORMATION: Synthetically generated peptide

<400> SEQUENCE: 83

Lys Gln Ala Pro Lys Gln Pro Pro Lys Pro Lys Lys Pro Lys Thr Gln
1               5                   10                  15

Glu Lys Lys Lys Lys Gln Pro Ala Lys Pro Lys Pro Gly Lys Arg Gln
            20                  25                  30

Arg Met Ala Leu Lys Leu Glu Ala Asp Arg Ser Phe Asp Val Lys Asn
        35                  40                  45

Glu Asp Gly Asp Val Ile Gly His Ala Leu Ala Met Glu Gly Lys
    50                  55                  60

<210> SEQ ID NO 84
<211> LENGTH: 63
<212> TYPE: PRT
<213> ORGANISM: Artificial Sequence
<220> FEATURE:
<223> OTHER INFORMATION: Synthetically generated peptide

<400> SEQUENCE: 84

```
Lys Gln Ala Pro Lys Gln Pro Pro Lys Pro Lys Pro Lys Thr Gln
1               5                   10                  15

Glu Lys Lys Lys Lys Gln Pro Ala Lys Pro Lys Pro Gly Lys Arg Gln
                20                  25                  30

Arg Met Ala Leu Lys Leu Glu Ala Asp Arg Leu Phe Asp Val Lys Asn
            35                  40                  45

Glu Asp Gly Asp Val Ile Gly His Ala Leu Ala Met Glu Gly Lys
    50                  55                  60
```

<210> SEQ ID NO 85
<211> LENGTH: 76
<212> TYPE: PRT
<213> ORGANISM: Artificial Sequence
<220> FEATURE:
<223> OTHER INFORMATION: Synthetically generated peptide

<400> SEQUENCE: 85

```
Ser Gln Lys Gln Lys Gly Gly Gly Gln Gly Lys Lys Lys Lys Asn Gln
1               5                   10                  15

Gly Lys Lys Lys Ala Lys Thr Gly Pro Pro Asn Pro Lys Ala Gln Asn
                20                  25                  30

Gly Asn Lys Lys Thr Asn Lys Lys Pro Gly Lys Arg Gln Arg Met
            35                  40                  45

Val Met Lys Leu Glu Ser Asp Lys Thr Phe Pro Ile Met Leu Glu Gly
    50                  55                  60

Lys Ile Asn Gly Tyr Ala Cys Val Val Gly Gly Lys
65                  70                  75
```

<210> SEQ ID NO 86
<211> LENGTH: 77
<212> TYPE: PRT
<213> ORGANISM: Artificial Sequence
<220> FEATURE:
<223> OTHER INFORMATION: Synthetically generated peptide

<400> SEQUENCE: 86

```
Ala Pro Gln Lys Gln Lys Gly Gly Gly Gln Gly Lys Lys Lys Lys Asn
1               5                   10                  15

Gln Gly Lys Lys Lys Ala Lys Thr Gly Pro Pro Asn Pro Lys Ala Gln
                20                  25                  30

Ser Gly Asn Lys Lys Pro Asn Lys Pro Gly Lys Arg Gln Arg
            35                  40                  45

Met Val Met Lys Leu Glu Ser Asp Lys Thr Phe Pro Ile Met Leu Glu
    50                  55                  60

Gly Lys Ile Asn Gly Tyr Ala Cys Val Val Gly Gly Lys
65                  70                  75
```

<210> SEQ ID NO 87
<211> LENGTH: 76
<212> TYPE: PRT
<213> ORGANISM: Artificial Sequence
<220> FEATURE:

<223> OTHER INFORMATION: Synthetically generated peptide

<400> SEQUENCE: 87

```
Pro Gln Lys Pro Lys Arg Gly Ser Gln Gly Lys Arg Lys Lys Asn Gln
1               5                   10                  15

Gly Lys Lys Ala Lys Thr Gly Pro Pro Asn Gln Lys Ala Gln Asn
            20                  25                  30

Gly Asn Lys Lys Thr Asn Lys Pro Gly Lys Arg Gln Arg Met
        35                  40                  45

Val Met Lys Leu Glu Ser Asp Lys Thr Phe Pro Ile Met Leu Glu Gly
    50                  55                  60

Lys Ile Asn Gly Tyr Ala Cys Val Val Gly Gly Lys
65                  70                  75
```

<210> SEQ ID NO 88
<211> LENGTH: 70
<212> TYPE: PRT
<213> ORGANISM: Artificial Sequence
<220> FEATURE:
<223> OTHER INFORMATION: Consensus sequence

<400> SEQUENCE: 88

```
Gln Lys Pro Lys Gly Gln Gly Lys Lys Lys Asn Gln Gly Lys Lys
1               5                   10                  15

Lys Ala Lys Thr Gly Pro Pro Asn Lys Ala Gln Gly Asn Lys Lys Lys
            20                  25                  30

Asn Lys Lys Pro Gly Lys Arg Gln Arg Met Val Met Lys Leu Glu Ser
        35                  40                  45

Asp Lys Thr Phe Pro Ile Met Leu Glu Gly Lys Ile Asn Gly Tyr Ala
    50                  55                  60

Cys Val Val Gly Gly Lys
65                  70
```

<210> SEQ ID NO 89
<211> LENGTH: 36
<212> TYPE: PRT
<213> ORGANISM: Artificial Sequence
<220> FEATURE:
<223> OTHER INFORMATION: Synthetically generated SINDCE2t E2
      glycoprotein

<400> SEQUENCE: 89

```
Cys Ala Cys Lys Ala Arg Arg Glu Cys Leu Thr Pro Tyr Ala Leu Ala
1               5                   10                  15

Pro Asn Ala Val Ile Pro Thr Ser Leu Ala Leu Leu Cys Cys Val Arg
            20                  25                  30

Ser Ala Asn Ala
        35
```

<210> SEQ ID NO 90
<211> LENGTH: 36
<212> TYPE: PRT
<213> ORGANISM: Artificial Sequence
<220> FEATURE:
<223> OTHER INFORMATION: Synthetically generated SINHRE2t E2
      glycoprotein

<400> SEQUENCE: 90

```
Cys Ala Cys Lys Ala Arg Arg Glu Cys Leu Thr Pro Tyr Ala Leu Ala
1               5                   10                  15

Pro Asn Ala Val Ile Pro Thr Ser Leu Ala Leu Leu Cys Cys Val Arg
```

```
                 20                  25                  30

Ser Ala Asn Ala
        35

<210> SEQ ID NO 91
<211> LENGTH: 36
<212> TYPE: PRT
<213> ORGANISM: Artificial Sequence
<220> FEATURE:
<223> OTHER INFORMATION: Synthetically generated TRDE2t E2 glycoprotein

<400> SEQUENCE: 91

Leu Phe Cys Arg Ser Arg Val Ala Cys Leu Thr Pro Tyr Arg Leu Thr
1               5                   10                  15

Pro Asn Ala Arg Ile Pro Phe Cys Leu Ala Val Leu Cys Cys Ala Arg
            20                  25                  30

Thr Ala Arg Ala
        35

<210> SEQ ID NO 92
<211> LENGTH: 36
<212> TYPE: PRT
<213> ORGANISM: Artificial Sequence
<220> FEATURE:
<223> OTHER INFORMATION: Synthetically generated 6119E2t E2 glycoprotein

<400> SEQUENCE: 92

Leu Phe Cys Lys Ser Arg Val Ser Cys Leu Thr Pro Tyr Arg Leu Thr
1               5                   10                  15

Pro Asn Ala Arg Met Pro Phe Cys Leu Ala Val Leu Cys Cys Ala Arg
            20                  25                  30

Thr Ala Arg Ala
        35

<210> SEQ ID NO 93
<211> LENGTH: 36
<212> TYPE: PRT
<213> ORGANISM: Artificial Sequence
<220> FEATURE:
<223> OTHER INFORMATION: Synthetically generated MAC10E2t E2
      glycoprotein

<400> SEQUENCE: 93

Leu Phe Cys Lys Ser Arg Val Ser Cys Leu Thr Pro Tyr Gln Leu Thr
1               5                   10                  15

Pro Asn Ala Arg Met Pro Phe Cys Leu Ala Val Phe Cys Cys Ala Arg
            20                  25                  30

Thr Ala Arg Ala
        35

<210> SEQ ID NO 94
<211> LENGTH: 34
<212> TYPE: PRT
<213> ORGANISM: Artificial Sequence
<220> FEATURE:
<223> OTHER INFORMATION: Consensus sequence

<400> SEQUENCE: 94

Leu Phe Cys Lys Ser Arg Val Ser Cys Leu Thr Pro Tyr Leu Thr Pro
1               5                   10                  15

Asn Ala Arg Ile Pro Cys Leu Ala Val Leu Cys Cys Ala Arg Thr Ala
            20                  25                  30
```

Arg Ala

<210> SEQ ID NO 95
<211> LENGTH: 327
<212> TYPE: DNA
<213> ORGANISM: Artificial Sequence
<220> FEATURE:
<223> OTHER INFORMATION: Synthetically generated oligonucleotide Chimera
      1A

<400> SEQUENCE: 95
tggccatgac cacccctggcc tcctccgtga agagcttttc ctatcttcgc ggcgcgccca    60
tcaccttgta tggataaggg atcacgggag aaaccgtggg atacgcggtt acacacaata   120
gcgagggctt cttgctatgc aaagttactg acacagtaaa aggagaacgg gtatcgttcc   180
ctgtgtgcac gtacatcccg gccaccatac catgactact ctagctagca gtgttaaatc   240
attcagctac ctgagagggg cccctataac tctctacggc taacctgaat ggactacgac   300
atagtctagt ccgccaagcc tcagcgg                                        327

<210> SEQ ID NO 96
<211> LENGTH: 331
<212> TYPE: DNA
<213> ORGANISM: Artificial Sequence
<220> FEATURE:
<223> OTHER INFORMATION: Synthetically generated oligonucleotide Chimera
      1A complement

<400> SEQUENCE: 96
accggtactg gtgggaccgg aggaggcact tctcgaaaag gatagaagcg ccgcgcgggt    60
agtggaacat acctattccc tagtgccctc tttggcaccc tatgcgccaa tgtgtgttat   120
cgctcccgaa gaacgatacg tttcaatgac tgtgtcattt tcctcttgcc catagcaagg   180
gacacacgtg catgtagggc cggtggtatg gtactgatga gatcgatcgt cacaatttag   240
taagtcgatg gactctcccc ggggatattg agagatgccg attggactta cctgatgctg   300
tatcagatca ggcggttcgg agtcgccgcg c                                  331

<210> SEQ ID NO 97
<211> LENGTH: 346
<212> TYPE: DNA
<213> ORGANISM: Artificial Sequence
<220> FEATURE:
<223> OTHER INFORMATION: Synthetically generated oligonucleotide Chimera
      1B

<400> SEQUENCE: 97
tggccatgac cacccctggcc tcctccgtga agagcttttc ctatcttcgc ggcgcgccca    60
tcaccttgta tggataaggg atcacgggag aaaccgtggg atacgcggtt acacacaata   120
gcgagggctt cttgctatgc aaagttactg acacagtaaa aggagaacgg gtatcgttcc   180
ctgtgtgcac gtacatcccg gccaccataa cttccatcat agttatggcc atgactactc   240
tagctagcag tgttaaatca ttcagctacc tgagagggggc ccctataact ctctacggct   300
aacctgaatg gactacgaca tagtctagtc cgccaagcct cagcgg                   346

<210> SEQ ID NO 98
<211> LENGTH: 132
<212> TYPE: DNA
<213> ORGANISM: Artificial Sequence
<220> FEATURE:
<223> OTHER INFORMATION: Synthetically generated oligonucleotide SIN/VEE
      packaging Chimera #2

```
<400> SEQUENCE: 98
gggatcacgg gagaaaccgt gggatacgcg gttacacaca atagcgaggg cttcttgcta      60
tgcaaagtta ctgacacagt aaaaggagaa cgggtatcgt tccctgtgtg cacgtacatc     120
ccggccacca ta                                                         132

<210> SEQ ID NO 99
<211> LENGTH: 60
<212> TYPE: RNA
<213> ORGANISM: Artificial Sequence
<220> FEATURE:
<223> OTHER INFORMATION: Synthetically generated oligonucleotide SIN
      AR339
<220> FEATURE:
<221> NAME/KEY: CDS
<222> LOCATION: (1)..(60)

<400> SEQUENCE: 99 agg agg acu gaa uac uga cua acc ggg gua ggu ggg uac aua uuu ucg        48
Arg Arg Thr Glu Tyr     Leu Thr Gly Val Gly Gly Tyr Ile Phe Ser
1               5                   10                  15 acg gac aca ggc                                                        60
Thr Asp Thr Gly <210> SEQ ID NO 100
<211> LENGTH: 5
<212> TYPE: PRT
<213> ORGANISM: Artificial Sequence
<220> FEATURE:
<223> OTHER INFORMATION: Synthetic Construct

<400> SEQUENCE: 100

Arg Arg Thr Glu Tyr
1               5

<210> SEQ ID NO 101
<211> LENGTH: 14
<212> TYPE: PRT
<213> ORGANISM: Artificial Sequence
<220> FEATURE:
<223> OTHER INFORMATION: Synthetic Construct

<400> SEQUENCE: 101

Leu Thr Gly Val Gly Gly Tyr Ile Phe Ser Thr Asp Thr Gly
1               5                   10

<210> SEQ ID NO 102
<211> LENGTH: 19
<212> TYPE: PRT
<213> ORGANISM: Artificial Sequence
<220> FEATURE:
<223> OTHER INFORMATION: Synthetically generated peptide: SIN AR339

<400> SEQUENCE: 102

Arg Arg Thr Glu Tyr Leu Thr Gly Val Gly Gly Tyr Ile Phe Ser Thr
1               5                   10                  15

Asp Thr Gly

<210> SEQ ID NO 103
<211> LENGTH: 60
<212> TYPE: RNA
<213> ORGANISM: Artificial Sequence
<220> FEATURE:
<223> OTHER INFORMATION: Synthetically generated oligonucleotide SIN
      AR86
```

```
<220> FEATURE:
<221> NAME/KEY: CDS
<222> LOCATION: (1)..(60)

<400> SEQUENCE: 103 agg agg acc gaa uac ugu cua acc ggg gua ggu ggg uac aua uuu ucg      48
Arg Arg Thr Glu Tyr Cys Leu Thr Gly Val Gly Gly Tyr Ile Phe Ser
1               5                   10                  15 acg gac aca ggc                                                      60
Thr Asp Thr Gly
            20

<210> SEQ ID NO 104
<211> LENGTH: 20
<212> TYPE: PRT
<213> ORGANISM: Artificial Sequence
<220> FEATURE:
<223> OTHER INFORMATION: Synthetic Construct

<400> SEQUENCE: 104

Arg Arg Thr Glu Tyr Cys Leu Thr Gly Val Gly Gly Tyr Ile Phe Ser
1               5                   10                  15

Thr Asp Thr Gly
            20

<210> SEQ ID NO 105
<211> LENGTH: 60
<212> TYPE: RNA
<213> ORGANISM: Artificial Sequence
<220> FEATURE:
<223> OTHER INFORMATION: Synthetically generated oligonucleotide: AURA
<220> FEATURE:
<221> NAME/KEY: CDS
<222> LOCATION: (1)..(60)

<400> SEQUENCE: 105 gga aac aga caa uau uga cua acc ggg gua ggu ggg uac aua uuc ucu      48
Gly Asn Arg Gln Tyr     Leu Thr Gly Val Gly Gly Tyr Ile Phe Ser
1               5                   10                  15 ucu gau aca ggc                                                      60
Ser Asp Thr Gly <210> SEQ ID NO 106
<211> LENGTH: 5
<212> TYPE: PRT
<213> ORGANISM: Artificial Sequence
<220> FEATURE:
<223> OTHER INFORMATION: Synthetic Construct

<400> SEQUENCE: 106

Gly Asn Arg Gln Tyr
1               5

<210> SEQ ID NO 107
<211> LENGTH: 14
<212> TYPE: PRT
<213> ORGANISM: Artificial Sequence
<220> FEATURE:
<223> OTHER INFORMATION: Synthetic Construct

<400> SEQUENCE: 107

Leu Thr Gly Val Gly Gly Tyr Ile Phe Ser Ser Asp Thr Gly
1               5                   10

<210> SEQ ID NO 108
<211> LENGTH: 19
```

```
<212> TYPE: PRT
<213> ORGANISM: Artificial Sequence
<220> FEATURE:
<223> OTHER INFORMATION: Synthetically generated peptide AURA

<400> SEQUENCE: 108

Gly Asn Arg Gln Tyr Leu Thr Gly Val Gly Gly Tyr Ile Phe Ser Ser
1               5                   10                  15

Asp Thr Gly

<210> SEQ ID NO 109
<211> LENGTH: 60
<212> TYPE: RNA
<213> ORGANISM: Artificial Sequence
<220> FEATURE:
<223> OTHER INFORMATION: Synthetically generated oligonucleotide WEE
<220> FEATURE:
<221> NAME/KEY: CDS
<222> LOCATION: (1)..(60)

<400> SEQUENCE: 109 cgu caa cau ucc aac uga cgg uau gaa gcg gga gcg uau auu uuc uca       48
Arg Gln His Ser Asn     Arg Tyr Glu Ala Gly Ala Tyr Ile Phe Ser
1               5                   10                  15 ucg gaa aca ggc                                                       60
Ser Glu Thr Gly <210> SEQ ID NO 110
<211> LENGTH: 5
<212> TYPE: PRT
<213> ORGANISM: Artificial Sequence
<220> FEATURE:
<223> OTHER INFORMATION: Synthetic Construct

<400> SEQUENCE: 110

Arg Gln His Ser Asn
1               5

<210> SEQ ID NO 111
<211> LENGTH: 14
<212> TYPE: PRT
<213> ORGANISM: Artificial Sequence
<220> FEATURE:
<223> OTHER INFORMATION: Synthetic Construct

<400> SEQUENCE: 111

Arg Tyr Glu Ala Gly Ala Tyr Ile Phe Ser Ser Glu Thr Gly
1               5                   10

<210> SEQ ID NO 112
<211> LENGTH: 19
<212> TYPE: PRT
<213> ORGANISM: Artificial Sequence
<220> FEATURE:
<223> OTHER INFORMATION: Synthetically generated peptide WEE

<400> SEQUENCE: 112

Arg Gln His Ser Asn Arg Tyr Glu Ala Gly Ala Tyr Ile Phe Ser Ser
1               5                   10                  15

Glu Thr Gly

<210> SEQ ID NO 113
<211> LENGTH: 60
<212> TYPE: RNA
<213> ORGANISM: Artificial Sequence
<220> FEATURE:
```

```
<223> OTHER INFORMATION: Synthetically generated oligonucleotide EEE
<220> FEATURE:
<221> NAME/KEY: CDS
<222> LOCATION: (1)..(60)

<400> SEQUENCE: 113 cgg agg cac ucg aau uga cgg uac gaa gcg ggc gcg uac auu uuc uca      48
Arg Arg His Ser Asn     Arg Tyr Glu Ala Gly Ala Tyr Ile Phe Ser
1               5                   10                  15 ucc gag acg gga                                                     60
Ser Glu Thr Gly <210> SEQ ID NO 114
<211> LENGTH: 5
<212> TYPE: PRT
<213> ORGANISM: Artificial Sequence
<220> FEATURE:
<223> OTHER INFORMATION: Synthetic Construct

<400> SEQUENCE: 114

Arg Arg His Ser Asn
1               5

<210> SEQ ID NO 115
<211> LENGTH: 14
<212> TYPE: PRT
<213> ORGANISM: Artificial Sequence
<220> FEATURE:
<223> OTHER INFORMATION: Synthetic Construct

<400> SEQUENCE: 115

Arg Tyr Glu Ala Gly Ala Tyr Ile Phe Ser Ser Glu Thr Gly
1               5                   10

<210> SEQ ID NO 116
<211> LENGTH: 19
<212> TYPE: PRT
<213> ORGANISM: Artificial Sequence
<220> FEATURE:
<223> OTHER INFORMATION: Synthetically generated peptide EEE

<400> SEQUENCE: 116

Arg Arg His Ser Asn Arg Tyr Glu Ala Gly Ala Tyr Ile Phe Ser Ser
1               5                   10                  15

Glu Thr Gly

<210> SEQ ID NO 117
<211> LENGTH: 60
<212> TYPE: RNA
<213> ORGANISM: Artificial Sequence
<220> FEATURE:
<223> OTHER INFORMATION: Synthetically generated oligonucleotide VEE
<220> FEATURE:
<221> NAME/KEY: CDS
<222> LOCATION: (1)..(60)

<400> SEQUENCE: 117 gua gca caa caa caa uga cgg uuu gau gcg ggu gca uac auc uuu ucc      48
Val Ala Gln Gln Gln     Arg Phe Asp Ala Gly Ala Tyr Ile Phe Ser
1               5                   10                  15 ucc gac acc ggu                                                     60
Ser Asp Thr Gly

<210> SEQ ID NO 118
<211> LENGTH: 5
<212> TYPE: PRT
```

```
<213> ORGANISM: Artificial Sequence
<220> FEATURE:
<223> OTHER INFORMATION: Synthetic Construct

<400> SEQUENCE: 118

Val Ala Gln Gln Gln
1               5

<210> SEQ ID NO 119
<211> LENGTH: 14
<212> TYPE: PRT
<213> ORGANISM: Artificial Sequence
<220> FEATURE:
<223> OTHER INFORMATION: Synthetic Construct

<400> SEQUENCE: 119

Arg Phe Asp Ala Gly Ala Tyr Ile Phe Ser Ser Asp Thr Gly
1               5                   10

<210> SEQ ID NO 120
<211> LENGTH: 19
<212> TYPE: PRT
<213> ORGANISM: Artificial Sequence
<220> FEATURE:
<223> OTHER INFORMATION: Synthetically generated peptide VEE

<400> SEQUENCE: 120

Val Ala Gln Gln Gln Arg Phe Asp Ala Gly Ala Tyr Ile Phe Ser Ser
1               5                   10                  15

Asp Thr Gly

<210> SEQ ID NO 121
<211> LENGTH: 60
<212> TYPE: RNA
<213> ORGANISM: Artificial Sequence
<220> FEATURE:
<223> OT

```
Leu Asp Arg Ala Gly Ala Tyr Ile Phe Ser Ser Asp Thr Gly
1               5                   10

<210> SEQ ID NO 124
<211> LENGTH: 19
<212> TYPE: PRT
<213> ORGANISM: Artificial Sequence
<220> FEATURE:
<223> OTHER INFORMATION: Synthetically generated peptide MID

<400> SEQUENCE: 124

Arg Leu Thr Ser Ala Leu Asp Arg Ala Gly Ala Tyr Ile Phe Ser Ser
1               5                   10                  15

Asp Thr Gly

<210> SEQ ID NO 125
<211> LENGTH: 60
<212> TYPE: RNA
<213> ORGANISM: Artificial Sequence
<220> FEATURE:
<223> OTHER INFORMATION: Synthetically generated oligonucleotide RR
<220> FEATURE:
<221> NAME/KEY: CDS
<222> LOCATION: (1)..(60)

<400> SEQUENCE: 125 gau uuu gac caa uuc uga cua ggg aca gcg ggg gcg uac auc uuc ucg     48
Asp Phe Asp Gln Phe     Leu Gly Thr Ala Gly Ala Tyr Ile Phe Ser
1               5                   10                  15 ucu gau acc gga                                                     60
Ser Asp Thr Gly <210> SEQ ID NO 126
<211> LENGTH: 5
<212> TYPE: PRT
<213> ORGANISM: Artificial Sequence
<220> FEATURE:
<223> OTHER INFORMATION: Synthetic Construct

<400> SEQUENCE: 126

Asp Phe Asp Gln Phe
1               5

<210> SEQ ID NO 127
<211> LENGTH: 14
<212> TYPE: PRT
<213> ORGANISM: Artificial Sequence
<220> FEATURE:
<223> OTHER INFORMATION: Synthetic Construct

<400> SEQUENCE: 127

Leu Gly Thr Ala Gly Ala Tyr Ile Phe Ser Ser Asp Thr Gly
1               5                   10

<210> SEQ ID NO 128
<211> LENGTH: 19
<212> TYPE: PRT
<213> ORGANISM: Artificial Sequence
<220> FEATURE:
<223> OTHER INFORMATION: Synthetically generated peptide RR

<400> SEQUENCE: 128

Asp Phe Asp Gln Phe Leu Gly Thr Ala Gly Ala Tyr Ile Phe Ser Ser
1               5                   10                  15

Asp Thr Gly
```

<210> SEQ ID NO 129
<211> LENGTH: 60
<212> TYPE: RNA
<213> ORGANISM: Artificial Sequence
<220> FEATURE:
<223> OTHER INFORMATION: Synthetically generated oligonucleotide SF
<220> FEATURE:
<221> NAME/KEY: CDS
<222> LOCATION: (1)..(60)

<400> SEQUENCE: 129

```
uuc gac gac guc cug cga cua ggc cgc gcg ggu gca uau auu uuc ucc      48
Phe Asp Asp Val Leu Arg Leu Gly Arg Ala Gly Ala Tyr Ile Phe Ser
1               5                   10                  15 ucg gac acu ggc                                                      60
Ser Asp Thr Gly
            20
```

<210> SEQ ID NO 130
<211> LENGTH: 20
<212> TYPE: PRT
<213> ORGANISM: Artificial Sequence
<220> FEATURE:
<223> OTHER INFORMATION: Synthetic Construct

<400> SEQUENCE: 130

```
Phe Asp Asp Val Leu Arg Leu Gly Arg Ala Gly Ala Tyr Ile Phe Ser
1               5                   10                  15

Ser Asp Thr Gly
            20
```

<210> SEQ ID NO 131
<211> LENGTH: 60
<212> TYPE: RNA
<213> ORGANISM: Artificial Sequence
<220> FEATURE:
<223> OTHER INFORMATION: Synthetically generated oligonucleotide ONN
<220> FEATURE:
<221> NAME/KEY: CDS
<222> LOCATION: (1)..(60)

<400> SEQUENCE: 131

```
aca gac gaa gag uua cga cua gac aga gca ggg ggu uac aua uuc ucc      48
Thr Asp Glu Glu Leu Arg Leu Asp Arg Ala Gly Gly Tyr Ile Phe Ser
1               5                   10                  15 ucu gac acu ggu                                                      60
Ser Asp Thr Gly
            20
```

<210> SEQ ID NO 132
<211> LENGTH: 20
<212> TYPE: PRT
<213> ORGANISM: Artificial Sequence
<220> FEATURE:
<223> OTHER INFORMATION: Synthetic Construct

<400> SEQUENCE: 132

```
Thr Asp Glu Glu Leu Arg Leu Asp Arg Ala Gly Gly Tyr Ile Phe Ser
1               5                   10                  15

Ser Asp Thr Gly
            20
```

<210> SEQ ID NO 133
<211> LENGTH: 27
<212> TYPE: DNA

```
<213> ORGANISM: Artificial Sequence
<220> FEATURE:
<223> OTHER INFORMATION: 5' PCR primer for nsp3

<400> SEQUENCE: 133
acggccagtg aattgtaata cgactca                                          27

<210> SEQ ID NO 134
<211> LENGTH: 170
<212> TYPE: DNA
<213> ORGANISM: Artificial Sequence
<220> FEATURE:
<223> OTHER INFORMATION: Sindbis Packaging site primer

<400> SEQUENCE: 134
gttcgtagca caacaacaag ggatcacggg agaaaccgtg ggatacgcgg ttacacacaa      60
tagcgagggc ttcttgctat gcaaagttac tgacacagta aaaggagaac gggtatcgtt     120
ccctgtgtgc acgtacatcc cggccaccat atgacggttt gatgcgggtg               170

<210> SEQ ID NO 135
<211> LENGTH: 23
<212> TYPE: DNA
<213> ORGANISM: Artificial Sequence
<220> FEATURE:
<223> OTHER INFORMATION: 3' PCR primer for nsp4

<400> SEQUENCE: 135
ctagtggatc cgagctcggt acc                                             23

<210> SEQ ID NO 136
<211> LENGTH: 10
<212> TYPE: DNA
<213> ORGANISM: Artificial Sequence
<220> FEATURE:
<223> OTHER INFORMATION: Sindbis Pkg. Signal

<400> SEQUENCE: 136
tgacggtttg                                                            10

<210> SEQ ID NO 137
<211> LENGTH: 96
<212> TYPE: DNA
<213> ORGANISM: Artificial sequence
<220> FEATURE:
<223> OTHER INFORMATION: Synthetically generated oligonucleotide

<400> SEQUENCE: 137
atatatattt ataattggct tggtgctggc tactattgtg gccatgtacg tgctgaccaa      60
ccagaaacat aattgaccgc tacgccccaa tgatcc                                96

<210> SEQ ID NO 138
<211> LENGTH: 21
<212> TYPE: DNA
<213> ORGANISM: Artificial sequence
<220> FEATURE:
<223> OTHER INFORMATION: Synthetically generated oligonucleotide

<400> SEQUENCE: 138
ggccgaaatc ggcaaaatcc c                                               21

<210> SEQ ID NO 139
<211> LENGTH: 25
<212> TYPE: DNA
<213> ORGANISM: Artificial sequence
```

<220> FEATURE:
<223> OTHER INFORMATION: Synthetically generated oligonucleotide

<400> SEQUENCE: 139
cacagttttg aatgttcgtt atcgc                                            25

<210> SEQ ID NO 140
<211> LENGTH: 11447
<212> TYPE: DNA
<213> ORGANISM: Venezuelan equine encephalitis virus

<400> SEQUENCE: 140

| | | | | | |
|---|---|---|---|---|---|
| atgggcggcg | catgagagaa | gcccagacca | attacctacc | caaaatggag | aaagttcacg | 60 |
| ttgacatcga | ggaagacagc | ccattcctca | gagctttgca | gcggagcttc | ccgcagtttg | 120 |
| aggtagaagc | caagcaggtc | actgataatg | accatgctaa | tgccagagcg | ttttcgcatc | 180 |
| tggcttcaaa | actgatcgaa | acggaggtgg | acccatccga | cacgatcctt | gacattggaa | 240 |
| gtgcgcccgc | ccgcagaatg | tattctaagc | acaagtatca | ttgtatctgt | ccgatgagat | 300 |
| gtgcggaaga | tccggacaga | ttgtataagt | atgcaactaa | gctgaagaaa | aactgtaagg | 360 |
| aaataactga | taaggaattg | gacaagaaaa | tgaaggagct | cgccgccgtc | atgagcgacc | 420 |
| ctgacctgga | aactgagact | atgtgcctcc | acgacgacga | gtcgtgtcgc | tacgaagggc | 480 |
| aagtcgctgt | ttaccaggat | gtatacgcgc | ttgacggacc | gacaagtctc | tatcaccaag | 540 |
| ccaataaggg | agttagagtc | gcctactgga | taggctttga | caccacccct | tttatgttta | 600 |
| agaacttggc | tggagcatat | ccatcatact | ctaccaactg | ggccgacgaa | accgtgttaa | 660 |
| cggctcgtaa | cataggccta | tgcagctctg | acgttatgga | gcggtcacgt | agagggatgt | 720 |
| ccattcttag | aaagaagtat | ttgaaaccat | ccaacaatgt | tctattctct | gttggctcga | 780 |
| ccatctacca | cgagaagagg | gacttactga | ggagctggca | cctgccgtct | gtatttcact | 840 |
| tacgtggcaa | gcaaaattac | acatgtcggt | gtgagactat | agttagttgc | gacgggtacg | 900 |
| tcgttaaaag | aatagctatc | agtccaggcc | tgtatgggaa | gccttcaggc | tatgctgcta | 960 |
| cgatgcaccg | cgagggattc | ttgtgctgca | aagtgacaga | cacattgaac | ggggagaggg | 1020 |
| tctcttttcc | cgtgtgcacg | tatgtgccag | ctacattgtg | tgaccaaatg | actggcatac | 1080 |
| tggcaacaga | tgtcagtgcg | gacgacgcgc | aaaaactgct | ggttgggctc | aaccagcgta | 1140 |
| tagtcgtcaa | cggtcgcacc | cagagaaaca | ccaataccat | gaaaaattac | cttttgcccg | 1200 |
| tagtggccca | ggcatttgct | aggtgggcaa | aggaatataa | ggaagatcaa | gaagatgaaa | 1260 |
| ggccactagg | actacgagat | agacagttag | tcatggggtg | ttgttgggct | tttagaaggc | 1320 |
| acaagataac | atctatttat | aagcgcccgg | atacccaaac | catcatcaaa | gtgaacagcg | 1380 |
| atttccactc | attcgtgctg | cccaggatag | cagtaacac | attggagatc | gggctgagaa | 1440 |
| caagaatcag | gaaaatgtta | gaggagcaca | aggagccgtc | acctctcatt | accgccgagg | 1500 |
| acgtacaaga | agctaagtgc | gcagccgatg | aggctaagga | ggtgcgtgaa | gccgaggagt | 1560 |
| tgcgcgcagc | tctaccacct | tggcagctg | atgttgagga | gcccactctg | gaagccgatg | 1620 |
| tcgacttgat | gttacaagag | gctgggggccg | gctcagtgga | gacacctcgt | ggcttgataa | 1680 |
| aggttaccag | ctacgctggc | gaggacaaga | tcggctctta | cgctgtgctt | tctcccgcagg | 1740 |
| ctgtactcaa | gagtgaaaaa | ttatcttgca | tccaccctct | cgctgaacaa | gtcatagtga | 1800 |
| taacacactc | tggccgaaaa | gggcgttatg | ccgtggaacc | ataccatggt | aaagtagtgg | 1860 |
| tgccagaggg | acatgcaata | cccgtccagg | actttcaagc | tctgagtgaa | agtgccacca | 1920 |

```
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg acgtcaatg   2340 ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttaac atgatgtgcc   2520 tgaaagtgca ttttaaccac gagatttgca cacaagtctt ccacaaaagc atctctcgcc   2580
gttgcactaa atctgtgact tcggtcgtct caaccttgtt ttacgacaaa aaatgagaa   2640 cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggaccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca gttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
```

```
acgataacaa ttacaagtca gtagcgattc cactgttgtc caccggcatc tttccggga      4380 acaaagatcg actaacccaa tcattgaacc atttgctgac agctttagac accactgatg      4440
cagatgtagc catatactgc agggacaaga atgggaaat gactctcaag gaagcagtgg       4500
ctaggagaga agcagtggag gagatatgca tatccgacga ctcttcagtg acagaacctg      4560
atgcagagct ggtgagggtg catccgaaga gttctttggc tggaaggaag ggctacagca     4620
caagcgatgg caaaactttc tcatatttgg aagggaccaa gtttcaccag gcggccaagg     4680
atatagcaga aattaatgcc atgtggcccg ttgcaacgga ggccaatgag caggtatgca     4740
tgtatatcct cggagaaagc atgagcagta ttaggtcgaa atgccccgtc gaagagtcgg     4800
aagcctccac accacctagc acgctgcctt gcttgtgcat ccatgccatg actccagaaa     4860
gagtacagcg cctaaaagcc tcacgtccag aacaaattac tgtgtgctca tccttccat    4920 tgccgaagta tagaatcact ggtgtgcaga agatccaatg ctcccagcct atattgttct     4980
caccgaaagt gcctgcgtat attcatccaa ggaagtatct cgtggaaaca ccaccggtag     5040
acgagactcc ggagccatcg gcagagaacc aatccacaga ggggacacct gaacaaccac     5100
cacttataac cgaggatgag accaggacta gaacgcctga gccgatcatc atcgaagagg     5160
aagaagagga tagcataagt ttgctgtcag atggcccgac ccaccaggtg ctgcaagtcg     5220
aggcagacat tcacgggccg ccctctgtat ctagctcatc ctggtccatt cctcatgcat     5280
ccgactttga tgtggacagt ttatccatac ttgacaccct ggagggagct agcgtgacca     5340
gcggggcaac gtcagccgag actaactctt acttcgcaaa gagtatggag tttctggcgc     5400
gaccggtgcc tgcgcctcga acagtattca ggaaccctcc acatcccgct ccgcgcacaa     5460
gaacaccgtc acttgcaccc agcagggcct gctcgagaac cagcctagtt ccaccccgc      5520 caggcgtgaa tagggtgatc actagagagg agctcgaggc gcttaccccg tcacgcactc     5580
ctagcaggtc ggtctcgaga accagcctgg tctccaaccc gccaggcgta aatagggtga     5640
ttacaagaga ggagtttgag gcgttcgtag cacaacaaca atgacggttt gatgcgggtg     5700
catacatctt ttcctccgac accggtcaag ggcatttaca acaaaaatca gtaaggcaaa     5760
cggtgctatc cgaagtggtg ttggagagga ccgaattgga gatttcgtat gccccgcgcc     5820
tcgaccaaga aaaagaagaa ttactacgca agaaattaca gttaaatccc acacctgcta     5880
acagaagcag ataccagtcc aggaaggtgg agaacatgaa agccataaca gctagacgta     5940
ttctgcaagg cctagggcat tatttgaagg cagaaggaaa agtggagtgc taccgaaccc     6000
tgcatcctgt tcctttgtat tcatctagtg tgaaccgtgc cttttcaagc cccaaggtcg     6060
cagtggaagc ctgtaacgcc atgttgaaag agaactttcc gactgtggct tcttactgta     6120
ttattccaga gtacgatgcc tatttggaca tggttgacgg agcttcatgc tgcttagaca     6180
ctgccagttt ttgccctgca aagctgcgca gctttccaaa gaaacactcc tatttggaac     6240
ccacaatacg atcggcagtg ccttcagcga tccagaacac gctccagaac gtcctggcag     6300
ctgccacaaa agaaattgc aatgtcacgc aaatgagaga attgcccgta ttggattcgg      6360
cggcctttaa tgtggaatgc ttcaagaaat atgcgtgtaa taatgaatat gggaaacgt      6420 ttaaagaaaa ccccatcagg cttactgaag aaaacgtggt aaattacatt accaaattaa     6480
aaggaccaaa agctgctgct ctttttgcga agacacataa tttgaatatg ttgcaggaca     6540
taccaatgga caggttttgta atggacttaa agagagacgt gaaagtgact ccaggaacaa      6600
aacatactga agaacggccc aaggtacagg tgatccaggc tgccgatccg ctagcaacag     6660
cgtatctgtg cggaatccac cgagagctgg ttaggagatt aaatgcggtc ctgcttccga     6720
```

```
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgttcccg ttcagccaa tgtatccgat gcagccaatg ccctatcgca acccgttcgc   7620
ggccccgcgc aggccctggt tccccagaac cgacccttt ctggcgatgc aggtgcagga   7680
attaacccgc tcgatggcta acctgacgtt caagcaacgc cggacgcgc cacctgaggg   7740
gccatccgct aagaaaccga agaaggaggc ctcgcaaaaa cagaaagggg gaggccaagg   7800
gaagaagaag aagaaccaag ggaagaagaa ggctaagaca gggccgccta atccgaaggc   7860
acagaatgga aacaagaaga agaccaacaa gaaaccaggc aagagacagc gcatggtcat   7920
gaaattggaa tctgacaaga cgttcccaat catgttggaa gggaagataa acggctacgc   7980
ttgtgtggtc ggagggaagt tattcaggcc gatgcatgtg gaaggcaaga tcgacaacga   8040
cgttctggcc gcgcttaaga cgaagaaagc atccaaatac gatcttgagt atgcagatgt   8100
gccacagaac atgcgggccg atacattcaa atacacccat gagaaacccc aaggctatta   8160
cagctggcat catggagcag tccaatatga aaatgggcgt ttcacggtgc cgaaaggagt   8220
tgggccaag ggagacagcg gacgacccat tctggataac cagggacggg tggtcgctat   8280
tgtgctggga ggtgtgaatg aaggatctag gacagcccct tcagtcgtca tgtgaacga   8340
gaagggagtt accgtgaagt atactccgga gaactgcgag caatggtcac tagtgaccac   8400
catgtgtctg ctcgccaatg tgacgttccc atgtgctcaa ccaccaattt gctacgacag   8460
aaaaccagca gagactttgg ccatgctcag cgttaacgtt gacaacccgg gctacgatga   8520
gctgctggaa gcagctgtta gtgcccggg aaggaaaagg agatccaccg aggagctgtt   8580
taaggagtat aagctaacgc gcccttacat ggccagatgc atcagatgtg cagttgggag   8640
ctgccatagt ccaatagcaa tcgaggcagt aaagagcgac gggcacgacg gttatgttag   8700
acttcagact tcctcgcagt atggcctgga ttcctccggc aacttaaagg gcaggaccat   8760
gcggtatgac atgcacggga ccattaaaga gataccacta catcaagtgt cactccatac   8820
atctcgcccg tgtcacattg tggatgggca cggttatttc ctgcttgcca ggtgcccggc   8880
aggggactcc atcaccatgg aatttaagaa agattccgtc acacactcct gctcggtgcc   8940
gtatgaagtg aaatttaatc ctgtaggcag agaactctat actcatcccc cagaacacgg   9000
agtagagcaa gcgtgccaag tctacgcaca tgatgcacag aacagaggag cttatgtcga   9060
gatgcacctc ccgggctcag aagtggacag cagtttggtt tccttgagcg gcagttcagt   9120
```

-continued

```
caccgtgaca cctcctgttg ggactagcgc cctggtggaa tgcgagtgtg gcggcacaaa   9180
gatctccgag accatcaaca agacaaaaca gttcagccag tgcacaaaga aggagcagtg   9240
cagagcatat cggctgcaga acgataagtg ggtgtataat tctgacaaac tgcccaaagc   9300
agcgggagcc accttaaaag gaaaactgca tgtcccattc ttgctggcag acggcaaatg   9360
caccgtgcct ctagcaccag aacctatgat aacctttggt ttcagatcag tgtcactgaa   9420
actgcaccct aagaatccca catatctaac cacccgccaa cttgctgatg agcctcacta   9480
cacgcacgag ctcatatctg aaccagctgt taggaatttt accgtcaccg aaaaagggtg   9540
ggagtttgta tggggaaacc acccgccgaa aaggttttgg gcacaggaaa cagcacccgg   9600
aaatccacat gggctaccgc acgaggtgat aactcattat taccacagat accctatgtc   9660
caccatcctg ggtttgtcaa tttgtgccgc cattgcaacc gtttccgttg cagcgtctac   9720
ctggctgttt tgcagatcta gagttgcgtg cctaactcct taccggctaa cacctaacgc   9780
taggatacca ttttgtctgg ctgtgctttg ctgcgcccgc actgcccggg ccgagaccac   9840
ctgggagtcc ttggatcacc tatggaacaa taaccaacag atgttctgga ttcaattgct   9900
gatccctctg gccgccttga tcgtagtgac tcgcctgctc aggtgcgtgt gctgtgtcgt   9960 gccttttta gtcatggccg gcgccgcagg cgccggcgcc tacgagcacg cgaccacgat  10020
gccgagccaa gcgggaatct cgtataacac tatagtcaac agagcaggct acgcaccact  10080
ccctatcagc ataacaccaa caaagatcaa gctgatacct acagtgaact ggagtacgt  10140 cacctgccac tacaaaacag gaatggattc accagccatc aaatgctgcg gatctcagga  10200
atgcactcca acttacaggc ctgatgaaca gtgcaaagtc ttcacagggg tttacccgtt  10260
catgtggggt ggtgcatatt gcttttgcga cactgagaac acccaagtca gcaaggccta  10320
cgtaatgaaa tctgacgact gccttgcgga tcatgctgaa gcatataaag cgcacacagc  10380
ctcagtgcag gcgttcctca acatcacagt gggagaacac tctattgtga ctaccgtgta  10440
tgtgaatgga gaaactcctg tgaatttcaa tgggtcaaa ttaactgcag gtccgctttc  10500
cacagcttgg acacccttg atcgcaaaat cgtgcagtat gccgggggaga tctataatta  10560 tgattttcct gagtatgggg caggacaacc aggagcattt ggagatatac aatccagaac  10620
agtctcaagc tcagatctgt atgccaatac caacctagtg ctgcagagac ccaaagcagg  10680
agcgatccac gtgccataca ctcaggcacc ttcgggtttt gagcaatgga gaaagataa  10740 agctccatca ttgaaattta ccgccccttt cggatgcgaa atatatacaa accccattcg  10800
cgccgaaaac tgtgctgtag ggtcaattcc attagccttt gacattcccg acgccttgtt  10860
caccagggtg tcagaaacac cgacactttc agcggccgaa tgcactctta acgagtgcgt  10920
gtattcttcc gactttggtg ggatcgccac ggtcaagtac tcggccagca agtcaggcaa  10980
gtgcgcagtc catgtgccat cagggactgc taccctaaaa gaagcagcag tcgagctaac  11040
cgagcaaggg tcggcgacta tccattctc gaccgcaaat atccaccgg agttcaggct  11100 ccaaatatgc acatcatatg ttacgtgcaa aggtgattgt caccccccga aagaccatat  11160
tgtgacacac cctcagtatc acgcccaaac atttacagcc gcggtgtcaa aaaccgcgtg  11220
gacgtggtta acatccctgc tgggaggatc agccgtaatt attataattg cttggtgct  11280 ggctactatt gtggccatgt acgtgctgac caaccagaaa cataattgaa tacagcagca  11340
attggcaagc tgcttacata gaactcgcgg cgattggcat gccgccttaa aatttttatt  11400
ttattttttc ttttctttc cgaatcggat tttgttttta atatttc                 11447
```